United States Patent
Baselga et al.

(10) Patent No.: US 10,864,215 B2
(45) Date of Patent: Dec. 15, 2020

(54) USE OF PHOSPHOINOSITIDE 3-KINASE INHIBITORS FOR TREATMENT OF VASCULAR MALFORMATIONS

(71) Applicant: MEMORIAL SLOAN-KETTERING CANCER CENTER, New York, NY (US)

(72) Inventors: Eulalia Baselga, Tiana (ES); Pau Castel, New York, NY (US); Jose T. Baselga, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 15/811,973

(22) Filed: Nov. 14, 2017

(65) Prior Publication Data
US 2018/0117055 A1 May 3, 2018

Related U.S. Application Data

(63) Continuation of application No. PCT/US2016/032779, filed on May 16, 2016.

(60) Provisional application No. 62/313,476, filed on Mar. 25, 2016, provisional application No. 62/265,641, filed on Dec. 10, 2015, provisional application No. 62/162,534, filed on May 15, 2015.

(51) Int. Cl.
| | | |
|---|---|---|
| *A61K 31/4439* | (2006.01) | |
| *A61P 9/00* | (2006.01) | |
| *A61K 31/5377* | (2006.01) | |
| *A61K 31/427* | (2006.01) | |
| *A61K 31/444* | (2006.01) | |
| *A61K 31/519* | (2006.01) | |
| *A61K 31/4375* | (2006.01) | |

(52) U.S. Cl.
CPC ........ *A61K 31/5377* (2013.01); *A61K 31/427* (2013.01); *A61K 31/4375* (2013.01); *A61K 31/444* (2013.01); *A61K 31/4439* (2013.01); *A61K 31/519* (2013.01); *A61P 9/00* (2018.01)

(58) Field of Classification Search
CPC .............. A61K 31/5377; A61K 31/427; A61K 31/4375; A61K 31/4439; A61K 31/444; A61K 31/519
See application file for complete search history.

(56) References Cited

U.S. PATENT DOCUMENTS

2013/0189274 A1 7/2013 Berkenblit et al.
2013/0345232 A1 12/2013 Lane et al.

FOREIGN PATENT DOCUMENTS

| WO | WO 2007/021933 A2 | 2/2007 |
|---|---|---|
| WO | WO 2013/015833 A2 | 1/2013 |
| WO | WO 2013/182668 A1 | 12/2013 |
| WO | WO 2014/046617 A1 | 3/2014 |
| WO | WO 2017/140828 A1 | 8/2017 |

OTHER PUBLICATIONS

Adams et al., "Cooperation between Pik3ca and p53 Mutations in Mouse Mammary Tumor Formation," Cancer Research 71(7):2706-2717 (2011).
Adams et al., "Molecular regulation of angiogenesis and lymphangiogenesis," Nature Reviews. Molecular Cell Biology 8:464-478 (2007).
Arnaoutova et al., "The endothelial cell tube formation assay on basement membrane turns 20: state of the science and the art," Angiogenesis 12:267-274 (2009).
Banerji et al., "LYVE-1, a New Homologue of the CD44 Glycoprotein, Is a Lymph-Specific Receptor for Hyaluronan," The Journal of Cell Biology 144(4):789-801 (1999).
Blatt et al., "A review of contemporary options for medical management of hemangiomas, other vascular tumors, and vascular malformations," Pharmacology & Therapeutics 139:327-333 (2013).
Boscolo et al., "Rapamycin improves TIE2-mutated venous malformation in murine model and human subjects," The Journal of Clinical Investigation 125(9):3491-3504 (2015).
Brouillard et al., "Genetic causes of vascular malformations," Human Molecular Genetics 16(2):R140-149 (2007).
Brouillard et al., "Genetics of lymphatic anomalies," The Journal of Clinical Investigation 124(3):898-904 (2014).
Brouillard et al., "Vascular malformations: localized defects in vascular morphogenesis," Clinical Genetics 63:340-351 (2003).
Calvert et al., "Allelic and locus heterogeneity in inherited venous malformations," Human Molecular Genetics 8(7):1279-1289 (1999).
Castillo et al., "Somatic activating mutations in Pik3ca cause sporadic venous malformations in mice and humans," Science Translational Medicine 8:332ra43 (2016).
Cheng et al., "Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology," The Journal of Molecular Diagnostics 17(3):251-264 (2015).
Contreras et al., "Lkb1 inactivation is sufficient to drive endometrial cancers that are aggressive yet highly responsive to mTOR inhibitor monotherapy," Disease Models & Mechanisms 3:181-193 (2010).
Costa Da Cunha Castro et al. "Prox-1 and VEGFR3 Antibodies are Superior to D2-40 in Identifying Endothelial Cells of Lymphatic Malformations—A Proposal of a New Immunohistochemical Panel to Differentiate Lymphatic from Other Vascular Malformations," Pediatric and Developmental Pathology 12:187-194 (2009).
Cox et al., "Vascular Malformations: A Review," Semin Plast Surg 28:58-63 (2014).
Daly et al., "Angiopoietin-2 functions as an autocrine protective factor in stressed endothelial cells," PNAS USA 103(42):15491-15496 (2006).

(Continued)

*Primary Examiner* — Irina Neagu
(74) *Attorney, Agent, or Firm* — Baker Botts L.L.P.

(57) ABSTRACT

The present disclosure relates to methods of treating a vascular malformation in a subject expressing a gain-of-function mutation in a PIK3CA gene comprising administering, to the subject, an effective amount of an agent that inhibits phosphoinositide 3-kinase ("PI3K").

9 Claims, 39 Drawing Sheets

Figure 1A:
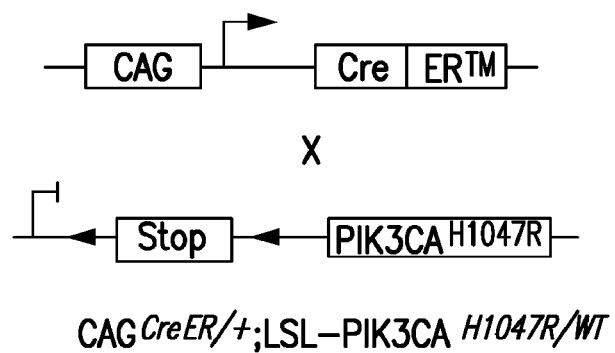
Figure 1B:
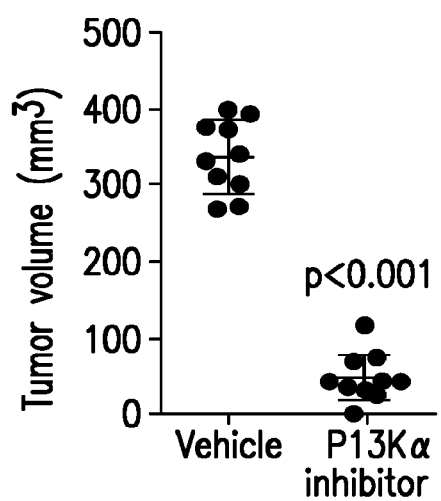

Specification includes a Sequence Listing.

(56) References Cited

OTHER PUBLICATIONS

Dannemann et al., "Phosphatidylinositol 4,5-bisphosphate-specific AKT1 is oncogenic," Int. J. Cancer, 127(1):239-244 (2010).
De Lorimier, "Sclerotherapy for Venous Malformations," J Pediatr Surg 30(2):188-194 (1995).
Dompmartin et al., "Elevated D-dimer Level is Diagnostic for Venous Malformations," Archives of Dermatology 145(11):1239-1244 (2009).
Dompmartin et al., "Venous Malformation: update on etiopathogenesis, diagnosis and management," Phlebology 25(5):224-235 (2010).
Engelman, "Targeting PI3K signalling in cancer: opportunities, challenges and limitations," Nature Reviews. Cancer 9:550-562 (2009).
Fritsch et al., "Characterization of the Novel and Specific PI3Kα Inhibitor NVP-BYL719 and Development of the Patient Stratification Strategy for Clinical Trials," Molecular Cancer Therapeutics 13(5):1117-1129 (2014).
Fruman et al., "PI3K and Cancer: Lessons, Challenges and Opportunities," Nature Reviews. Drug Discovery 13(2):140-156 (2014).
Graupera et al., "Angiogenesis selectively requires the p110α isoform of PI3K to control endothelial cell migration," Nature 453:662-666 (2008).
Graupera et al., "Regulation of angiogenesis by PI3K signaling networks," Experimental Cell Research 319:1348-1355 (2013).
Hammill et al., "Sirolimus for the Treatment of Complicated Vascular Anomalies in Children," Pediatric Blood Cancer 57:1018-1024 (2011).
Hare et al., "Heterozygous expression of the oncogenic Pik3ca(H1047R) mutation during murine development results in fatal embryonic and extraembryonic defects," Developmental Biology 404:14-26 (2015).
Hayakawa et al. "Synthesis and biological evaluation of 4-morpholino-2-phenylquinazolines and related derivatives as novel PI3 kinase p110α inhibitors," Bioorg. Med. Chem. 14:6847-6858 (2006).
Hayashi et al., "Efficient Recombination in Diverse Tissues by a Tamoxifen-Inducible Form of Cre: A Tool for Temporally Regulated Gene Activation/Inactivation in the Mouse," Developmental Biology 244:305-318 (2002).
Herbert et al., "Molecular control of endothelial cell behaviour during blood vessel morphogenesis," Nature Reviews. Molecular Cell Biology 12(9):551-564 (2011).
Heyer et al., "Non-germline genetically engineered mouse models for translational cancer research," Nat Rev Cancer 10(7):470-480 (2010).
Hu et al., "Tie2-R849W Mutant in Venous Malformations Chronically Activates a Functional STAT1 to Modulate Gene Expression," Journal of Investigative Dermatology, 128:2325-2333 (2008).
International Search Report dated Sep. 15, 2016 in International Application No. PCT/US16/32779.
Jones et al., "Identification of Tek/Tie2 Binding Partners. Binding to a Multifunctional Docking Site Mediates Cell Survival and Migration," The Journal of Biological Chemistry 274(43):30896-30905 (1999).
Kang et al., "Clinical and Genetic Aspects of the Segmental Overgrowth Spectrum Due to Somatic Mutations in PIK3CA," The Journal of Pediatrics, 167(5):957-962 (2015).
Kang et al., "Phosphatidylinositol 3-kinase mutations identified in human cancer are oncogenic," PNAS USA 102(3):802-807 (2005).
Keppler-Noreuil et al., "PIK3CA-Related Overgrowth Spectrum (PROS): Diagnostic and Testing Eligibility Criteria, Differential Diagnosis, and Evaluation," American Journal of Medical Genetics, Part A 167A:287-295 (2015).
Kim et al., "Angiopoietin-1 Regulates Endothelial Cell Survival Through the Phosphatidylinositol 3'-Kinase/Akt Signal Transduction Pathway," Circulation Research 86:24-29 (2000).
Kisanuki et al., "Tie2-Cre Transgenic Mice: A New Model for Endothelial Cell-Lineage Analysis in Vivo," Developmental Biology 230:230-242 (2001).
Knight et al., "A Pharmacological Map of the PI3-K Family Defines a Role for p110α in Insulin Signaling," Cell 125(4):733-747 (2006).
Kondapaka et al., "Perifosine, a novel alkylphospholipid, inhibits protein kinase B activation," Mol. Cancer Ther. 2:1093-1103 (2003).
Kontos et al., "Tyrosine 1101 of Tie2 Is the Major Site of Association of p85 and Is Required for Activation of Phosphatidylinositol 3-Kinase and Akt," Molecular and Cellular Biology 18(7):4131-4140 (1998).
Krings, "Vascular Malformations of the Spine and Spinal Cord. Anatomy, Classification, Treatment," Clinical Neuroradiology 20:5-24 (2010).
Kurek et al., "Somatic Mosaic Activating Mutations in PIK3CA Cause CLOVES Syndrome," American Journal of Human Genetics 90:1108-1115 (2012).
Lackner et al., "Sirolimus for the treatment of children with various complicated vascular anomalies," European Journal of Pediatrics 174:1579-1584 (2015).
Lawley et al., "Expression of Wilms Tumor 1 Gene Distinguishes Vascular Malformations from Proliferative Endothelial Lesions," Archives of Dermatology 141:1297-1300 (2005).
Leaute-Labreze et al., "A Randomized, Controlled Trial of Oral Propranolol in Infantile Hemangioma," The New England Journal of Medicine 372:735-746 (2015).
Limaye et al., "Somatic Mutations in Angiopoietin Receptor TIE2 Can Cause Both Solitary and Multiple Sporadic Venous Malformations," Nature Genetics 41(1):118-124 (2009).
Lindhurst et al., "A Mosaic Activating Mutation in AKT1 Associated with the Proteus Syndrome," N Engl J Med 365:611-619 (2011).
Lindhurst et al., "Mosaic Overgrowth with Fibroadipose Hyperplasia is Caused by Somatic Activating Mutations in PIK3CA," Nature Genetics 44(8):928-933 (2012).
Luks et al., "Lymphatic and Other Vascular Malformative/Overgrowth Disorders Are Caused by Somatic Mutations in PIK3CA," J Pediatr 166(4):1048-1054 (2015).
Marsh et al., "Germline mutations in PTEN are present in Bannayan-Zonana syndrome," Nature Genetics 16:333-334 (1997).
Morris et al., "Functional analysis of a mutant form of the receptor tyrosine kinase Tie2 causing venous malformations," Journal of Molecular Medicine 83:58-63 (2005).
Mouta-Bellum et al., "Organ-specific lymphangiectasia, arrested lymphatic sprouting, and maturation defects resulting from gene-targeting of the PI3K regulatory isoforms p85α, p55α, and p50α," Developmental Dynamics 238(10):2670-2679 (2009).
Natynki et al., "Common and specific effects of TIE2 mutations causing venous malformations," Human Molecular Genetics 24(22):6374-6389 (2015).
Nguyen et al., "Genetics of vascular malformations," Seminars in Pediatric Surgery 23:221-226 (2014).
North et al., "GLUT1: A Newly Discovered Immunohistochemical Marker for Juvenile Hemangiomas," Human Pathology 31(1):11-22 (2000).
Osborn et al., "Activating PIK3CA alleles and lymphangiogenic phenotype of lymphatic endothelial cells isolated from lymphatic malformations," Human Molecular Genetics 24(4):926-938 (2015).
Pfohler et al., "Successful treatment of a congenital extra-truncal vascular malformation by orally administered propranolol," J Dermatol Treat 26(1):59-62 (2015).
Riviere et al., "De novo germline and postzygotic mutations in AKT3, PIK3R2 and PIK3CA cause a spectrum of related megalencephaly syndromes," Nature Genetics 44(8):934-940 (2013).
Rodon et al., "Development of PI3K inhibitors: lessons learned from early clinical trials," Nature Reviews. Clinical Oncology 10:143-153 (2013).
Roy et al., "Mouse models of human PIK3CA-related brain overgrowth have acutely treatable epilepsy," International Journal of Developmental Neuroscience, 55 pages (2015).
Ruzankina et al., "Deletion of the Developmentally Essential Gene ATR in Adult Mice Leads to Age-Related Phenotypes and Stem Cell Loss," Cell Stem Cell 1(1):113-126 (2007).
Samuels et al., "Mutant PIK3CA promotes cell growth and invasion of human cancer cells," Cancer Cell 7:561-573 (2005).
Sarbassov et al., "Prolonged Rapamycin Treatment Inhibits mTORC2 Assembly and Akt/PKB," Molecular Cell 22:159-168 (2006).

(56) References Cited

OTHER PUBLICATIONS

Shirley et al., "Sturge-Weber Syndrome and Port-Wine Stains Caused by Somatic Mutation in GNAQ," The New England Journal of Medicine 368(21):1971-1979 (2013).
Smith et al., "Mechanisms of vascular stability and the relationship to human disease," Current Opinion in Hematology 17:237-244 (2010).
Soblet et al., "Variable Somatic TIE2 Mutations in Half of Sporadic Venous Malformations," Molecular Syndromology 4:179-183 (2013).
The Cancer Genome Atlas Research Network, "Integrated Genomic Characterization of Endometrial Carcinoma," Nature 497(7447):67-73 (2013).
Thurston et al., "The Complex Role of Angiopoietin-2 in the Angiopoietin-Tie Signaling Pathway," Cold Spring Harbor Perspect Med 2:a006550 (2012).
Tian et al., "Identification of an angiogenic factor that when mutated causes susceptibility to Klippel-Trenaunay syndrome," Nature 427(6975):640-645 (2004).
Uebelhoer et al., "Vascular Anomalies: From Genetics Toward Models for Therapeutic Trials," Cold Spring Harbor Prespect Med 2:a009688 (2012).
Uebelhoer et al., "Venous malformation-causative TIE2 mutations mediate an AKT-dependent decrease in PDGFB," Human Molecular Genetics 22(17):3438-3448 (2013).
Van Miltenburg et al., "Using genetically engineered mouse models to validate candidate cancer genes and test new therapeutic approaches," Curr Opin Genet Dev 22:21-27 (2012).
Vikkula et al., "Vascular Dysmorphogenesis Caused by an Activating Mutation in the Receptor Tyrosine Kinase TIE2," Cell 87:1181-1190 (1996).
Wassef et al., "Vascular Anomalies Classification: Recommendations From the International Society for the Study of Vascular Anomalies," Pediatrics 136(1):1-14 (2015).
Wouters et al., "Hereditary cutaneomucosal venous malformations are caused by TIE2 mutations with widely variable hyperphosphorylating effects," Eur J Hum Genet 18:414-420 (2010).
Yuan et al., "Angiopoietin 2 is a Partial Agonist/Antagonist of Tie2 Signaling in the Endothelium," Molecular and Cellular Biology 29(8):2011-2022 (2009).
Zou et al., "A novel dual PI3Kα/mTOR inhibitor PI-103 with high antitumor activity in non-small cell lung cancer cells," Int. J Mol. Med. 24:97-101 (2009).
Supplementary European Search Report dated Dec. 14, 2018 in EP Application No. 16797120.

DA: Dorsal aorta
CV: Cardinal vein

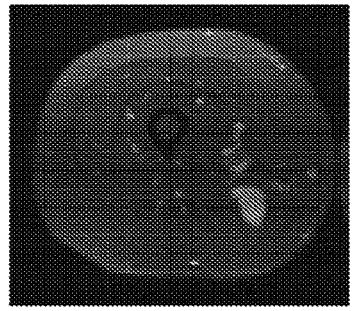
FIG. 5A
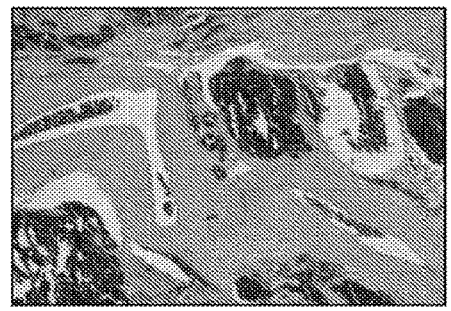
FIG. 5B
| | Cases | % | PI3K/AKT | ERK/MEK | DNA repair |
|---|---|---|---|---|---|
| PIK3CA | 6 | 33.3 | ■ | | |
| ARID1A | 1 | 5.8 | | | ■ |
| MDC1 | 1 | 5.8 | | | ■ |
| BARD1 | 1 | 5.8 | | | ■ |
| GNAQ | 1 | 5.8 | | | |
| TERT | 1 | 5.8 | | | ■ |
| MAP2K1 | 1 | 5.8 | | ■ | |
| MED12 | 1 | 5.8 | | | |
| AKT3 | 1 | 5.8 | ■ | | |
| AKT2 | 1 | 5.8 | ■ | | |
| FOXL2 | 1 | 5.8 | | | |
| BCOR | 1 | 5.8 | | | |
| MLL2 | 1 | 5.8 | | | ■ |
| ATM | 1 | 5.8 | | | |
| MAP3K1 | 1 | 5.8 | | ■ | |
| TGFBR2 | 1 | 5.8 | | | |
| PHOX28 | 1 | 5.8 | | | |
| IRS2 | 1 | 5.8 | ■ | | |
FIG. 5C
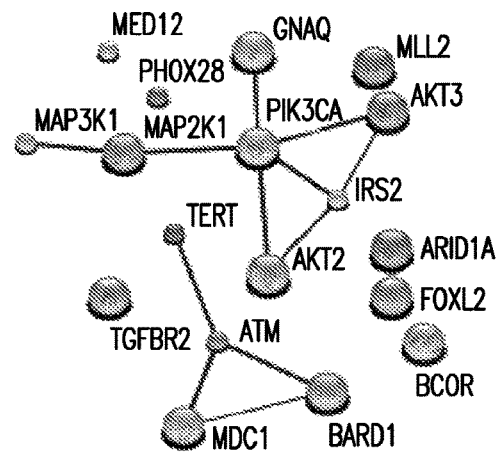
FIG. 5D

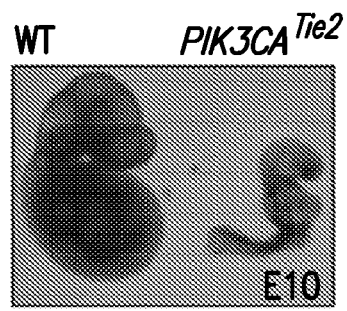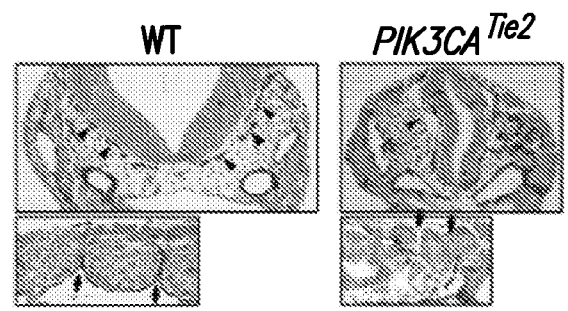
FIG. 10A    FIG. 10B
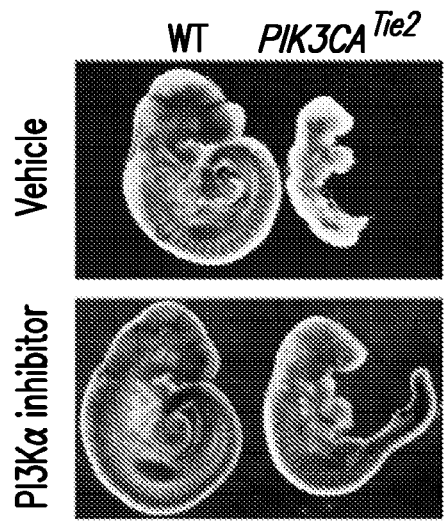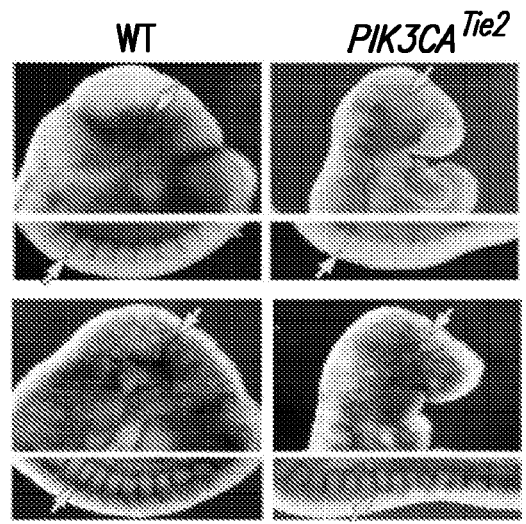
FIG. 10C    FIG. 10D
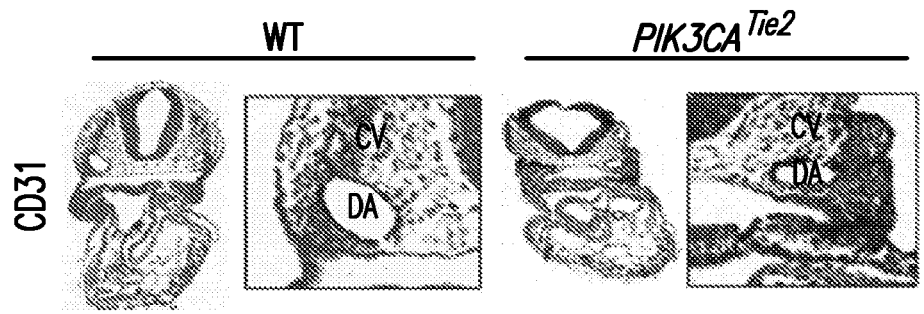
FIG. 10E

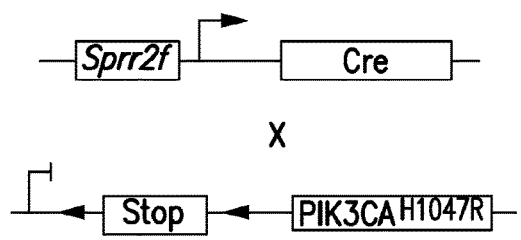
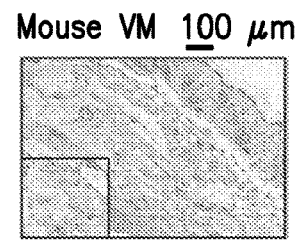
FIG. 11A
FIG. 11B
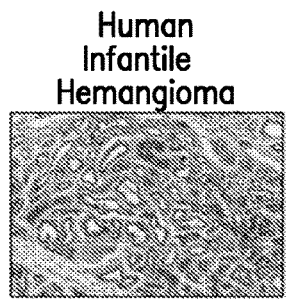
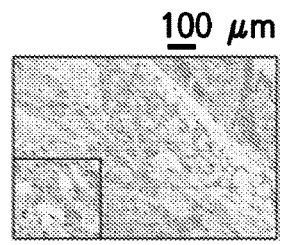
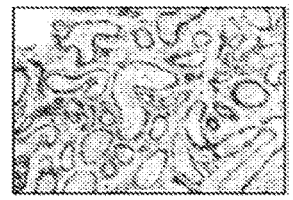
FIG. 11C
FIG. 11D
FIG. 11E
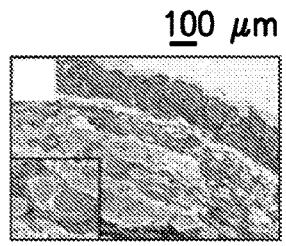
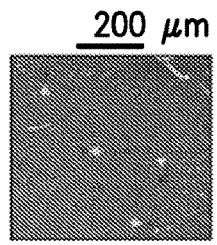
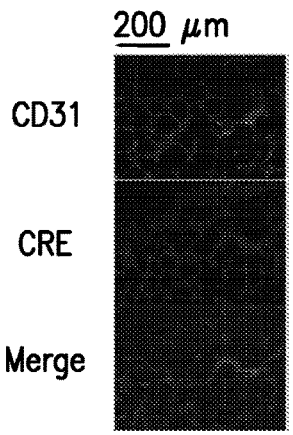
FIG. 11F
FIG. 11G
FIG. 11H

PIK3CA E542K PIK3CA H1047R

| Patient | Sex | Age | Localization | TEK mutation | PIK3CA mutation | Other mutations | Sequencing Coverage | Notes |
|---|---|---|---|---|---|---|---|---|
| VM-003 | M | 41 | Soft tissue, orbit | | | | 838.0 | No mutations detected |
| VM-004 | F | 14 | Muscle, buttock | Y897H; R918L | I143V | AKT2 (K181M) | 243.5 | |
| VM-005 | M | 72 | Subcutaneous, finger | Y897N; R918C | | FOXL2 (P257T); BCOR (P326T) | 814.0 | |
| VM-006 | F | 3 | Muscle, calf | | | MLL2 (Q2819R) | 588.0 | |
| VM-007 | F | 51 | Muscle, Thigh | | | ATM (G1818V) | 807.0 | |
| VM-008 | F | 20 | Muscle, thigh | | H1047R | | 630.0 | |
| VM-009 | M | 41 | Bone, L5 | | | | 586.2 | This sample presents an epithelioid morphology not typical of VM. |
| VM-010 | F | 52 | Bone, skull | | | AKT3 (R247C) | 594.0 | |
| VM-011 | F | 17 | Subcutaneous, elbow | | | MAP3K1 (H468Q) | 454.0 | |
| VM-012 | M | 64 | Muscle, thigh | | | TGFBR2 (S527T); PHOX2B (247_252del) | 541.0 | |
| VM-013 | M | 20 | Muscle, thigh | | | IRS2 (373_377del) | 484.7 | No mutations detected |
| VM-014 | M | 50 | Muscle, thigh | | E542K | MDC1 (C1599G) | 343.0 | |
| VM-015 | F | 51 | Muscle, thigh | | H1047R | | 523.7 | |
| VM-019 | F | 68 | Post Mediastinum | | | GNAQ (Q209P) | 587.4 | |
| VM-020 | F | 12 | Muscle, calf | L914F | | | 637.3 | |
| VM-021 | F | 18 | Muscle, thigh | L914F | | TERT (441_442del) | 602.1 | |
| VM-022 | F | 34 | Muscle, thigh | | H1047R | | 634.6 | |
| VM-023 | F | 48 | Muscle, thigh | | | MAP2K1 (K57N) | 596.0 | |
| VM-024 | M | 43 | Muscle, thigh | | E542K | | 564.0 | No mutations detected |
| VM-025 | M | 42 | Muscle, deltoid | Y897C; R918H | | | 588.1 | |
| VM-026 | M | 32 | Muscle, thigh | Y897C; R918H | | | 549.7 | |
| VM-027 | F | 37 | Muscle, paraspinal | | | MED12 (Q2113_Q2114insQQHQ) | 533.8 | |
| VM-028 | F | 36 | Muscle, calf | | | | 649.5 | No mutations detected |
| VM-029 | F | 67 | Skin, Face | L914F | | | 451.4 | |
| VM-030 | M | 6 | Skin, Thigh | | E542K | NF1 (C324S) | 560.6 | |
| VM-031 | F | 13 | Skin, finger | L914F | | | 915.5 | |
| VM-032 | F | 3 | Skin, finger | | | MED12 (Q2113_Q2114insQQHQ) | 712.3 | |
| VM-033 | F | 33 | Skin, hand | | C420R | | 691.5 | |
| VM-035 | F | 7 | Lip | L914F | | | 598.4 | |
| VM-036 | M | 25 | Skin, Thorax | L914F | | MDC1 (207_214del) | 778.3 | |
| VM-037 | F | 63 | Skin, finger | | | | 460.0 | No mutations detected |
| VM-042 | M | 54 | Skin, neck, and oral mucosa | L914F | | | 427.0 | |

FIG. 16

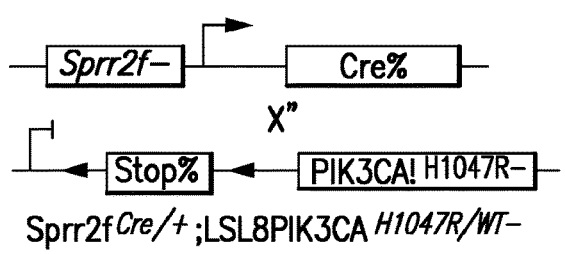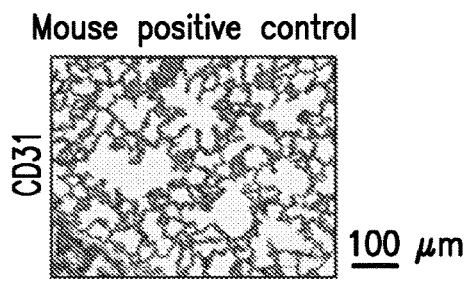
FIG. 17A  FIG. 17B
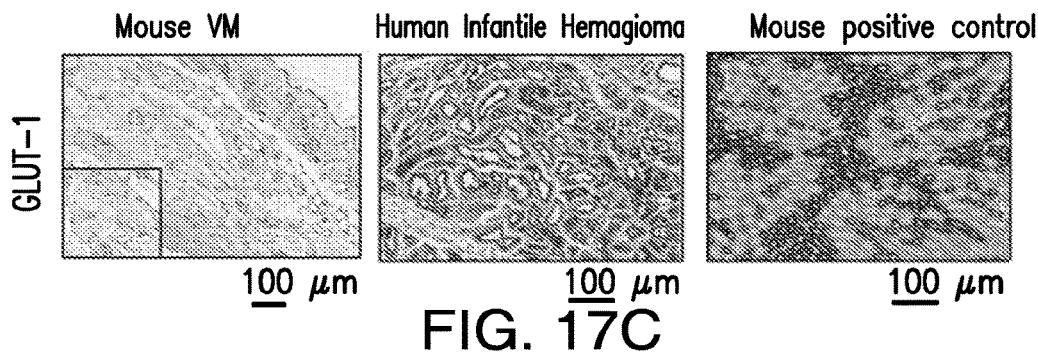
FIG. 17C
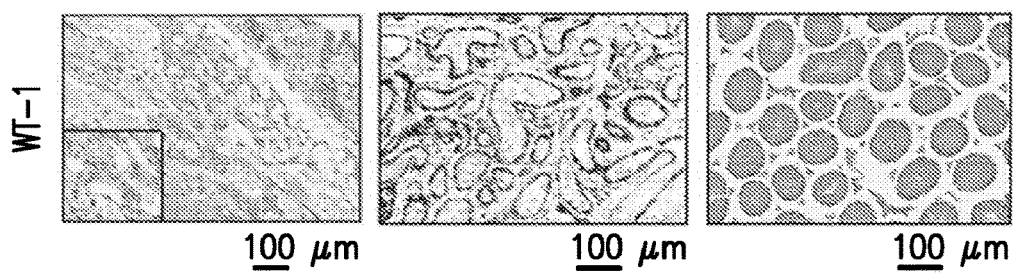
FIG. 17D
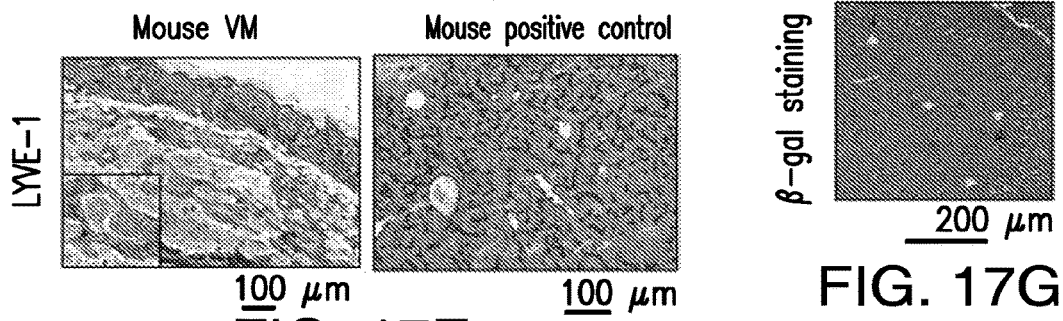
FIG. 17E  FIG. 17G
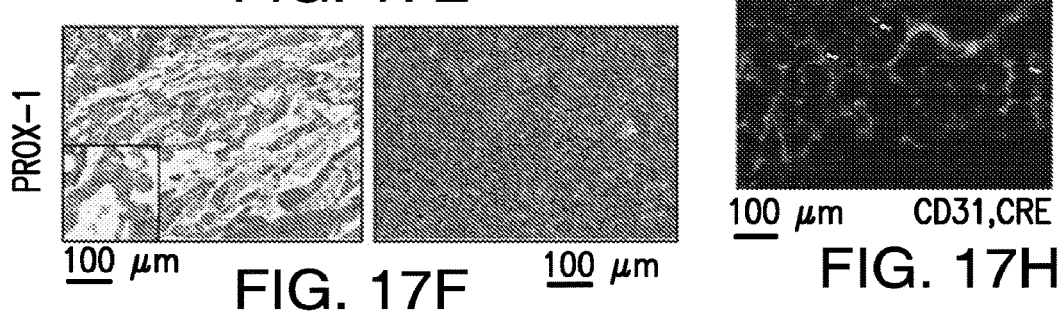
FIG. 17F  FIG. 17H

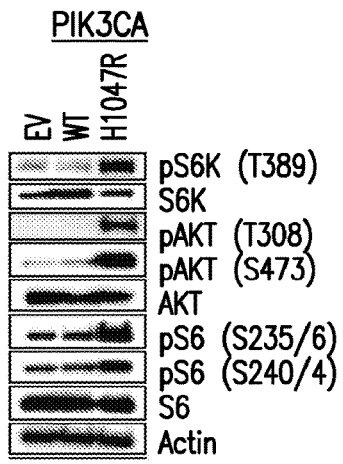
FIG. 19A
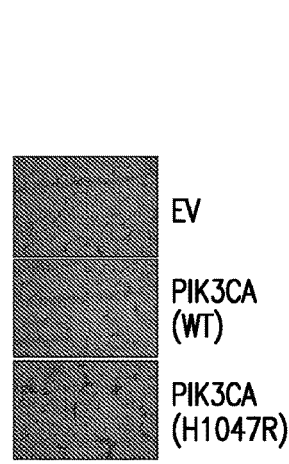
FIG. 19B
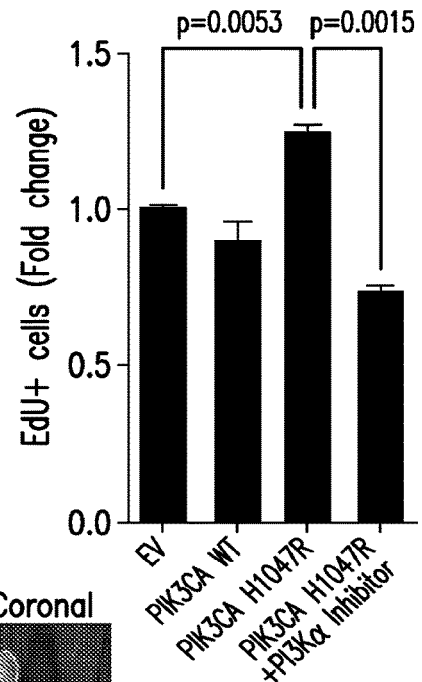
FIG. 19C
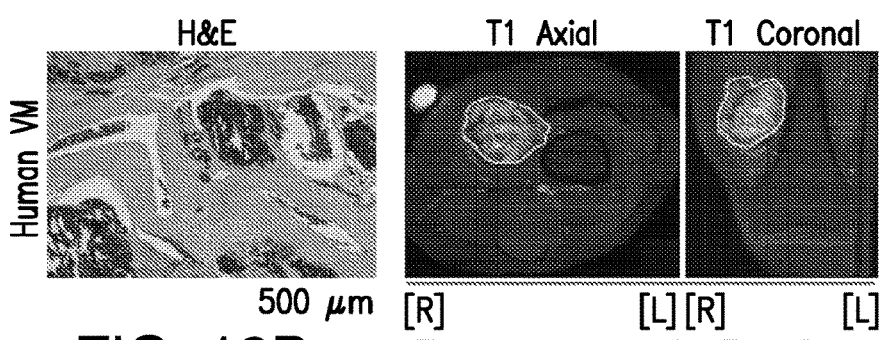
FIG. 19D
FIG. 19E
FIG. 19F
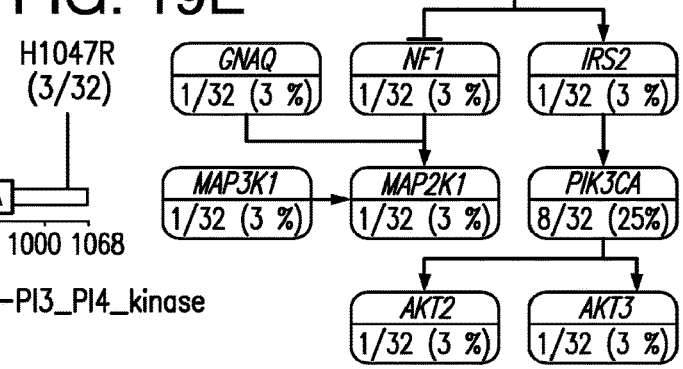
FIG. 19G
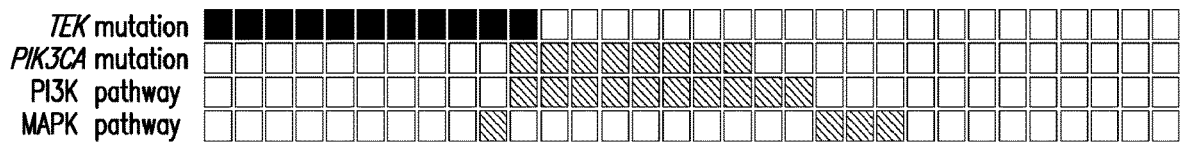
FIG. 19H

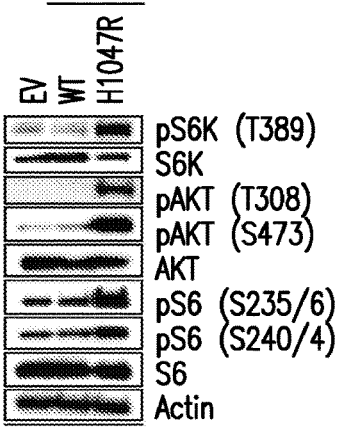
FIG. 20A
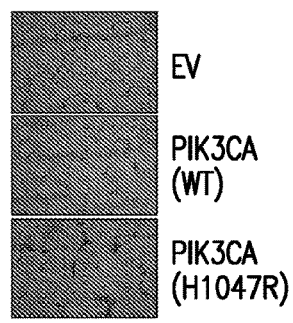
FIG. 20B
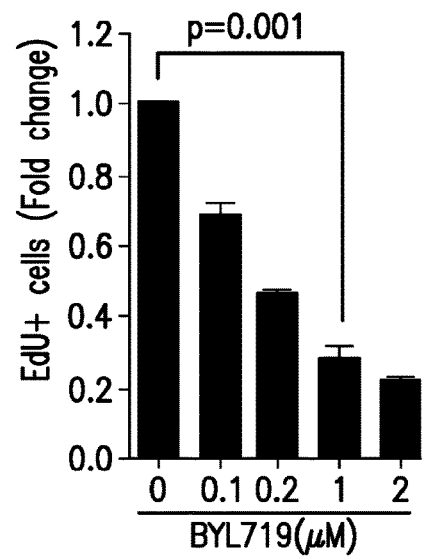
FIG. 20C
FIG. 20D
FIG. 20E

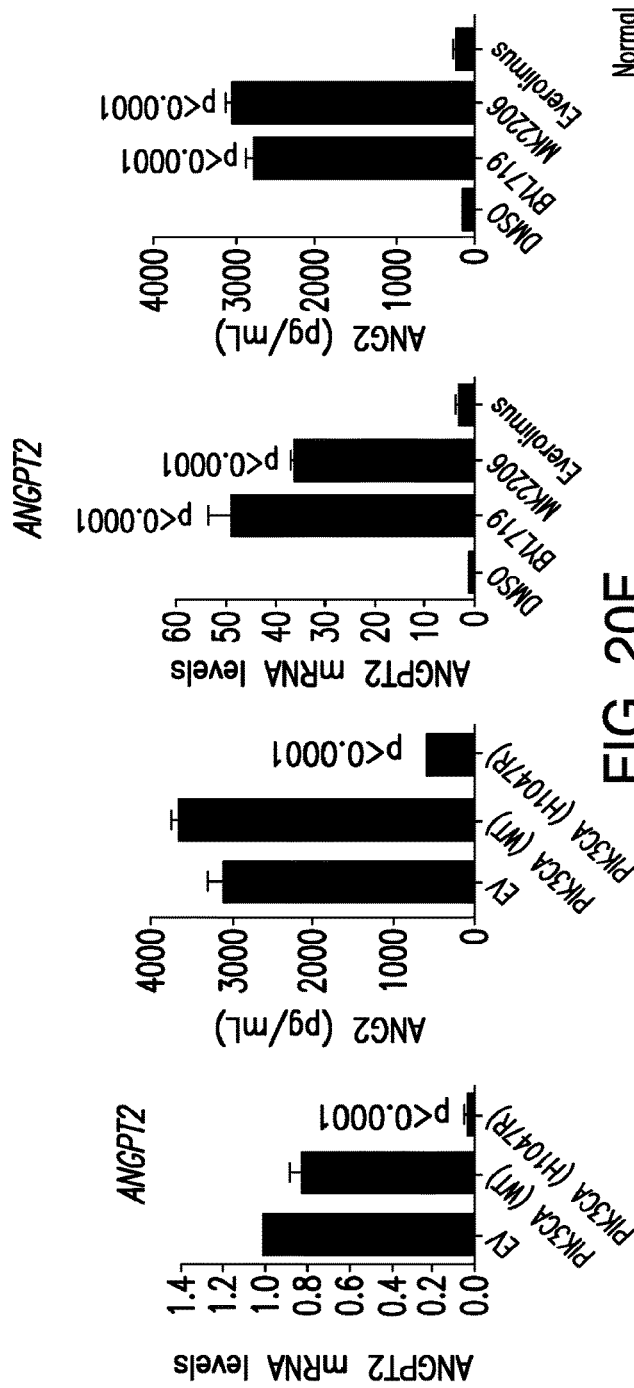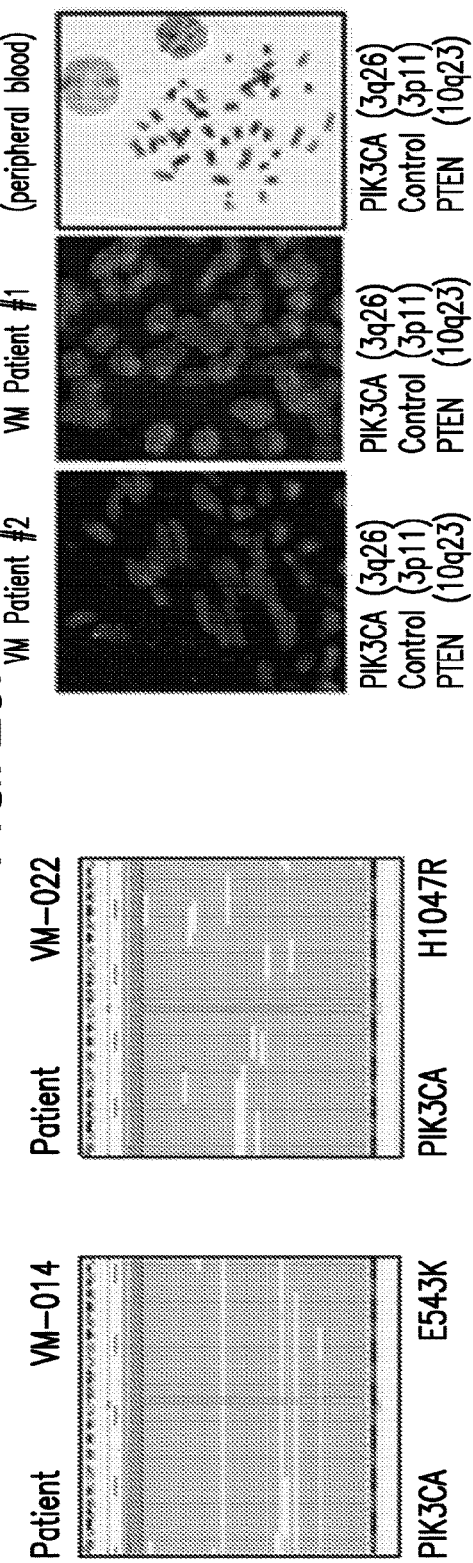
FIG. 20F
FIG. 20G
FIG. 20H

| Patient | Sex | Age | Localization | TEK mutation | Reads (Mutant/Total) | Allele Frequency % | PIK3CA mutation | Reads (Mutant/Total) |
|---|---|---|---|---|---|---|---|---|
| VM-003 | M | 41 | Soft tissue, orbit | | | | | |
| VM-004 | F | 14 | Muscle, buttock | Y897H; R918L | 15/208; 12/187 | 7.21%; 6.03% | I143V | 18/115 |
| VM-005 | M | 72 | Subcutaneous, finger | | | | | |
| VM-006 | F | 3 | Muscle, calf | Y897N; R918C | 47/543; 50/560 | 8.66%; 8.93% | H1047R | 48/889 |
| VM-007 | F | 51 | Muscle, thigh | | | | | |
| VM-008 | F | 20 | Muscle, thigh | | | | | |
| VM-009 | M | 41 | Bone, L5 | | | | | |
| VM-010 | F | 52 | Bone, skull | | | | | |
| VM-011 | F | 17 | Subutaneous, elbow | | | | | |
| VM-012 | M | 64 | Muscle, thigh | | | | E542K | 18/242 |
| VM-013 | M | 20 | Muscle, thigh | | | | H1047R | 20/653 |
| VM-014 | M | 50 | Muscle, thigh | | | | | |
| VM-015 | M | 51 | Muscle, thigh | | | | H1047R | 81/857 |
| VM-019 | F | 68 | Post Mediastinum | | | | | |
| VM-020 | F | 12 | Muscle, calf | L914F | 34/481 | 7.07% | | |
| VM-021 | F | 18 | Muscle, thigh | L914F | 80/567 | 14.11% | | |
| VM-022 | F | 34 | Muscle, thigh | | | | | |
| VM-023 | M | 48 | Muscle, thigh | | | | E542K | 28/442 |
| VM-024 | M | 43 | Muscle, thigh | | | | | |
| VM-025 | M | 42 | Muscle, deltoid | Y897C; R918H | 44/470; 54/442 | 9.36%; 12.22% | | |
| VM-026 | M | 32 | Muscle, thigh | Y897C; R918H | 28/479; 38/465 | 5.85%; 8.17% | | |
| VM-027 | F | 37 | Muscle, paraspinal | | | | | |
| VM-028 | F | 36 | Muscle, calf | | | | | |
| VM-029 | F | 67 | Skin, Face | L914F | 16/217 | 7.37% | E542K | 22/200 |
| VM-030 | M | 6 | Skin, Thigh | | | | | |
| VM-031 | F | 13 | Skin, finger | L914F | 26/621 | 4.19% | | |
| VM-032 | M | 3 | Skin, finger | | | | | |
| VM-033 | F | 33 | Skin, hand | L914F | 16/400 | 4.00% | C420R | 30/311 |
| VM-035 | M | 7 | Lip | L914F | 61/408 | 14.95% | | |
| VM-036 | F | 25 | Skin, Thorax | | | | | |
| VM-037 | F | 63 | Skin, finger | | | | | |
| VM-042 | M | 54 | Skin, neck, and oral mucosa | L914F | 26/256 | 10.16% | | |

FIG. 21

| Allele Frequency % | Other mutations | Sequencing Coverage | Notes |
|---|---|---|---|
| | | 838.0 | No mutations detected |
| 15.65% | AKT2 (K181M) | 243.5 | |
| | FOXL2 (P257T); BCOR (P326T) | 814.0 | |
| | MLL2 (Q2819R) | 588.0 | |
| | ATM (G1818V) | 807.0 | |
| | | 630.0 | |
| 5.40% | AKTC (R247C) | 586.2 | This sample presents an epithelioid morphology not typical of VM. |
| | MAP3K1 (H468Q) | 594.0 | |
| | TGFBR2 (S527I); PHOX2B (247_252del) | 454.0 | |
| | IRS2 (373_377del) | 541.0 | |
| | | 484.7 | No mutations detected |
| 7.74% | MDC1 (C1599G) | 343.0 | |
| 3.10% | | 523.7 | |
| | GNAQ (Q209P) | 587.4 | |
| | | 637.3 | |
| | TERT (441_442del) | 602.1 | |
| 9.45% | MAP2K1 (K57N) | 634.6 | |
| | | 596.0 | No mutations detected |
| | | 564.0 | |
| 6.34% | MED12 (Q2113_Q2114insQQHQ) | 588.1 | |
| | | 549.7 | |
| | | 533.8 | No mutations detected |
| | NF1 (C324S) | 649.5 | |
| 11% | | 451.4 | |
| | MED12 (Q2113_Q2114insQQHQ) | 560.6 | |
| | | 915.5 | |
| 9.60% | MDC1 (207_214del) | 712.3 | |
| | | 691.5 | |
| | | 598.4 | No mutations detected |
| | | 778.3 | |
| | | 460.0 | |
| | | 427.0 | |

FIG. 21 CONTINUED

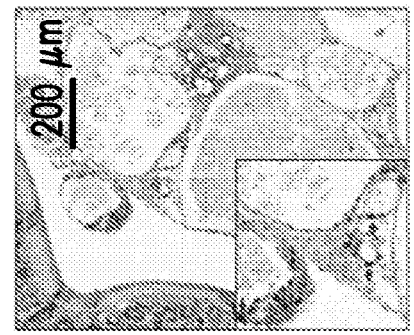
FIG. 22C
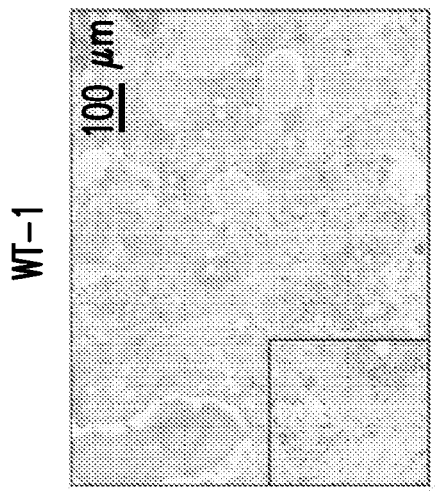
FIG. 22F
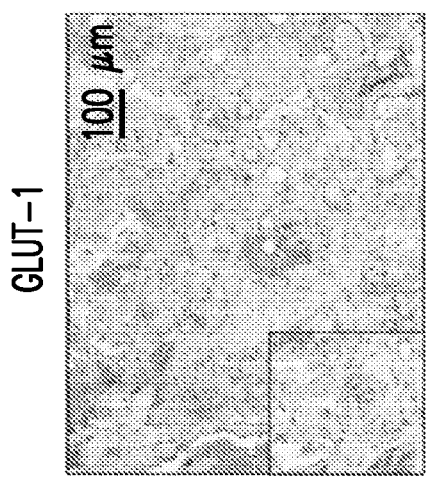
FIG. 22B
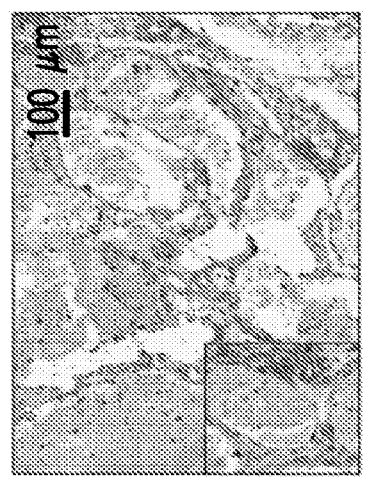
FIG. 22E
FIG. 22A
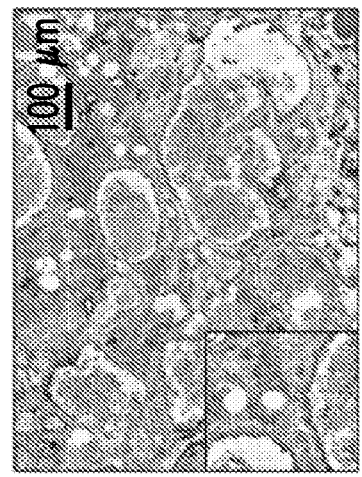
FIG. 22D

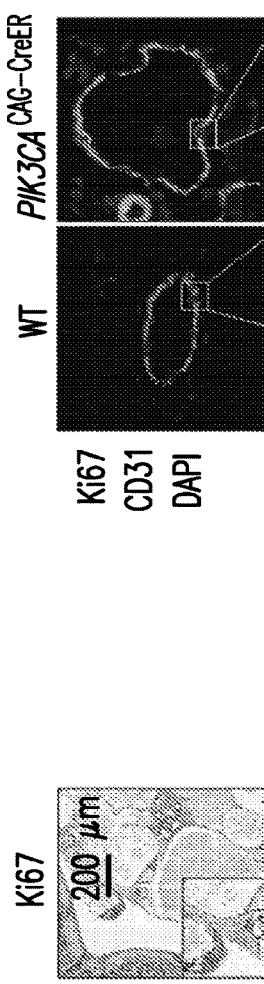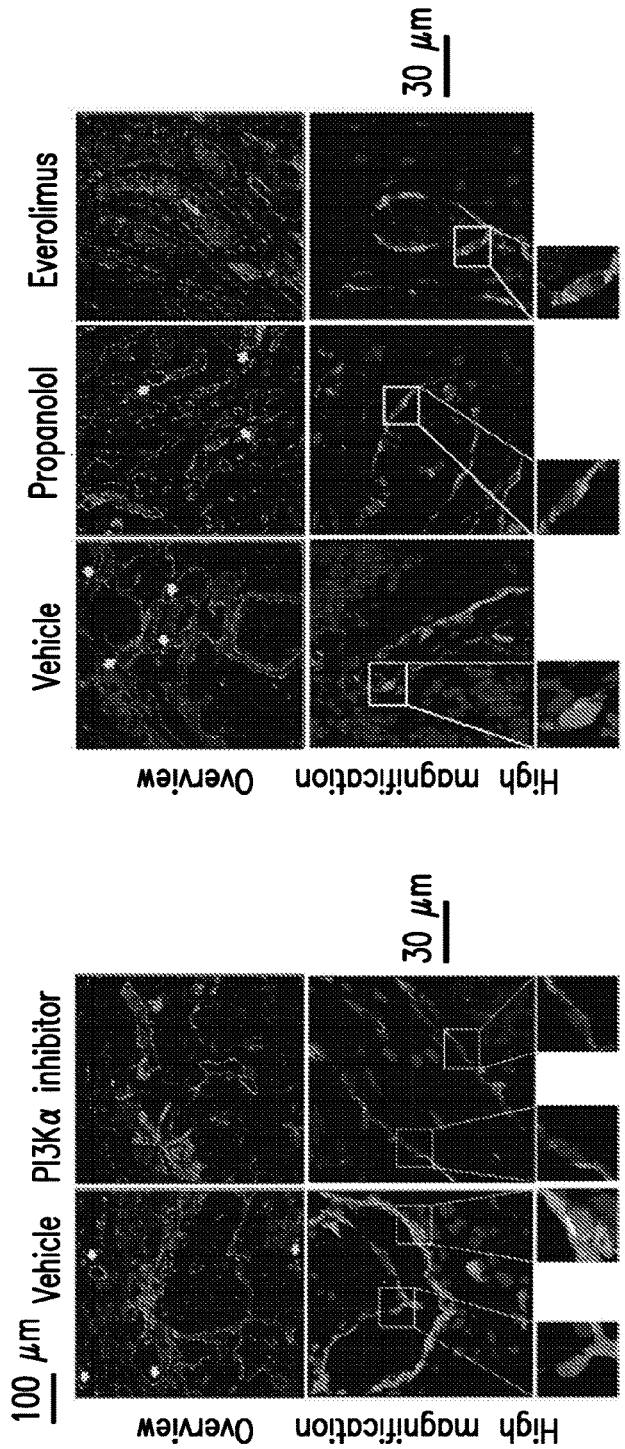
FIG. 25A
FIG. 25B
FIG. 25C
FIG. 25D

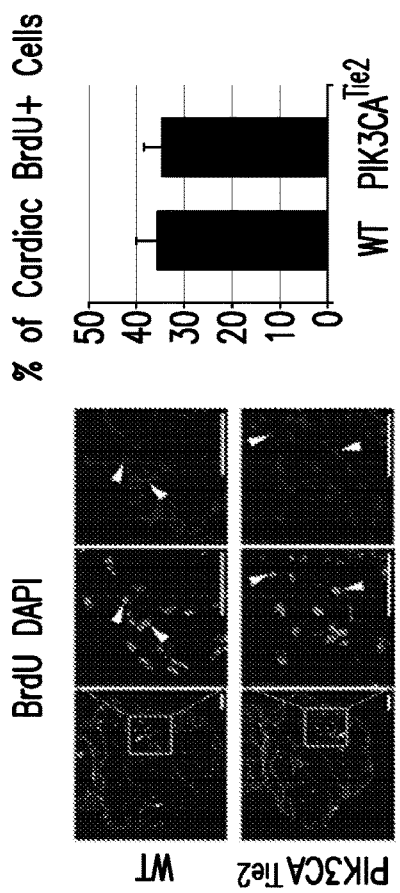
FIG. 28A
FIG. 28B
FIG. 28C
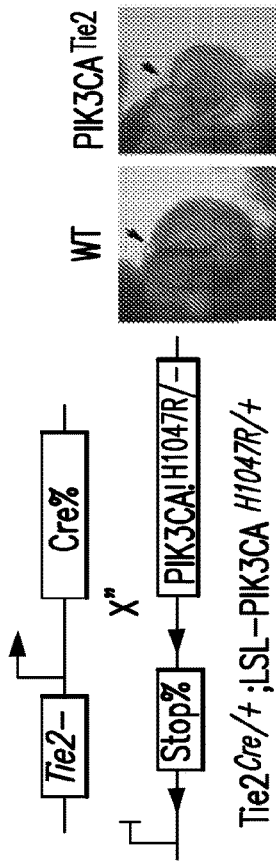
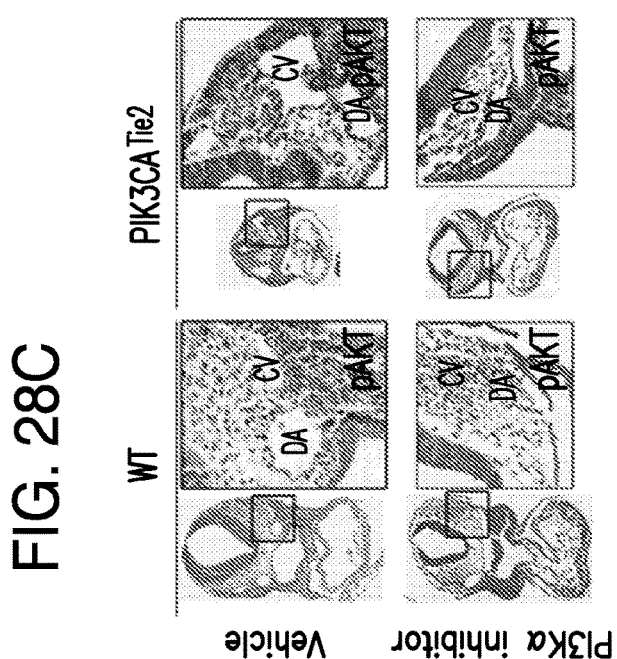
FIG. 28F
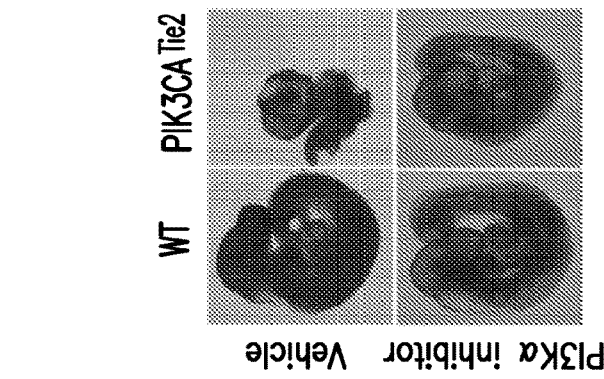
FIG. 28E
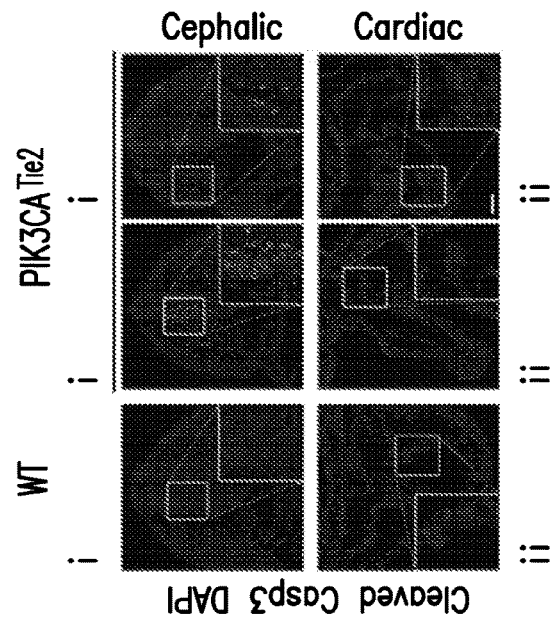
FIG. 28D

| SequenceName | Sequence | Start | Stop |
|---|---|---|---|
| 475_439815_7010 (TEK)_1a_1 | /5Biosg/TTTGTGTGGAAACTGGATGGAAGAGATTTGGGAAGCATGGACTCTTTAGCCAGCTTAGT TCTCTGTGGAGTCAGCTTGCTCCTTCTGGTAAGGTTTGGCTTATTTTTAATTAGTAT | 27109554 | 27109674 |
| 475_439816_7010 (TEK)_2a_1 | /5Biosg/ATTATTGTCTCTCTTCTTTAGGAACTGTGGAAGGTGCCATGGAAGTTGATCTTGAT CAATTCCCTACCTCTTGTATCTGATGTGAAACATCTCTCACTGCATTGCCTCTGGGTGGC | 27157804 | 27157924 |
| 475_439816_7010 (TEK)_2a_2 | /5Biosg/GCCCCCATGAGCCCATCACCATAGGAAGGGACTTTGAAGCCTTAATGAACCAGCACC AGGATCCGCTGAAGTTACTCAAGATGTGACCAGAGAATGGGCTAAAAAAGTTGTTTGGAAGA | 27157924 | 27158044 |
| 475_439816_7010 (TEK)_2a_3 | /5Biosg/GAGAAAAGGCTAGTAAGATCAATGGTGCTTATTTCTGTGAAGGCGAGTTCGAGGAG AGGCAATCAGGATACGAACCATGAAGATGCGTCAACAAGTAACATGCCCCTAAGTTTTGGGC | 27158044 | 27158164 |
| 475_439817_7010 (TEK)_3a_1 | /5Biosg/AAAGCTTCCTTCCTACCAGCAGTCACTTAACTATGACTGTGGACAAGGAGATAACGTGA ACATATCTTCAAAAAGTATTGATTAAAGAAGAAGATGCAGTGATTACAAAAATGGTGAG | 27168488 | 27168608 |
| 475_439818_7010 (TEK)_4a.1_1 | /5Biosg/TGTTTCAGTGTGTGACCTAGGTTCTTCACTCTTCCCTCTACTAGTTCTTCATCCATT CAGTGCCCCCGGCATGAAGTACCTGAAGTACCTACGGAAGTACACCTCTGCCTATGTCAGCCCCA | 27169430 | 27169550 |
| 475_439818_7010 (TEK)_4a.1_2 | /5Biosg/GGATGCTGGAGTGTGGAGTGTACTCGGCCAGTGTATATAGGAGGAGCCACCTTCGGCCTT TTACACCAGGCTGATAGTCGGAGCTGATAGTCGGAGTAAGTCGGACCATTGTGATGGTAGTTG | 27169550 | 27169670 |
| 475_439819_7010 (TEK)_5a.1_1 | /5Biosg/ATGTGTTGAGCGAATGGGCTCTACTCCAGGAGTGCATTGCCCCTTGTTCTTAACAAAGGATG TGAAGCCCAGAAGGTAAGTAGGGGACCTGAATGCAACCATCTCTGTTGTATGAACAATGGTG | 27172559 | 27172679 |
| 475_439819_7010 (TEK)_5a.1_2 | /5Biosg/TCTGCCATGAAGATACTGAGAGATAAAGAGACTTGACTCTGAATCATCTTTTCCTCCTGGTTTATGGAAGGACGT GTGAGAAGGTTTGGCAAGGGGTTGCATATTTGAAGACTGCATCTTTTCCTCCTGGATTAAAAAAGCCATCGTTGCTG | 27172679 | 27172799 |
| 475_439820_7010 (TEK)_6a_1 | /5Biosg/CAAGGGTTTGCAAGGGGTTGCATATTGACTCTGAATCTGAATAAAGGTGCAGTGGTGTCCTGTGCCACAGGGATGCAAGCTGTGAAC TGCACACGTTTGCAATGAAGTGCAACCCTTGGACAGAGGATGTTCTAGCAGTGCAAGCAAGTCTTA | 27173169 | 27173289 |
| 475_439820_7010 (TEK)_6a_2 | /5Biosg/TTAGTTCCTCTCTGGTTTTACGGCCAGTTAATACTGGGATTAACTGGTTTTTGATGTCTCTGTTACACTGAAGGTCT GCCACCCTGGTTTTACGGCCAGTTAATACTGGTAAGCTGTAAGTGTAAGCTAGTTAAGTAAGTCAACAATGGGAGAT | 27173289 | 27173409 |
| 475_439821_7010 (TEK)_7a_1 | /5Biosg/GTGTGATCGCTTCGAAGGATGTCTCTGCTCTCCAGGATGTGTCAGTAGTCACACTGTTCAGGGCCATGTTCAGGGCCATGTTCAGGCAGGGGCTCCAGTGTGA GCCACCCTGGTTTTACGGCCAGTTAATACTGGTAAGCTGTAAGTGTAAGCTAGTTAAGTAAGTCAACAATGGGAGAT | 27180181 | 27180301 |
| 475_439821_7010 (TEK)_7a_2 | /5Biosg/GTGTGATCGCTTCGAAGGATGTCTCTGCTCTCCAGGATGTGTCAGTAGTCACACTGTTCAGGGGCCATGTTCAGCAGGGGCTCCAGTGTGA GAGAGAAGGTAACACTGTTCAGGGGCCATGTTCAGCAGGGGCTCCAGTGTGAACTGAGCT | 27180301 | 27180421 |

FIG. 30

| ID | Sequence | | | |
|---|---|---|---|---|
| 475_439822_7010_(TEK)_8a.1_1 | /5Biosg/CTCTGTTAAATATTAGATTTCACAGTGCTGTTTTCTCCTTCAGGCATACAGAGGATGACCCAAAGATAGTGGATTTGCCAGATCATATAGAAGTAAACAGTGGTAAATTTAATCCCAT | 27183 | 27183 | |
| | | 412 | 532 | |
| 475_439822_7010_(TEK)_8a.1_2 | /5Biosg/TTGCAAAGCTTCTGGCTGGCCGCTACCTACTACTGAAATGAAGAAATGACCCTGGTGAAGCCGGATGGGACAGTGCTCCATGTAAGAGCCATTCTTAATTGCCCTTCTAAAGCATGAGATGCT | 27183 | 27183 | |
| | | 532 | 652 | |
| 475_439823_7010_(TEK)_9a_1 | /5Biosg/TTTATGCCTCCTAGAAGTTTATTTTGTATTGACCTTTCAGCCAAAGACTTTAACCATACGGATCATTCTCAGTAGCCATATTCACCATCCACCGGATCCTCCCCCTGAC | 27185 | 27185 | |
| | | 434 | 554 | |
| 475_439823_7010_(TEK)_9a_2 | /5Biosg/TCAGGAGTTGGGTCTGCAGTGTGAACACAGTGCTGGGATGTGGAAAGCCCTTCAACATTTCTGTTAAAGGTAAGTTCATTTCCCAGAAAAAATTGTATTAGTTCTTCCAAAGCCTTGATGCATATG | 27185 | 27185 | |
| | | 554 | 674 | |
| 475_439824_7010_(TEK)_10a_1 | /5Biosg/AAGCCGAAGGACTAATCTGCCTTCTGAAATAACTTGGACATAACCCAAGAAGCTTCTATACAAACCCGTTAATCACTATGCCCCAAACGTGATTGACACTGGACATTGTGCATCAACATCAGTCTGAGCCTT | 27190 | 27190 | |
| | | 487 | 607 | |
| 475_439824_7010_(TEK)_10a_2 | /5Biosg/ACTTTGGCAACATATTCAAGCTTTGGACAGGATAAGCTTTGGACAGATAGCCAGCTGGGATGTGGTCAGGCTTGGCAACATATTCAAGCTTTGGACAGATAGCCAGCTGGGATGTGG | 27190 | 27190 | |
| | | 607 | 727 | |
| 475_439825_7010_(TEK)_11a.1_1 | /5Biosg/AGGAATGTAAGAAGAATGTAACACTCAACTATTGGAACCTAAGTTTCCTGACGTTTCTCTTCTCAGTGACAAATGAGAGATTGTTACACTCAACTATTGGAACCTGGAAGGCATCCTGGACTCGTCACATGAGCTGTGTGCAACTG | 27192 | 27192 | |
| | | 434 | 554 | |
| 475_439825_7010_(TEK)_11a.1_2 | /5Biosg/GTCCGTCGTGGAGAAGATAATGATTTTCTGGATTCTCCTAGGACTCCCTCCTCCAAGAGGTGCTTCTATCGGTCAGTGGAAGCCAACAGGCATTTATTCATGAGCTGGGTGGGAGGGGAGGAA | 27192 | 27192 | |
| | | 554 | 674 | |
| 475_439826_7010_(TEK)_12a.1_1 | /5Biosg/CCATATATAAAATAGTCAGAAGTGACTTTATGTTGAAGTGGAGAAGGTTCTGTGCAACCAATATTTCCAAGCTAAATCTCCTGCCTAAAAGTCAGTGATCA | 27197 | 27197 | |
| | | 274 | 394 | |
| 475_439826_7010_(TEK)_12a.1_2 | /5Biosg/CTCGGAATATTAAAGTTCCAGGCAACTTGACTTCGGTGCTACTTAACATCCCAGGGAGCAGAATATTAAAGTTCCAGGCAACTGTGCAACTTACATCCCAGGGA | 27197 | 27197 | |
| | | 394 | 514 | |
| 475_439826_7010_(TEK)_12a.1_3 | /5Biosg/GCAGTACGTGGTCCGAGCTAGAGTCAACACCAGGCAAGAATGAAGACCAGCTGACTCAACATATTCGTCAACTGCTTGGACCTTAGTAGCAGTAAATTCATGCGCCCGCTGAGCAA | 27197 | 27197 | |
| | | 514 | 634 | |
| 475_439827_7010_(TEK)_13a_1 | /5Biosg/AAGTGAATCTTCTATTACTATCCGTTACAAGGTTCAAGGCAAGAATGAAGACCAGCCACGTTGATTTCCAACATTACACACTCCTGTGATTTCTTGGACATATTGGATGGCTATTCTA | 27202 | 27202 | |
| | | 787 | 907 | |
| 475_439827_7010_(TEK)_13a_2 | /5Biosg/TTTCTTCTATTACTATCCGTTACAAGGTTCAAGGCAAGAATGAAGACCAGCCACGTTGATGTGAAGATAAAGAATGCCACCACTCAGTATCAGTCAGCTAGAGGGCCTAGAGCCTGAAACAG | 27202 | 27203 | |
| | | 907 | 027 | |
| 475_439827_7010_(TEK)_13a_3 | /5Biosg/CATACCAGGTGGTGACCCTCCCAGAATCTCAAGGTTGCAGAGAACAACATCAAGGGTGAATGGACAAGTTACATAGG | 27203 | 27203 | |
| | | 027 | 147 | |

FIG. 30 CONTINUED

| | | | | |
|---|---|---|---|---|
| 475_439828_7010_(TEK)_14a.1_1 | /5Biosg/TGTAAACTAAACTACCTGCTTCACCTCTGTCTTCCTGCACAGCACCAGCGGACCTCGG AGGGGGAAGATGCTGCTTATAGCCATCCTTGGCTCTGCTGGAATGACCTGCCTGACTGTGC | 27204 866 | 27204 986 |
| 475_439828_7010_(TEK)_14a.1_2 | /5Biosg/TGTTGGCCTTTCTGATCATATTGAAGAGGGCAAATGTGCAAAGGAGAATGGC CCAAGCCTTCCAAAACGTGGTAGTGTCTCATTCCTACTAGCTAATAAGGCAAGTCCAAG | 27204 986 | 27205 106 |
| 475_439829_7010_(TEK)_15a_1 | /5Biosg/AATTATTTTCCAGAGGGAAGAACCAGATCCTCAACTGTGCAGTTCAACTCAGGGACTCTGGCCCT AACAGGAAGGTCAAAAACAACCCAGATCCTACAATTTATCCAGTGCTTGACTGGAATGACA | 27206 565 | 27206 685 |
| 475_439829_7010_(TEK)_15a_2 | /5Biosg/TCAAATTCAAGATGTGATTGGGAGGGCAATTTGGCCAAGTTCTTAAGGCGGCAT CAAGAAGGATGGGTTACGGATGGTGCCATCAAAAGAATGAAAGGTCAGTGGTTGACCA | 27206 685 | 27206 805 |
| 475_439830_7010_(TEK)_16a_1 | /5Biosg/CCAGAATATGCCTCCAAAGATGCTCCAAAGATCACAGGGACTTTGCAGGAGAACTGGAAGTTCTT GTAAACTTGGACACCATCCAAACATCTCTTAGGAGCATGTGAACATCGAGGTAAG | 27209 114 | 27209 234 |
| 475_439831_7010_(TEK)_17a_1 | /5Biosg/CGATGTCTCTCCTTCCCTCCAGGCTACTTGTACCTGGCCATTGAGTACGCGCCCCA TGGAAACCTTCTGGACTTCCTTGCAAGAGCGTGTGCTGGAGAGCAGCATTTGCCA | 27212 680 | 27212 800 |
| 475_439831_7010_(TEK)_17a_2 | /5Biosg/TTGCCAATAGCACGGCGTCACACTGTCCTCCCAGCTCCTCACTTCGCTGCCGA CGTGGCCCGGCATGGACTACTTGAGCCAAAACAGGTTTGTCCGGAGGACTTCGCTTTGG | 27212 800 | 27212 920 |
| 475_439832_7010_(TEK)_18a_1 | /5Biosg/CAGTTTATCCAGATTTGATTGTCCTGTTCTCACTTGTCCGGAGGTCAAGAGGTCCCAGTGCGCTGGCCATCGAG CAAAATAGCAGATTTTGGATTGTCCGGAGGTCAAGAGGTGTATGTGAAAAGACAATGGTA | 27213 478 | 27213 598 |
| 475_439833_7010_(TEK)_19a_1 | /5Biosg/GAAATCTCACTTGTTCTCTGCACACAACAGTGAGTGAGTAACTTCTTATTGCCAAGG TCACTGAATTACAGTGTGTACACAACAGTGAGTGAGTAACTTCTTATTGCCAAGG | 27217 661 | 27217 781 |
| 475_439834_7010_(TEK)_20a_1 | /5Biosg/TGTTTGTCTCTGATTGTTGGTTAGCTGAGAGGATGACTTGTCCCTCCTGCAGATGGTCCTATGGTGTT ACTATGGGAGATTGTTAGCTGAGACTGAGTATCTATGTTATCTACCAGGTGAGACTCTAGGC | 27218 734 | 27218 854 |
| 475_439835_7010_(TEK)_21a_1 | /5Biosg/TTTGTCTCCAGGAGGTATGATCTAATGAGACAATGAGAGAAGCCTTGTGCAGAACTCTACGAGAA GCTGCCCAGGCTACAGACTGAGAAGGAGCCCTGAACTGTGATGATGAGGTAAGTCAGGC | 27220 034 | 27220 154 |
| 475_439836_7010_(TEK)_22a_1 | /5Biosg/GCTTTCGAAGGTAGATCTAATGAGACAATGAGAGCAGAGGAGCGAAAGGTAAGTATTA CATCATTTGCCCAGAGGCTACAGACTGAGAAGGAGCCCTTAAACAGAATGTTAGAGGAGCGAAAGGTAAGTATTA | 27228 193 | 27228 313 |
| 475_439837_7010_(TEK)_23a_1 | /5Biosg/TGAACCATTTCATTCTTCCAGACCTACGTGAATACCACCGCTTTATGAGAAGTTTACTT ATGCAGGAATTGACTGTTCTGCTAGGACGTCTGAAGAAGGCCTAGGACAGAGAACATCTGTATACCCTCT | 27229 133 | 27229 253 |

FIG. 30 CONTINUED

SEQUENCE LISTING

```
<160> NUMBER OF SEQ ID NOS: 40

<210> SEQ ID NO 1
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gtttgtggaa actggatgga gagatttggg gaagcatgga ctctttagcc agcttagttc      60
tctgtggagt cagcttgctc ctttctggta aggtttggct ttatttttt taatttagta     120 t                                                                     121

<210> SEQ ID NO 2
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gattattgtc tctctttcct tttaggaact gtggaaggtg ccatggactt gatcttgatc      60
aattccctac ctcttgtatc tgatgctgaa acatctctca cctgcattgc ctctgggtgg     120
c                                                                     121

<210> SEQ ID NO 3
<211> LENGTH: 121
<212> TYPE: DNA
<213> ORGANISM: Artificial Sequence
<220> FEATURE:
```

```
<223> OTHER INFORMATION: Description of Artificial Sequence: Synthetic
      polynucleotide

<400> SEQUENCE: 3
ggcccccatg agcccatcac cataggaagg gactttgaag ccttaatgaa ccagcaccag    60
gatccgctgg aagttactca agatgtgacc agagaatggg ctaaaaaagt tgtttggaag   120
a                                                                  121

<210> SEQ ID NO 4
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
ggagaaaagg ctagtaagat caatggtgct tatttctgtg aagggcgagt tcgaggagag    60
gcaatcagga tacgaaccat gaagatgcgt caacaaggta acatgcccct aagttttggg   120
c                                                                  121

<210> SEQ ID NO 5
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gaaagcttcc ttcctaccag ctactttaac tatgactgtg gacaagggag ataacgtgaa    60
catatctttc aaaaaggtat tgattaaaga agaagatgca gtgatttaca aaaatggtga   120
g                                                                  121

<210> SEQ ID NO 6
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gtgtttcagt gtgacctacg gttcttcact cttccctctt actaggttcc ttcatccatt    60
cagtgccccg gcatgaagta cctgatattc tagaagtaca cctgcctcat gctcagcccc   120
a                                                                  121

<210> SEQ ID NO 7
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gggatgctgg agtgtactcg gccaggtata taggaggaaa cctcttcacc tcggccttca    60
ccaggctgat agtccggagt aagtgatgga gaggccacca tttgtgatgg tgtagttgtt   120
a                                                                  121
```

<210> SEQ ID NO 8
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gatgtgttga gcgaatgcgc tctactcacc acagccttgt tttccttaac aaaaggatgt    60
gaagcccaga agtggggacc tgaatgcaac catctctgta ctgcttgtat gaacaatggt   120
g                                                                  121

<210> SEQ ID NO 9
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gtctgccatg aagatactgg agaatgcatt tgccctcctg ggtttatggg aaggacgtgt    60
gagaagggta agtaaagaga cttgataagt aagctgtgga tttaaaaagc catcgttgct   120
g                                                                  121

<210> SEQ ID NO 10
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gcaaggggtt gcatatttga ctctgaatca tcttttcttt tcctcccaaa gcttgtgaac    60
tgcacacgtt tggcagaact tgtaaagaaa ggtgcagtgg acaagaggga tgcaagtctt   120
a                                                                  121

<210> SEQ ID NO 11
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gtgtgttctg tctccctgac ccctatgggt gttcctgtgc cacaggctgg aagggtctgc    60
agtgcaatga aggtatgcac caatcacacc cttggacaga ggatgttcta gcaggtatat   120
a                                                                  121

<210> SEQ ID NO 12
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
gttagttttcc tctcttcccc tggattaata ctggttttt dgatgtctctg tttacagcat    60 gccaccctgg tttttacggg ccagattgta agcttaggtg cagctgcaac aatggggaga   120
t                                                                   121

<210> SEQ ID NO 13
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
ggtgtgatcg cttccaagga tgtctctgct ctccaggatg caggggctc cagtgtgaga     60 gagaaggtaa agcaaggtaa cactgtagtc agggccatgt tcagcatgtc tgaactgagc  120
t                                                                   121

<210> SEQ ID NO 14
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
gctctgttaa atattagatt tcacagtgct gttttcttcc ttcaggcata cagaggatga    60
ccccaaagat agtggatttg ccagatcata tagaagtaaa cagtggtaaa tttaatccca  120
t                                                                   121

<210> SEQ ID NO 15
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gttgcaaagc ttctggctgg ccgctaccta ctaatgaaga aatgaccctg gtgaagccgg    60
atgggacagt gctccatgta agagccattc ttaatttgcc cttcttaaag catgagatgc  120
t                                                                   121

<210> SEQ ID NO 16
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
gtttatgcct ccctagaagt tttattttt ttgtatttga cctttcagc caaaagactt     60 taaccatacg gatcatttct cagtagccat attccaccatc caccggatcc tcccccctga 120
c                                                                   121

<210> SEQ ID NO 17
<211> LENGTH: 121
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 17
gtcaggagtt tgggtctgca gtgtgaacac agtggctggg atggtggaaa agcccttcaa      60
catttctgtt aaaggtaagt tcatttccca gaaaaaggga ttgtgtcctt gatgcattat    120
g                                                                    121

<210> SEQ ID NO 18
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gaagccgaag gactaatctg ccttctgaaa ttgtatttag ttcttccaaa gcccctgaat      60
gccccaaacg tgattgacac tggacataac tttgctgtca tcaacatcag ctctgagcct    120
t                                                                    121

<210> SEQ ID NO 19
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
gactttgggg atggaccaat caaatccaag aagcttctat acaaacccgt taatcactat      60
gaggcttggc aacatattca aggtaagctt tggacaggat agatgccagc tggggatgtg    120
g                                                                    121

<210> SEQ ID NO 20
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gaggaatgta agagaatgcc aacttaagtt tcctggacgt tttctcttct cagtgacaaa      60
tgagattgtt acactcaact atttggaacc tcggacagaa tatgaactct gtgtgcaact    120
g                                                                    121

<210> SEQ ID NO 21
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
ggtccgtcgt ggagagggtg gggaagggca tcctggacct gtgagacgct tcacaacagc      60
ttctatcggt cagtggaagc caacaggcat ttattcatga gctgggtggg aggggagga    120 a                                                                    121
```

<210> SEQ ID NO 22
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gccatatata aaaataatga tttttctgga ttctcctagg actccctcct ccaagaggtc        60
taaatctcct gcctaaaagt cagaccactc taaatttgac ctggcaacca atatttccaa      120
g                                                                      121

<210> SEQ ID NO 23
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
gctcggaaga tgacttttat gttgaagtgg agagaaggtc tgtgcaaaaa agtgatcagc        60
agaatattaa agttccaggc aacttgactt cggtgctact taacaactta catcccaggg      120
a                                                                      121

<210> SEQ ID NO 24
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
ggcagtacgt ggtccgagct agagtcaaca ccaaggccca gggggaatgg agtgaagatc        60
tcactgcttg daccctagt gacagtaagt aattcatgct gctccagcct catctgagca      120
a                                                                      121

<210> SEQ ID NO 25
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
gaagtgaatc tttttctttt ttaatttcta gttcttcctc ctcaaccaga aaacatcaag        60
atttccaaca ttacacactc ctcagctgtg atttcttgga caatattgga tggctattct      120
a                                                                      121

<210> SEQ ID NO 26
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
gtttcttcta ttactatccg ttacaaggtt caaggcaaga atgaagacca gcacgttgat    60
gtgaagataa agaatgccac catcactcag tatcagctca agggcctaga gcctgaaaca   120
g                                                                  121
```

<210> SEQ ID NO 27
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
gcataccagg tggacatttt tgcagagaac aacatagggt caagcaaccc agccttttct    60
catgaactgg tgaccctccc agaatctcaa ggttggttga atggacaagt atttacatag   120
g                                                                  121
```

<210> SEQ ID NO 28
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
gtgtaaacta aactacctgc ttcacctctg tcttcctgca cagcaccagc ggacctcgga    60 gggggaaga tgctgcttat agccatcctt ggctctgctg aatgacctg cctgactgtg    120 c                                                                  121
```

<210> SEQ ID NO 29
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
gtgttggcct ttctgatcat attgcaattg aagagggcaa atgtgcaaag gagaatggcc    60
caagccttcc aaaacgtggt agtgtctcat cttcctacta gctaataagg gcaagtccaa   120
g                                                                  121
```

<210> SEQ ID NO 30
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
gaattatttt tccagaggga agaaccagct gtgcagttca actcagggac tctggcccta    60
aacaggaagg tcaaaaacaa cccagatcct acaatttatc cagtgcttga ctggaatgac   120
a                                                                  121
```

<210> SEQ ID NO 31
<211> LENGTH: 121
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 31
gtcaaatttc aagatgtgat tggggagggc aattttggcc aagttcttaa ggcgcgcatc    60
aagaaggatg ggttacggat ggatgctgcc atcaaaagaa tgaaaggtca gtggttgacc   120
a                                                                  121

<210> SEQ ID NO 32
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gccagaatat gcctccaaag atgatcacag ggactttgca ggagaactgg aagttctttg    60
taaacttgga caccatccaa acatcatcaa tctcttagga gcatgtgaac atcgaggtaa   120
g                                                                  121

<210> SEQ ID NO 33
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
gcgatgctct cttccttccc tccaggctac ttgtacctgg ccattgagta cgcgccccat    60
ggaaaccttc tggacttcct tcgcaagagc cgtgtgctgg agacggaccc agcatttgcc   120
a                                                                  121

<210> SEQ ID NO 34
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
gttgccaata gcaccgcgtc cacactgtcc tcccagcagc tccttcactt cgctgccgac    60
gtggcccggg gcatggacta cttgagccaa aaacaggttt gtccggagga cttcgctttg   120
g                                                                  121

<210> SEQ ID NO 35
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
gcagtttatc cacagggatc tggctgccag aaacatttta gttggtgaaa actatgtggc    60
aaaaatagca gattttggat tgtcccgagg tcaagaggtg tatgtgaaaa agacaatggt   120

<210> SEQ ID NO 36
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
ggaaatctca ctttgttctc tccagggaag gctcccagtg cgctggatgg ccatcgagtc    60
actgaattac agtgtgtaca caaccaacag tgatgtgtga gtaaacttct tattgccaag   120
g                                                                  121

<210> SEQ ID NO 37
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
gtgtttgctg attgttggtt tcacacttgt ccctcctgca gatggtccta tggtgtgtta    60
ctatgggaga ttgttagctt aggtgagtat ctatgtttat ctaccaggtg agactctagg   120
c                                                                  121

<210> SEQ ID NO 38
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
gtttgtcttc caggaggcac accctactgc gggatgactt gtgcagaact ctacgagaag    60
ctgccccagg gctacagact ggagaagccc ctgaactgtg atgatgaggt gtaagtcagg   120
c                                                                  121

<210> SEQ ID NO 39
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
ggctttcgaa ggtatgatct aatgagacaa tgctggcggg agaagcctta tgagaggcca    60
tcatttgccc agatattggt gtccttaaac agaatgttag aggagcgaaa ggtaagtatt   120
a                                                                  121

<210> SEQ ID NO 40
<211> LENGTH: 121
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 40
gtgaaccatt ttcattcttc cagacctacg tgaataccac gctttatgag aagtttactt      60
atgcaggaat tgactgttct gctgaagaag cggcctagga cagaacatct gtataccctc     120
t                                                                     121
```

USE OF PHOSPHOINOSITIDE 3-KINASE INHIBITORS FOR TREATMENT OF VASCULAR MALFORMATIONS

CROSS REFERENCE TO RELATED APPLICATIONS

This application is a Continuation of International Patent Application No. PCT/US16/32779 filed May 16, 2016, which claims priority to U.S. Provisional Application No. 62/162,534 filed May 15, 2015; U.S. Provisional Application No. 62/265,641 filed Dec. 10, 2015; and U.S. Provisional Application No. 62/313,476 filed Mar. 25, 2016, priority to each of which is claimed, and the contents of each of which are incorporated by reference in their entireties.

SEQUENCE LISTING

The specification further incorporates by reference the Sequence Listing submitted herewith via EFS on Nov. 14, 2017. Pursuant to 37 C.F.R. § 1.52(e)(5), the Sequence Listing text file, identified as 0727340637SEQ.txt, is 16,048 bytes and was created on Nov. 14, 2017. The entire contents of the Sequence Listing are hereby incorporated by reference. The Sequence Listing does not extend beyond the scope of the specification and thus does not contain new matter.

1. INTRODUCTION

The present invention relates to methods of treating a vascular malformation in a subject comprising administering, to the subject, an effective amount of an agent that inhibits phosphoinositide 3-kinase ("PI3K").

2. BACKGROUND OF THE INVENTION

2.1 Vascular Malformations

Vascular malformations are clinically challenging because current classifications only take into account the patient outcome and the histological characterization. In fact, many efforts are focused on trying to differentiate these lesions from vascular tumors. While vascular benign tumors, such as Infantile Hemangioma, spontaneously regress and can be treated with propranolol, vascular malformations continue to grow for many years. Venous malformations are of great interest due to current lack of treatment and prognosis. Moreover, pathogenesis of these lesions remain obscure.

2.2 Phosphoinositide 3-Kinase

The development of high throughput sequencing techniques has uncovered the most prevalent genomic alterations in human tumors. Among the genes involved, PIK3CA is frequently mutated or amplified in solid tumors. The PIK3CA locus encodes for the alpha isoform of phosphoinositide 3-kinase ("PI3K"), p110α, the catalytic subunit of the PI3K holoenzyme. Upon mitogenic stimulation or oncogenic mutations, PI3K is activated and generates the accumulation of phosphatidylinositol 3,4,5-trisphosphate (PIP3) in the inner cell membrane, which recruits and activates proteins that transduce downstream signaling and promote cell growth, proliferation, and survival. Although multiple studies have dissected the biology of the PI3K pathway and characterized disease-relevant mutations, there are relatively few studies focused on the in vivo oncogenicity of the PIK3CA oncogene.

3. SUMMARY OF THE INVENTION

The present invention relates to methods of treating a vascular malformation in a subject comprising administering, to the subject, an effective amount of an agent that inhibits phosphoinositide 3-kinase ("PI3K"). It is based, at least in part, on the discoveries that activating mutations of PIK3CA are associated with development of vascular malformations in human subjects and in an animal model, and that, in the latter, treatment with a PI3K inhibitor reduces the vascular abnormalities observed.

In certain non-limiting embodiments, the present invention provides for a method of treating a vascular malformation in a subject, where the subject has a gain-of-function mutation in the PI3K/AKT pathway, comprising administering, to the subject, an effective amount of an agent that inhibits the PI3K/AKT pathway.

In certain embodiments, the gain-of-function mutation in the PI3K/AKT pathway is an activating mutation in PIK3CA, for example, a mutation at amino acid 88, 542, 545, 1047, 420, and/or 143 of the PIK3CA amino acid sequence.

In certain embodiments, the activation mutation is selected from the group consisting of R88Q, E542K, E545K, E545Q, H1047L, H1047Q, H1047R, C420R, and/or I143V, or combinations thereof.

In certain embodiments, the agent that inhibits PI3K is an agent that selectively inhibits the alpha isoform (p110α) of PI3K, for example, BYL719 (Alpelisib), BAY80-6946 (Copanlisib), CH5132799, GDC-0941 (Pictilisib), A66, PIK 90, and/or HS-173, or combinations thereof.

In certain embodiments, the agent that inhibits the PI3K/AKT pathway is selected from the group consisting of GDC-0032, BKM-120, BEZ235, GNE-317, PI-103, PIK-75, BGT226, GSK1059615, PF-04691502, CNIO-PI3Ki, GSK2126558, XL147, PKI-402, GDC0980, BGT226, GSK1059615, PF-04691502, and/or MK2206, or combinations thereof.

In certain embodiments, the gain-of-function in the PI3K/AKT pathway is a mutation in one or more of AKT1, AKT2, AKT3, and/or IRS2.

In certain embodiments, the vascular malformation is a venous malformation. In certain embodiments, the subject has multiple vascular malformations. In certain embodiments, the subject suffers from at least one vascular malformation, the surgical treatment of which would be high-risk. In certain embodiments, the vascular malformation is in the brain. In certain embodiments, the vascular malformation is located within the skin.

In certain embodiments, the subject suffers from a malignancy. In certain embodiments, the subject is not known to suffer from a malignancy.

In certain embodiments, the subject suffers from a multisystem genetic disorder. In certain embodiments, the subject is not known to suffer from a multisystem genetic disorder.

In certain embodiments, the agent that inhibits the PI3K/AKT pathway is administered systemically or locally.

In certain embodiments, the agent that inhibits the PI3K/AKT pathway is administered topically.

In certain embodiments, the agent that inhibits the PI3K/AKT pathway is administered parenterally.

In certain embodiments, the agent that inhibits the PI3K/AKT pathway is administered orally.

In certain non-limiting embodiments, the present invention provides for a method of treating a vascular malformation in a subject, where the subject has a gain-of-function mutation in endothelial-specific tyrosine kinase receptor TEK (TIE2), comprising administering, to the subject, an effective amount of an agent that inhibits the PI3K/AKT pathway.

In certain non-limiting embodiments, the present invention provides for a method of treating a vascular malformation in a subject comprising (i) determining whether the subject has a gain-of-function mutation in the PI3K/AKT pathway; and (ii) where the subject has a gain-of-function mutation in the PI3K/AKT pathway, treating the subject with an agent that inhibits the PI3K/AKT pathway, or, where the subject does not have an activating mutation of PIK3CA, treating with another modality such as surgery, embolization, or occlusion.

In certain non-limiting embodiments, the present invention provides for a method of treating a vascular malformation in a subject comprising (i) determining whether the subject has a gain-of-function mutation in endothelial-specific tyrosine kinase receptor TEK (TIE2); and (ii) where the subject has a gain-of-function mutation in TIE2, treating the subject with an agent that inhibits the PI3K/AKT pathway, or, where the subject does not have an activating mutation of PIK3CA, treating with another modality such as surgery, embolization, or occlusion.

In certain non-limiting embodiments, the methods of the present invention further comprise treating the subject with an amount of a second inhibitor of the PI3K/AKT pathway in an amount that, together with the first inhibitor, effectively treats the vascular malformation.

In certain embodiments, the present invention provides for an inhibitor of the PI3K/AKT pathway, for use in treating a vascular malformation in a subject, as described herein.

In certain embodiments, the present invention provides for a kit comprising an inhibitor of the PI3K/AKT pathway (e.g., a PI3K inhibitor). In certain embodiments, a kit can comprise a container, such as a vial, that includes a pharmaceutical formulation comprising an inhibitor of the PI3K/Akt pathway (e.g., a PI3K inhibitor) in a pharmaceutically acceptable carrier.

4. BRIEF DESCRIPTION OF THE FIGURES

FIGS. 1A-1F. (A) Construction of mice that express the PIK3CA$^{H1047R}$ mutation in all the cells of the body in the presence of tamoxifen. (B) Growth of lesions can be inhibited by PI3Kα inhibitor. (C)-(F) Histological staining of lesions for Ki67, GLUT-1, WT-1 and LYVE-1, respectively.

FIGS. 2A-2I. (A) Development of venous malformations (VM). (B) Histology of VM. (C) CD31 expression in lesion. (D) pAKT in lesion. (E) Prussian blue staining in lesion. (F) Histology of VM with expanded view. (G) Corresponding CD31 expression. (H) Corresponding Prussian blue staining. (I) BrdU incorporation.

FIGS. 3A-3F. (A) Construction of UBC-CreER mice that express the PIK3CA$^{H1047R}$ mutation in all the cells of the body. (B, C) Histology demonstrated by hematoxylin-eosin staining. (D) Prussian blue staining. (E) GLUT-1 staining (negative). (F) WT-1 staining (negative).

FIGS. 4A-4F. (A) Construction of mice expressing PIK3CA$^{H1047R}$ under the control of the Tie2 promoter, which is specific for endothelial cells. (B) Comparison of whole embryos, wild type (WT) versus mutant. (C) Comparison of WT versus mutant embryos in (top) coronal sections and (bottom) showing intersomitic vessels. (D) Vascular precursors in WT versus mutant. (E) Whole embryos, wild type and PI3K-inhibitor treated mutant. (F) Comparison of WT versus PI3K-inhibitor treated mutant embryos in (top) coronal sections and (bottom) showing intersomitic vessels.

FIGS. 5A-5D. PI3K-pathway mutations in a group of human subjects having venous malformations. (A) Radiographic image of subject having VM. (B) Histology of human VM. (C) Incidence of PI3K pathway mutations in human subjects with VM. (D) PI3K pathway-related molecules.

FIGS. 6A-6F. PIK3CA$^{Sprr2fCRE}$ mice develop spinal vascular malformations. (A) Hind limb paresis observed in the PIK3CA$^{Sprr2fCRE}$ mice. (B) Gross and detailed histology of the spinal cord of the PIK3CA$^{Sprr2fCRE}$ mice. Arrows indicate the multiple focal hemorrhages. (C) microCT scan of a WT mouse compared to PIK3CA$^{Sprr2fCRE}$ mice littermates showing an early and an advanced phenotype. Arrows indicate the rheological slow flow lesions observed in the spinal cord. (D) H&E histology from skin VM. Dashed line delimits the vascular malformation (lower) from the epidermis (upper). (E) CD31 IHC of the skin VM lesions and (F) Prussian blue staining. Dashed line delimits the vascular malformation (lower) from the epidermis (upper).

FIGS. 7A-7G. PIK3CA mutations cause sporadic VM in humans. (A) Western blot of human skin EC infected with empty vector (EV), PIK3CA WT, and H1047R mutation. Cells were serum-starved overnight before lysis. (B) Representative images from the tube formation assay of EC serum-starved overnight. (C) EdU incorporation assay quantification of EC serum-starved overnight and labeled using EdU for 4 hours. (D) H&E staining highlighting the morphology of the human VM sequenced in this study. (E) Representative MRI scan from a representative intramuscular sporadic VM patient sequenced in this study. (F) TIE2, PI3K, and MAPK pathway gene components found to be mutated in sporadic VM by MSK-IMPACT in this study. In red activating mutations and blue inactivating mutations are indicated. Dark red designates mutations found in more than 20% of the patients. Unknown mutations are shown in grey. (G) Summary of the somatic mutations found in TEK and PIK3CA in the VM patient cohort that yielded mutations using MSK-IMPACT. In blue are indicated the activating mutations in TEK, and in red the activating mutations in PIK3CA. In green are represented the alterations affecting genes involved in the PI3K or MAPK pathway.

FIGS. 8A-8J. Ubiquitous expression of PIK3CA$^{H1047R}$ induces VM. (A) Disease-free survival plot of PIK3CA$^{CAG-CreER}$ and PIK3CA$^{WT}$ littermates on tamoxifen diet assessed by the appearance of cutaneous VM. Dotted line represents the time where tamoxifen diet was administered. (B) H&E staining of VM developed in the skin of PIK3CA$^{CAG-CreER}$ mice. (C) CD31 IHC. (D) phosphorylated AKT (S473) IHC (arrows indicate lining EC that show positivity for the staining), and (E) Prussian blue staining of the PIK3CA$^{CAG-CreER}$ mice skin lesions. (F) H&E representation of mesenteric VM harvested during necropsy and amplification to highlight the blood pools observed in the histologic preparations. (G) CD31 and (H) Prussian blue positivity of the VM from "F". (I) Ki67 staining of the mesenteric VM. Arrows indicate positive nuclei within the lining EC layer. (J) BrdU incorporation (red) in PIK3CA$^{CAG-CreER}$ VM compared to normal blood vessels. CD31 (green) and DAPI (blue) show endothelial cells and nuclei, respectively.

FIGS. 9A-9F. PI3K inhibitors are effective for the treatment of VM. (A) Schematic representation and images from the allotransplantation assays described. (B) VM volume measured from PIK3CA$^{CAG-CreER}$ VM-derived allografts treated with vehicle or PI3Kα inhibitor during one week (BYL719-50 mg×kg$^{-1}$; daily p.o.). (C) Quantification of BrdU incorporation and cleaved caspase 3 in CD31-positive cells from "B". (D) VM volume measured from PIK3CA$^{CAG-CreER}$ VM-derived allografts treated with vehicle, Everolimus (10 mg×kg$^{-1}$; daily p.o.), or propranolol (40 mg×kg$^{-1}$; daily p.o.) during one week. (E) Quantification of BrdU incorporation and cleaved caspase 3 in CD31-positive cells from "D". (F) VM volume from PIK3CA$^{CAG-CreER}$ VM-derived allografts treated topically with BYL719 1% (w/w) using two different formulations during several weeks.

FIGS. 10A-10E. PIK3CA$^{H1047R}$ impairs embryonic angiogenesis. (A) Embryonic phenotype at E10 of PIK3CA$^{WT}$ (left) and PIK3CA$^{Tie2-Cre}$ (right) littermates. (B) CD31 staining of coronal sections from PIK3CA$^{WT}$ and PIK3CA$^{Tie2-Cre}$ embryos at E9.5. Arrows indicate blood vessel enlargement defects in the meningeal (upper panel) and the intersomitic vessels (lower panel). (C) Whole embryo CD31 staining from PIK3CA$^{WT}$ and PIK3CA$^{Tie2-Cre}$ mice from females treated with vehicle or PI3Kα inhibitor (BYL719-50 mg×kg$^{-1}$; daily p.o.; 48, 24, and 2 hours before embryos are harvested). (D) Detailed view of the cephalic and intersomitic blood vessels from "C". Arrow indicates defects in the meningeal (upper panel) and the intersomitic vessels (lower panel). (E) CD31 coronal sections from embryos from "D". CV (Cardinal vein); DA (Dorsal aorta).

FIGS. 11A-11H. Histologic characterization of PIK3CA$^{Sprr2f-Cre}$ mice (A) Schematic representation of the genetic strategy used to generate PIK3CA$^{Sprr2fCRE}$ mice. (B) GLUT1 IHC from PIK3CA$^{Sprr2fCRE}$ mice skin lesions. (C) GLUT1 IHC from an Infantile Hemangioma patient. Note the specific staining in the EC lining the lumen. (D) WT1 IHC from PIK3CA$^{Sprr2fCRE}$ mice skin lesions. (E) WT1 IHC from an Infantile Hemangioma patient. Note the specific staining in the EC lining the lumen. (F) LYVE-1 IHC from PIK3CA$^{Sprr2fCRE}$ mice skin lesions. (G) β-galactosidase staining in the spinal section of the LacZ$^{Sprr2fCRE}$ mice. (H) Double immunofluorescence of CD31 and Cre in a VM derived from the PIK3CA$^{Sprr2f-Cre}$ mice.

Figure 12A:
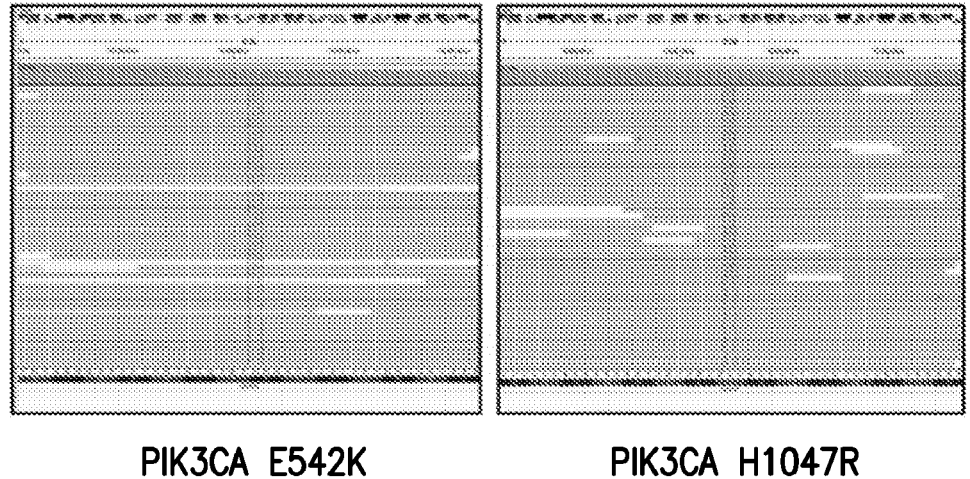
Figure 12B:

FIGS. 12A-12B. Overview of PIK3CA mutations using IGV and CNV by FISH. (A) Integrated Genome Viewer (IGV) snapshot of the representative PIK3CA hotspot mutations in the helical (E545K) and kinase (H1047R) domains from two different patients. (B) Representative microscopic images of FISH for PIK3CA (red) and PTEN (orange) from normal peripheral blood and two VM patients. CEP3 (green) is used as a control probe.

FIGS. 13A-13D. Histologic characterization of PIK3CA$^{CAG-CreER}$ mice. (A) Schematic representation of the genetic strategy used to generate PIK3CA$^{CAG-CreER}$ mice. (B) GLUT1 IHC from PIK3CA$^{CAG-CreER}$ mice skin lesions. (C) WT1 IHC from PIK3CA$^{CAG-CreER}$ mice skin lesions. (D) LYVE-1 IHC from PIK3CA$^{CAG-CreER}$ mice skin lesions.

FIGS. 14A-14E. Histologic characterization of PIK3CA$^{UBC-CreER}$ mice. (A) Schematic representation of the genetic strategy used to generate PIK3CA$^{UbqC-CreER}$ mice. (B) Representative H&E staining from a skin VM lesion. (C) Prussian blue staining from a VM lesion from PIK3CA$^{UbqC-CreER}$ mice. (D) GLUT1 IHC from PIK3CA$^{UbqC-CreER}$ mice skin lesions. (E) WT1 IHC from PIK3CA$^{UbqC-CreER}$ mice skin lesions.

FIGS. 15A-15E. Embryonic characterization of PIK3CAT$^{Tie2-Cre}$ mice. (A) Schematic representation of the genetic strategy used to generate PIK3CA$^{Tie2-Cre}$ mice. (B) BrdU incorporation assay in the endocardia of WT and PIK3CA$^{Tie2-Cre}$ embryos. Quantification is shown. (C) Cleaved caspase 3 staining in sections from WT and PIK3CA$^{Tie2-Cre}$ embryos. (D) Embryonic phenotype of WT and PIK3CA$^{Tie2-Cre}$ embryos treated with PI3Kα inhibitor. (E) pAKT IHC in sections from WT and PIK3CA$^{Tie2-Cre}$ embryos treated with vehicle or PI3Kα inhibitor.

FIG. 16. Clinical features and genomic findings in VM patients.

FIGS. 17A-17H. Histologic characterization of PIK3CA$^{Sprr2f-Cre}$ mice. (A) Schematic representation of the genetic strategy used to generate PIK3CA$^{Sprr2fCRE}$ mice. (B) Lung tissue from mouse is used as a positive control for CD31 IHC. (C) GLUT1 IHC from PIK3CA$^{Sprr2fCRE}$ mice skin lesions (left panel). GLUT1 IHC from a human Infantile Hemangioma patient (middle panel). Note the specific staining in the EC lining the lumen. Mouse positive control for GLUT-1 IHC is shown (kidney; right panel). (D) WT1 IHC from PIK3CA$^{Sprr2fCRE}$ mice skin lesions (left panel). WT1 IHC from a human Infantile Hemangioma patient (middle panel). Note the specific staining in the EC lining the lumen. Mouse positive control for WT-1 IHC is shown (Sertoli cells of the testis; right panel). (E) LYVE-1 IHC from PIK3CA$^{Sprr2fCRE}$ mice skin lesions (left panel). Mouse positive control for LYVE-1 IHC is shown (embryonic liver; right panel). Note that inflammatory cells stain positive for LYVE-1. (F). PROX-1 IHC from PIK3CA$^{Sprr2fCRE}$ mice skin lesions (left panel). Mouse positive control for PROX-1 IHC is shown (embryonic liver; right panel). Note that inflammatory cells stain positive for PROX-1. (G) β-galactosidase staining in the spinal section of the LacZ$^{Sprr2f-Cre}$ mice. Arrows indicate cells with positivity for the β-gal staining. (H) Double immunofluorescence of CD31 and Cre in a VM derived from the PIK3CA$^{Sprr2f-Cre}$ mice. Arrows indicate nuclei that are positive for the Cre and the CD31 staining.

FIGS. 18A-18F. PIK3CA$^{Sprr2fCRE}$ mice develop spinal vascular malformations (A) Hind limb paresis phenotype observed in the PIK3CA$^{Sprr2fCRE}$ mice. (B) Gross and detailed histology of the spinal cord of the PIK3CA$^{Sprr2fCRE}$ mice compared to a normal WT spine. Arrows indicate the multiple focal hemorrhages found in the spinal cord. (C) microCT scan of a WT mouse compared to PIK3CA$^{Sprr2fCRE}$ mice littermates showing an early and an advanced phenotype. Arrows indicate the slow flow and extravasation lesions observed in the spinal cord. (D) H&E histology from normal skin and cutaneous VM. Dashed line delimits the dermis (lower) from the epidermis (upper). Arrows indicate normal blood vessels. (E) CD31 IHC of the skin VM lesions. Arrows indicate normal blood vessels. (F) Prussian blue staining. Dashed line delimits the dermis (lower) from the epidermis (upper). Arrow indicates normal blood vessel.

FIGS. 19A-19H. PIK3CA mutations cause sporadic VM in humans (A) Western blot of human skin ECs infected with empty vector (EV), PIK3CA WT, and H1047R mutation probed with the indicated antibodies. Cells were serum-starved overnight before lysis. (B) Representative images from the tube formation assays of primary ECs infected with empty vector (EV), PIK3CA WT, and H1047R mutation and serum-starved overnight before seeding. Pictures were taken 6 hours after seeding. Note the reticular network formed in the EV and PIK3CA WT cells that fails to form in the PIK3CA H1047R mutant cells. Scale bars, 200 μm. (C) EdU incorporation assay quantification of ECs infected with empty vector (EV), PIK3CA WT, and H1047R mutation, serum-starved overnight, and labeled with EdU for 4 hours. Graph shows mean fold change ±SEM. N=3 biological replicates. P-values were calculated using Student's t-test. (D) H&E staining highlighting the representative morphology of one of the human VM patients sequenced in this study. Blood pools and thick mural cell layer are evident in the histological sections of these patients. (E) Characteristic MRI scan from an intramuscular sporadic VM patient sequenced in this study. T1 axial and coronal sections are shown. Dashed line delimits the radiological extension of the malformation. [R] and [L] indicates right and left, respectively. (F) PI3Kα domains and specific sites found to be mutated in this study. As shown from left to right in the figure, the p85-binding domain is represented in green, the Ras-binding domain (RBD) in red, the C2 domain in blue, the helical domain in yellow, and the kinase domain in purple. (G) Schematic pathway depicting TIE2, PI3K, and MAPK pathway gene components found to be mutated in sporadic VM by MSK-IMPACT in this study. Activating mutations are indicated in red (TEK, GNAQ, IRS2, MAP2K1, PIK3CA, AKT2, AKT3) and inactivating mutations in blue (NF1). Dark red designates mutations found in more that 20% of the patients (TEK, PIK3CA). Unknown mutations are shown in gray (MAP3K1). (H) Mutual exclusivity of the gene mutations present in the TEK and PIK3CA pathways. The activating mutations in TEK are indicated in blue, and the activating mutations in PIK3CA are in red. The alterations affecting genes involved in the PI3K or MAPK pathways are represented in green.

FIGS. 20A-20H. PIK3CA mutation in endothelial cells. (A) Western blot of human HUVEC cells infected with empty vector (EV), PIK3CA WT, and H1047R mutation probed with the indicated antibodies. Cells were serum-starved overnight before lysis. (B) Representative images from the tube formation assays of HUVEC cells infected with empty vector (EV), PIK3CA WT, and H1047R mutation and serum-starved overnight before seeding. Pictures were taken 8 hours after seeding. Note the reticular network formed in the EV and PIK3CA WT cells that fails to form in the PIK3CA H1047R mutant cells. (C) BYL719 dose-response EdU incorporation assay in primary EC transduced with the PIK3CA H1047R mutation. P-value was calculated using Student's t-test at 1 μM. Graph indicates fold change ±SD. N=2 biological replicates. (D) Western blot of primary EC transduced with the PIK3CA H1047R mutation probed with the indicated antibodies. Cells were treated for 4 hours with the indicated doses of BYL719. (E) Antibody arrays including angiogenesis-related cytokine probes were hybridized with lysates (500 μg) from human primary EC infected with empty vector (EV), PIK3CA WT, and H1047R mutation. Densitometry quantification was performed with ImageJ software, and is indicated as a fold change. (F) ANG2 mRNA and protein levels analyzed from human primary EC infected with empty vector (EV), PIK3CA WT, and H1047R mutation and serum-starved overnight by RT-qPCR and ELISA, respectively. P-value was calculated using Student's t-test. Graph indicates mean levels (ELISA) and fold change (mRNA)±SEM. N=3 biological replicates. ANG2 mRNA and protein levels analyzed from human primary EC infected with PIK3CA H1047R mutation, serum-starved, and treated overnight with BYL719 (1 μM), MK2206 (1 μM), and Everolimus (50 nM) by RT-qPCR and ELISA, respectively. P-value was calculated using Student's t-test. Graph indicates mean levels (ELISA) and fold change (mRNA) SEM. N=3 biological replicates. (G) Integrated Genome Viewer (IGV) snapshot of the representative PIK3CA hotspot mutations in the helical (E545K) and kinase (H1047R) domains from two different patients. Note the presence of WT and mutant reads, which in our patients yielded an allele frequency of 5-10%. (H) Representative microscopic images of FISH for PIK3CA (red) and PTEN (orange) from normal peripheral blood (control) and two VM patients. CEP3 (green) is used as a control probe.

FIG. 21. Clinical features and genomic findings in VM patients. This table includes the Age, gender, location of VM, mutations identified, and allele frequencies are provided for the PIK3CA and TEK mutations.

FIGS. 22A-22F. Histologic characterization of PIK3CA$^{CAG\text{-}CreER}$ mice. (A) Schematic representation of the genetic strategy used to generate PIK3CA$^{CAG\text{-}CreER}$ mice. (B) GLUT-1 IHC from PIK3CA$^{CAG\text{-}CreER}$ mice skin lesions. (C) WT1 IHC from PIK3CA$^{CAG\text{-}CreER}$ mice skin lesions. Note that these stainings (GLUT-1 and WT-1) are negative as compared to Infantile Hemangioma patients shown in FIG. 17. Specificity of these antibodies in mouse tissue is shown in FIG. S1.(D). LYVE-1 IHC from PIK3CA$^{CAG\text{-}CreER}$ mice skin lesions. (E) PROX-1 IHC from PIK3CA$^{CAG\text{-}CreER}$ mice skin lesions. Note that these stainings (LYVE-1 and PROX-1) are negative as compared to positive controls shown in FIG. 17 and that inflammatory cells stain positive for these markers.

FIGS. 23A-23K. Ubiquitous expression of PIK3CA$^{H1047R}$ induces VM. (A) Disease-free survival plot of PIK3CA$^{CAG\text{-}CreER}$ (n=20) and PIK3CA$^{WT}$ (n=25) littermates on tamoxifen diet assessed by the appearance of visible cutaneous VM. Dotted line represents the time when tamoxifen diet was administered (day 21). P-value was calculated using Log-rank test. (B) H&E staining of a representative normal blood vessel and a VM lesion developed in the skin of PIK3CA$^{CAG\text{-}CreER}$ mice. Arrow indicates normal blood vessel. (C) CD31 IHC staining showing positivity for the endothelial cells of a normal blood vessel and VM. Note that erythrocytes exhibit nonspecific staining. Arrow indicates normal blood vessel. (D) Phosphorylated AKT (S473) IHC. The arrow in the bottom panel indicates lining ECs that show positivity for the staining. Note the negativity for pAKT in the normal blood vessel (above, indicated by an arrow). (E) Prussian blue staining of normal blood vessels and the PIK3CA$^{CAGCreER}$ mouse skin VM lesions. Arrow indicates a normal blood vessel. (F) Histological representation of mesenteric vasculature and VM harvested during necropsy and detailed view to highlight the blood pools observed in the preparations. Arrows indicate normal blood vessels. (G) CD31 and H. Prussian blue positivity for the VM described in (F). (I). BrdU incorporation (red) in PIK3CA$^{CAG\text{-}CreER}$ VM compared to normal blood vessels. CD31 (green) and DAPI (blue) show endothelial cells and nuclei, respectively. Note the encased BrdU-positive nuclei in the CD31-positive lining endothelial cell layer. (J) Quantification of BrdU positive nuclei in normal blood vessels and VM. P-value was calculated using Student's t-test. Graph shows mean±SD. N=45 fields from 5 biological replicates. (K) Morphological quantification of the maximal blood vessel diameter of normal vessels and VM. P-value was calculated using Student's t-test. Graph shows mean±SD. N=45 fields from 5 biological replicates.

FIGS. 24A-24F. Histologic characterization of PIK3CA$^{UBC\text{-}CreER}$ mice. (A) Schematic representation of the genetic strategy used to generate PIK3CA$^{UbqC\text{-}CreER}$ mice. (B) Representative H&E staining from a skin VM lesion. (C) Prussian blue staining from a VM lesion from PIK3CA$^{UbqC\text{-}CreER}$ mice. (D) GLUT1 IHC from PIK3CA$^{UbqC-CreER}$ mice skin lesions. (E) WT1 IHC from PIK3CA$^{UbqC-CreER}$ mice skin lesions. (F) PROX-1 WT1 IHC from PIK3CA$^{UbqC-CreER}$ mice skin lesions. Note that these stainings (GLUT-1, WT-1, and PROX-1) are negative as compared to positive controls shown in FIG. 17 and that inflammatory cells stain positive for these markers.

FIGS. 25A-25D. Cell proliferation in mouse VM and in vivo treatments. (A) Ki-67 IHC from a PIK3CA$^{CAG-CreER}$ mouse VM lesion. Arrows indicate positivity in EC nuclei. (B) Representative images depicting proliferation by Ki67 staining (red; magnified field) in normal and VM vessels stained with CD31 (green). DAPI is shown in blue. (C) Representative images depicting proliferation by BrdU incorporation (magnified field) in the VM treated with vehicle or PI3Kα inhibitor during one week (BYL719-50 mg×kg$^{-1}$; daily p.o.). Images were acquired for 10 different biological replicates. (D) Representative images depicting proliferation by BrdU incorporation (magnified field) in the VM treated with vehicle, everolimus (10 mg×kg$^{-1}$; daily p.o.), or propranolol (40 mg×kg$^{-1}$; daily p.o.) during one week. Images were acquired for 8 different biological replicates.

FIGS. 26A-26G. PI3K inhibitors are effective for the treatment of VM. (A) Schematic representation and images from the allotransplantation assays. (B) Quantification of plasma D-dimers measured in animals with or without VM. P-value was calculated using Student's t-test. (C) VM volume measured in PIK3CA$^{CAG-CreER}$ VM-derived allografts treated with vehicle or PI3Kα inhibitor for one week (BYL719, 50 mg×kg-1; daily p.o.). P-value was calculated using Student's t-test. (D) Quantification of BrdU incorporation and cleaved caspase 3 in CD31-positive cells from (B). P-value was calculated using Student's t-test. N=10. (E) VM volume measured in PIK3CA$^{CAG-CreER}$ VM-derived allografts treated with vehicle, everolimus (10 mg×kg-1; daily p.o.), or propranolol (40 mg×kg-1; daily p.o.) for one week. P-value was calculated using Student's t-test. (F) Quantification of BrdU incorporation and cleaved caspase 3 in CD31-positive cells from (E). P-value was calculated using Student's t-test. N=8. (G) VM volume in PIK3CA$^{CAG-CreER}$ VM-derived allografts treated topically with BYL719 1% (w/w) using two different formulations (free and soluble BYL719) for 3 weeks. The pre-treatment time point indicates when the treatment was started. All treatments in week 1, 2, and 3 have a p<0.001 as compared to the vehicle control VM. P-values were calculated using Student's t-test.

Figure 27A:
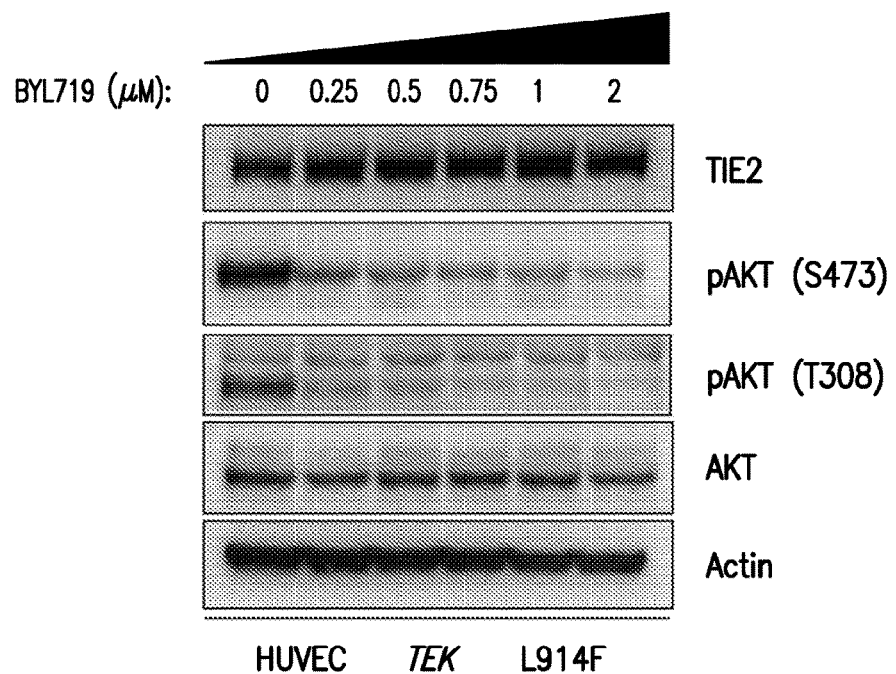
Figure 27B:
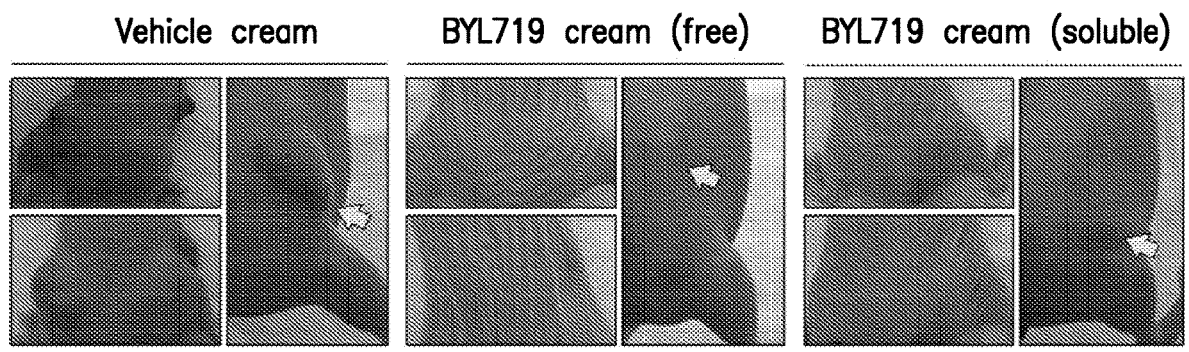

FIGS. 27A-27B. Treatment of VM with PI3K inhibitors. (A) Western blot of HUVEC cells transduced with TEK L914F mutation and probed with the indicated antibodies. Cells were treated for 4 hours with the indicated doses of BYL719. (B) Representative images of the allograft VM treated with the topical formulation of BYL719. Free and soluble refer to the two different preparations of the topical formula. Arrows indicate the area affected by the VM allograft.

FIGS. 28A-28F. Histological assessment of PIK3CA$^{Tie2-Cre}$ embryos. (A) Schematic representation of the genetic strategy used to generate the PIK3CA$^{Tie2-Cre}$ mice. (B) Pericardial cavity (arrow) was normal in E9.0 PIK3CA$^{Tie2-Cre}$ embryos, suggesting normal cardiac function at this stage. Scale bar is 100 μm. (C) BrdU incorporation (green) assay in the heart of WT and PIK3CA$^{Tie2-Cre}$ E9.0 embryos. Quantification is shown as the mean percentage ±SD. (WT=35.5%±4.4, n=475 from 3 different embryos; PIK3CA$^{Tie2-Cre}$=34.9%±3.5; n=413 from 3 embryos; p=ns). Arrowheads indicate representative nuclei from the heart that are positive for BrdU incorporation. Scale bar is 100 μm. DAPI is shown in blue. (D) Cleaved Caspase 3 (green) expression in cross-sections of E9.5 embryos. At the dorsal region (i) staining is negative in wild-type embryos (0.4%±0.2; n=821 cells from 3 embryos) but is increased in PIK3CA$^{Tie2-Cre}$ embryos (19%±6.0; n=754 from 3 embryos; p<0.001 by Student's t-test). In contrast, cleaved Caspase 3 staining is negative at the cardiac region (ii) (WT=0.6%±0.3; n=444 from 3 embryos; PIK3CA$^{Tie2-Cre}$=0.5%±0.3; n=428 from 3 embryos; p=ns). Values are mean±SD. Scale bar is 100 μm. DAPI is shown in blue. (E) Embryonic phenotype of WT and PIK3CA$^{Tie2-Cre}$ embryos treated with PI3Kα inhibitor. For morphological studies upon PI3K inhibition, a minimum of 3 dissections/treatment were performed. (F) pAKT IHC in sections from WT and PIK3CA$^{Tie2-Cre}$ embryos treated with vehicle or PI3Kα inhibitor. For pAKT histologic studies a minimum of 4 embryos for each condition were used.

FIGS. 29A-29E. PIK3CAH1047R impairs embryonic angiogenesis. (A) Embryonic phenotype observed in PIK3CA$^{WT}$ (left) and PIK3CA$^{Tie2-Cre}$ (right) littermates at E10. For morphological studies, a minimum of 4 dissections for each genotype were performed yielding N≥15 embryos. (B) CD31 staining of coronal sections from PIK3CA$^{WT}$ and PIK3CA$^{Tie2-Cre}$ embryos at E9.5. Arrowheads indicate blood vessel enlargement defects in the meningeal vessels (upper panel), and arrows indicate the defects in the intersomitic vessels (lower panel). For CD31 histologic studies, a minimum of 4 embryos for each phenotype obtained from two different dissections were used. Scale bars, 100 μm. (C) Whole embryo CD31 staining of PIK3CA$^{WT}$ and PIK3CA$^{Tie2-Cre}$ embryos from mice treated with vehicle or PI3Kα inhibitor (BYL719, 50 mg×kg-1; daily p.o.; 48, 24, and 2 hours before embryos are harvested). For CD31 histologic studies, a minimum of 4 embryos for each condition were used. (D) Detailed view of the cephalic and intersomitic blood vessels from (C). Arrow indicates defects in the meningeal (upper panel) and the intersomitic vessels (lower panel). (E) CD31 coronal sections from embryos in (D). CV (Cardinal vein); DA (Dorsal aorta). Scale bars, 100 μm.

FIG. 30. Bait sequences used for TEK targeted sequencing. This table includes the DNA sequence for the oligonucleotides using in the targeted TEK sequencing.

5. DETAILED DESCRIPTION OF THE INVENTION

For clarity and not by way of limitation, the detailed description of the invention is divided into the following subsections:

(1) subjects for treatment;
(2) mutations in the PI3K/Akt pathway;
(3) PI3K inhibitors;
(4) methods of treatment;
(5) pharmaceutical formulations; and
(6) kits.

5.1 Subjects for Treatment

The present invention may be used for treatment of a human or a non-human animal subject, including but not limited to a non-human primate, a dog, a cat, a horse, a rabbit, a mouse, a rat, a guinea pig, or a hamster.

In certain non-limiting embodiments, the subject is a human.

The term "vascular malformation," as used herein, refers to a non-malignant, congenital abnormality of blood and/or lymph vessels that may be apparent at birth or alternatively may not be apparent at birth and may present weeks, months, or years later. In certain non-limiting embodiments, the vascular malformation is not a hemangioma.

In certain non-limiting embodiments, a vascular malformation is characterized by the presence of a single endothelial layer forming distended blood vessels of variable diameter that are surrounded by a disorganized mural cell layer containing both smooth muscle cells and pericytes.

In certain embodiments, the vascular malformation expresses the protein CD31. In certain embodiments, the vascular malformation expresses phosphorylated AKT.

In certain embodiments, the vascular malformation does not express detectable levels of a hemanigioma marker, for example, glucose transporter 1 (GLUT-1) and/or Wilms tumor 1 (WT-1).

In certain embodiments, the vascular malformation does not express detectable levels of a lymphatic-specific marker, for example, lymphatic vessel endothelial hyaluronan receptor 1 (LYVE-1) and/or prospero homeobox 1 (PROX-1).

In certain non-limiting embodiments, the vascular malformation may be a venous malformation, an arterial malformation, an arteriovenous malformation or a lymphatic vessel malformation. In certain non-limiting embodiments, the subject suffers from multiple vascular malformations.

Vascular malformations may be located in or adjacent to diverse areas of the body, including but not limited to the central nervous system (brain, spinal cord), skin, eye (including but not limited to the retina), ear, (facial) sinus, organs such as the lung, heart, liver, gallbladder, spleen, gastrointestinal system (esophagus, stomach, duodenum, intestine, colon, rectum), pancreas, kidney, bladder, ovary, testicle, joints, nose, lips, etc.

In certain non-limiting embodiments, the subject suffers from a malignancy.

In certain non-limiting embodiments, the subject is not known to suffer from a malignancy.

In certain non-limiting embodiments, the subject suffers from a multisystem genetic disorder.

In certain non-limiting embodiments, the subject is not known to suffer from a multisystem genetic disorder.

In certain non-limiting embodiments, the subject suffers from at least one vascular malformation, the surgical treatment of which would be high-risk. These would include vascular malformations in an area that is, because of its location, difficult to access without substantial risk of morbidity or mortality (for example, but not limited to, malformations in the brain, e.g., the brainstem), as well as malformations in a weakened subject where surgery is contraindicated. Further, if there are multiple lesions, medical treatment may be preferable over surgical options because of aggregate risk, efficiency, or because of risk of recurrence.

In certain non-limiting embodiments, the subject is at risk for occurrence or recurrence of a vascular malformation, for example because of heredity and/or a previously existing lesion.

5.2 Mutations in the PI3K/Akt Pathway

Mutations in the PI3K/Akt pathway related to the invention include, but are not limited to, activating mutations in PIK3 itself, for example, an activating mutation in PIK3CA, as well as mutations in one or more of AKT1, AKT2, AKT3, and/or IRS2. These loci may have single or multiple mutations that may be substitutions, insertions, or deletions.

In non-limiting embodiments, the PIK3CA is human PIK3CA. See Kang, S. et al., (2005) Proc Natl Acad Sci USA. 102(3):802-7.

In other non-limiting embodiments, the PIK3CA is a human PIK3CA encoded by a nucleic acid described by GenBank Accession No. NM_006218, or a nucleic acid having a sequence that is at least 80 percent, at least 85 percent, at least 90 percent, or at least 95 percent, or at least 99 percent homologous thereto (where homology may be determined using standard software such as BLAST or FASTA).

In other non-limiting embodiments, the PIK3CA is a human PIK3CA having an amino acid sequence as described by GenBank Accession No. NP_006209, or a protein having a sequence that is at least 80 percent, at least 85 percent, at least 90 percent, or at least 95 percent, or at least 99 percent homologous thereto (where homology may be determined using standard software such as BLAST or FASTA).

In certain non-limiting embodiments, the activating mutation of PIK3CA is at amino acid 88, 542, 545, 1047, 420, or 143. In certain non-limiting embodiments, the mutation is selected from the group consisting of R88Q, E542K, E545K, E545Q, H1047L, H1047Q, H1047R, C420R, and I143V.

5.3 PI3K Inhibitors

PI3K inhibitors that may be used according to the invention include inhibitors that are highly specific for PI3K or, alternatively, are PI3K selective. Inhibitors of the PI3K/Akt pathway may also be used according to certain embodiments of the invention, for example, but not limited to, inhibitors specific or selective for Akt1, Akt2, Akt3 or IRS2.

Non-limiting examples of agents that may be used according to the invention include BYL719 (Alpelisib; Fritsch et al., 1 Cancer Ther. 2014 May; 13(5):1117-29; doi: 10.1158/1535-7163), GDC-0032, BKM-120, BEZ235, GNE-317, PI-103, PIK-75, BGT226, GSK1059615, PF-04691502, CNIO-PI3Ki, GSK2126558, XL147, PKI-402, GDC0980, BGT226, GSK1059615, PF-04691502, perifosine (Kondapaka et al., Mol Cancer Ther November 2003 2; 1093), copanlisib (2-Amino-N-[7-methoxy-8-(3-morpholin-4-yl-propoxy)-2,3-dihydroimidazo[1,2-c]quinazolin-5-yl]pyrimidine-5-carboxamide), PI-103 (Zou et al., Int J Mol Med. 2009 July; 24(1):97-1010), 2-methyl-5-nitro-2-[(6-bromo-imidazo[1,2-a]pyridin-3-yl)methylene]-1-methylhydrazide-benzenesulfonic acid, monohydrochloride (Fan et al., Cell 125 733-747 (2006)), CAS 371943-05-4 (Hayakawa, M., et al. 2006. Bioorg. Med. Chem. 14: 6847-6858), BAY80-6946 (Copanlisib), CH5132799, GDC-0941 (Pictilisib), A66, PIK 90, HS-173, and MK2206 (8-[4-(1-aminocyclobutyl)phenyl]-9-phenyl-1,2,4-triazolo[3,4-f][1,6]naphthyridin-3(2H)-one, dihydrochloride).

5.4 Methods of Treatment

In certain non-limiting embodiments, the present invention provides for a method of treating a vascular malformation in a subject, where the subject has a gain-of-function mutation in the PI3K/AKT pathway, comprising administering, to the subject, an effective amount of an agent that inhibits the PI3K/AKT pathway, for example, but not limited to, where the gain of function mutation is in PIK3CA, AKT1, AKT2, AKT3, and/or IRS2.

In certain non-limiting embodiments, the present invention provides for a method of treating a vascular malformation in a subject comprising (i) determining whether the subject has a gain-of-function mutation in the PI3K/AKT pathway; and (ii) where the subject has a gain-of-function mutation in the PI3K/AKT pathway, treating the subject with an agent that inhibits the PI3K/AKT pathway, or, where the subject does not have an activating mutation of PIK3CA, treating with another modality such as surgery, embolization, sclerosing or occlusion (e.g., application of a clip).

In certain non-limiting embodiments, the present invention provides for a method of treating a vascular malformation in a subject, where the subject has a gain-of-function mutation in endothelial-specific tyrosine kinase receptor TEK (TIE2), comprising administering, to the subject, an effective amount of an agent that inhibits the PI3K/AKT pathway.

In certain non-limiting embodiments, the present invention provides for a method of treating a vascular malformation in a subject comprising (i) determining whether the subject has a gain-of-function mutation in endothelial-specific tyrosine kinase receptor TEK (TIE2); and (ii) where the subject has a gain-of-function mutation in endothelial-specific tyrosine kinase receptor TEK (TIE2), treating the subject with an agent that inhibits the PI3K/AKT pathway, or, where the subject does not have an activating mutation of endothelial-specific tyrosine kinase receptor TEK (TIE2), treating with another modality such as surgery, embolization, sclerosing or occlusion (e.g., application of a clip).

As used herein "treating" refers to achieving an improvement in an existing lesion or reducing the risk of occurrence or recurrence of a lesion in a subject in need of such treatment, such as, but not limited to, a subject having a preexisting vascular malformation, a malignancy, a genetic disorder, or a family history of a genetic disorder. Non-limiting examples of improvement in an existing lesion include maintenance of size, reduction in size, maintenance of volume, reduction in volume, maintenance of structural integrity, reduction in risk of rupture and/or hemorrhage, reduction in pain, reduction in swelling, and/or reduction in redness.

In certain non-limiting embodiments, the agent that inhibits the PI3K/AKT pathway is administered in an amount effective to increase the expression of angiopoietin-2 (ANG2) mRNA and/or protein.

In certain non-limiting embodiments, the present invention provides for further treating the subject with an amount of a second inhibitor of the PI3K/Akt pathway in an amount that, together with the first inhibitor, effectively treats the vascular malformation.

The inhibitors of the invention may be administered by any route, including but not limited to, oral, rectal, systemic, nasal, pulmonary, topical, intravenous, intraarterial, intraperitoneal, intrathecal, and/or by local instillation in the area of or into the vascular malformation. For example, and not by way of limitation, a method of the present invention can comprise topical administration of the agent that inhibits the PI3K/AKT pathway. Alternatively and/or additionally, in certain embodiments, a method of the present invention can comprise oral administration of the agent that inhibits the PI3K/AKT pathway. In certain embodiments, a method of the present invention can comprise parenteral administration of the agent that inhibits the PI3K/AKT pathway.

The treatment methods of the invention may be administered alone or in conjunction with another form of pharmaceutical and/or surgical therapy. Non-limiting examples of pharmaceutical treatments and/or agents include, but are not limited, to treatment with one or more of: an anti-angiogenic agent, a steroid, an mTOR inhibitor, a beta-blocker (e.g., propranolol), and/or an agent that reduces blood pressure. In certain embodiments, "in conjunction with," means that an inhibitor of the PI3K/Akt pathway and another pharmaceutical agent, e.g., an mTOR inhibitor, are administered to a subject as part of a treatment regimen or plan. In certain embodiments, being used in conjunction does not require that the PI3K/Akt pathway inhibitor and the pharmaceutical agent are physically combined prior to administration or that they be administered over the same time frame.

5.5 Pharmaceutical Compositions

The present invention further provides pharmaceutical formulations of the disclosed inhibitors for therapeutic use as set forth above. For example, and not by way of limitation, the present invention provides pharmaceutical formulations comprising one or more, two or more, three or more, four or more inhibitors disclosed herein and a pharmaceutically acceptable carrier. In certain embodiments, a pharmaceutical formulation of the present invention comprises one or more, two or more, three or more, four or more PI3K/Akt pathway inhibitors (e.g., PI3K inhibitors) and a pharmaceutically acceptable carrier.

In certain embodiments, the present invention provides pharmaceutical formulations comprising one or more PI3K/Akt pathway inhibitors and a pharmaceutically acceptable carrier. For example, and not by way of limitation, a pharmaceutical formulation of the present invention can comprise an agent that inhibits the PI3K/AKT pathway such as, but not limited to, GDC-0032, BKM-120, BEZ235, GNE-317, PI-103, PIK-75, BGT226, GSK1059615, PF-04691502, CNIO-PI3Ki, GSK2126558, XL147, PKI-402, GDC0980, BGT226, GSK1059615, PF-04691502, and MK2206. In certain embodiments, the present invention provides pharmaceutical formulations comprising one or more inhibitors specific or selective for Akt1, Akt2, Akt3 and/or IRS2 and a pharmaceutically acceptable carrier.

In certain embodiments, the present invention provides pharmaceutical formulations comprising one or more PI3K inhibitors and a pharmaceutically acceptable carrier. In certain embodiments, the present invention provides pharmaceutical formulations comprising one or more inhibitors of the alpha isoform (p110α) of PI3K and a pharmaceutically acceptable carrier. For example, and not by way of limitation, the pharmaceutical formulation can comprise a PI3K inhibitor such as, but not limited to, BYL719 (Alpelisib), BAY80-6946 (Copanlisib), CH5132799, GDC-0941 (Pictilisib), A66, PIK 90, and HS-173. In certain embodiments, the pharmaceutical formulation comprises BYL719 and a pharmaceutically acceptable carrier.

As used herein, the term "pharmaceutically acceptable carrier" refers to any and all solvents, dispersion media, coatings, binders, antibacterial and antifungal agents, isotonic and absorption delaying agents, and the like, compatible with pharmaceutical administration. The use of such media and agents for pharmaceutically active substances is well known in the art. Pharmaceutically acceptable carriers are generally nontoxic to recipients at the dosages and concentrations employed, and include, but are not limited to, buffers such as phosphate, citrate, and other organic acids; antioxidants including ascorbic acid and methionine; preservatives (such as, but not limited to, octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol and m-cresol); low molecular weight (less than about 10 residues) polypeptides; proteins, such as serum albumin, gelatin or immunoglobulins; hydrophilic polymers such as polyvinylpyrrolidone; amino acids such as glycine, glutamine, asparagine, histidine, arginine or lysine; monosaccharides, disaccharides, and other carbohydrates including glucose, mannose or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). In certain embodiments, a suitable pharmaceutically acceptable carrier can include one or more of water, saline, phosphate buffered saline, dextrose, glycerol, ethanol or combinations thereof.

In certain embodiments, a pharmaceutical formulation of the present invention can be suitable for oral, intravenous, intramuscular, enteral, subcutaneous, parenteral, systemic, local, spinal, nasal, topical or epidermal administration (e.g., by injection or infusion). The formulations can conveniently be presented in unit dosage form and can be prepared by any methods known in the art of pharmacy. In certain embodiments, a pharmaceutical formulation can be administered to a subject from a source implanted in the subject. In certain embodiments, administration of a pharmaceutical formulation of the present invention can occur by continuous infusion over a selected period of time.

In certain embodiments, the pharmaceutical formulation can be suitable for oral administration (e.g., including buccal and sublingual administration). In certain embodiments, the present invention provides an oral formulation comprising an inhibitor of the PI3K/Akt pathway. In certain embodiments, the present invention provides an oral formulation comprising a PI3K inhibitor. For example, and not by way of limitation, a pharmaceutical formulation of the present invention can be an oral formulation comprising the PI3K inhibitor, e.g., BYL719.

In certain embodiments, the pharmaceutical formulation can be suitable for topical administration. In certain embodiments, the present invention provides a topical formulation comprising an inhibitor of the PI3K/Akt pathway. In certain embodiments, the present invention provides a topical formulation comprising a PI3K inhibitor. For example, and not by way of limitation, the present invention provides a topical formulation comprising BYL719. Dosage forms for the topical or transdermal administration of the inhibitors of the present invention include, but are not limited to, powders, sprays, ointments, pastes, creams, lotions, gels, solutions, patches and inhalants. In certain non-limiting embodiments, a topical formulation comprises one or more PI3K inhibitor comprised in micelles, liposomes, or non-lipid based microspheres. In certain non-limiting embodiments, such a topical formulation may comprise a permeability enhancing agent such as but not limited to dimethyl sulfoxide, hydrocarbons (for example, alkanes and alkenes), alcohols (for example, glycols and glycerols), acids (for example, fatty acids), amines, amides, esters (for example, isopropyl myristate), surfactants (for example, anionic, cationic, or non-ionic surfactants), terpenes, and lipids (for example, phospholipids).

In certain embodiments, the pharmaceutical formulation can be suitable for parenteral administration. The terms "parenteral administration" and "administered parenterally," as used herein, refers to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In certain embodiments, the present invention provides a parenteral formulation comprising an inhibitor of the PI3K/Akt pathway. In certain embodiments, the present invention provides a parenteral formulation comprising a PI3K inhibitor. For example, and not by way of limitation, the present invention provides a parenteral formulation comprising BYL719.

In certain embodiments, a formulation of the present invention, e.g., an oral or topical formulation, can comprise from about 0.1% to about 20% w/w of an inhibitor, e.g., an inhibitor of the PI3K/Akt pathway (e.g., a PI3K inhibitor) disclosed herein. For example, and not by way of limitation, a pharmaceutical formulation can comprise from about 0.5% to about 20%, from about 1% to about 20%, from about 2% to about 20%, from about 3% to about 20%, from about 4% to about 20%, from about 5% to about 20%, from about 6% to about 20%, from about 7% to about 20%, from about 8% to about 20%, from about 9% to about 20%, from about 10% to about 20%, from about 11% to about 20%, from about 12% to about 20%, from about 13% to about 20%, from about 14% to about 20%, from about 15% to about 20%, from about 16% to about 20%, from about 17% to about 20%, from about 18% to about 20%, from about 19% to about 20%, from about 0.1% to about 19%, from about 0.1% to about 18%, from about 0.1% to about 17%, from about 0.1% to about 16%, from about 0.1% to about 15%, from about 0.1% to about 14%, from about 0.1% to about 13%, from about 0.1% to about 12%, from about 0.1% to about 11%, from about 0.1% to about 10%, from about 0.1% to about 9%, from about 0.1% to about 8%, from about 0.1% to about 7%, from about 0.1% to about 6%, from about 0.1% to about 5%, from about 0.1% to about 4%, from about 0.1% to about 3%, from about 0.1% to about 2%, from about 0.1% to about 1%, from about 1% to about 10%, from about 1% to about 5%, from about 1% to about 4%, from about 1% to about 3% or from about 1% to about 2%. In certain embodiments, a formulation of the present invention, e.g., an oral or topical formulation, can comprise from about 0.5% to about 2% w/w, e.g., about 1% w/w, of an inhibitor disclosed herein. For example, and not by way of limitation, a formulation of the present invention, e.g., an oral formulation, can comprise from about 0.5% to about 2% w/w, e.g., about 1% w/w, of BYL719. In certain embodiments, an oral formulation of the present invention comprises about 1% w/w of BYL719.

In certain embodiments, an inhibitor of the present invention, e.g., an inhibitor of the PI3K/Akt pathway (e.g., a PI3K inhibitor) can be administered to a subject at an amount of about 0.1 mg/kg to about 100 mg/kg (see Reagan-Shaw et al., The FASEB J., Vol. 22: 659-661 (2008)). For example, and not by way of limitation, an inhibitor can be administered at an amount of about 0.1 mg/kg to about 90 mg/kg, about 0.1 mg/kg to about 80 mg/kg, about 0.1 mg/kg to about 70 mg/kg, about 0.1 mg/kg to about 60 mg/kg, about 0.1 mg/kg to about 50 mg/kg, about 0.1 mg/kg to about 40 mg/kg, about 0.1 mg/kg to about 30 mg/kg, about 0.1 mg/kg to about 20 mg/kg, about 0.1 mg/kg to about 15 mg/kg, about 0.1 mg/kg to about 10 mg/kg, about 0.1 mg/kg to about 5 mg/kg, about 0.1 mg/kg to about 1 mg/kg, about 1 mg/kg to about 100 mg/kg, about 5 mg/kg to about 100 mg/kg, about 10 mg/kg to about 100 mg/kg, about 20 mg/kg to about 100 mg/kg, about 30 mg/kg to about 100 mg/kg, about 40 mg/kg to about 100 mg/kg, about 50 mg/kg to about 100 mg/kg, about 60 mg/kg to about 100 mg/kg, about 70 mg/kg to about 100 mg/kg, about 80 mg/kg to about 100 mg/kg or about 90 mg/kg to about 100 mg/kg, e.g., by one or more separate administrations, or by continuous infusion. In certain embodiments, an inhibitor of the present invention can be administered at an amount of about 20 mg/kg to about 60 mg/kg, e.g., about 50 mg/kg. In certain embodiments, an inhibitor of the present invention can be administered at an amount of about 1 mg/kg to about 5 mg/kg, e.g., about 4 mg/kg.

In certain embodiments, the inhibitors of the present invention can be administered to a subject at least: twice every day, once every day, once every two days, once every three days, once every four days, once every five days, once every six days, once a week, once every two weeks, once every three weeks, once every month, once every two months, once every three months, once every six months or once every year. In certain embodiments, the inhibitors of the present invention can be administered one or more times per day. For example, and not by way of limitation, the inhibitors of the present invention can be administered once, twice, three, four, five or more times a day.

In certain embodiments, a formulation of the present invention can further comprise an additional active agent. Non-limiting examples of additional active agents that can be present within a formulation of the present invention include an anti-angiogenic agent, a steroid, an mTOR inhibitor (e.g., everolimus), a beta-blocker (e.g., propranolol), and/or an agent that reduces blood pressure.

5.6 Kits

In certain embodiments, the present invention provides kits. In certain embodiments, a kit can comprise a container, such as a vial, that includes a pharmaceutical formulation comprising an inhibitor of the PI3K/Akt pathway (e.g., a PI3K inhibitor) in a pharmaceutically acceptable carrier.

In certain embodiments, kit of the present invention can comprise an agent that inhibits the PI3K/AKT pathway such as, but not limited to, GDC-0032, BKM-120, BEZ235, GNE-317, PI-103, PIK-75, BGT226, GSK1059615, PF-04691502, CNIO-PI3Ki, GSK2126558, XL147, PKI-402, GDC0980, BGT226, GSK1059615, PF-04691502, and MK2206.

In certain embodiments, a kit of the present invention comprises a PI3K inhibitor, in a pharmaceutically acceptable carrier. For example, and not by way of limitation, a kit of the present invention can comprise an inhibitor of the alpha isoform (p110a) of PI3K. In certain embodiments, a kit can comprise a PI3K inhibitor such as, but not limited to, BYL719 (Alpelisib), BAY80-6946 (Copanlisib), CH5132799, GDC-0941 (Pictilisib), A66, PIK 90, and HS-173.

In certain embodiments, the present invention provides a kit that includes a topical formulation comprising an inhibitor of the PI3K/Akt pathway. For example, and not by way of limitation, the topical formulation can comprise BYL719. In certain embodiments, the present invention provides a kit that includes an oral formulation comprising an inhibitor of the PI3K/Akt pathway. In certain embodiments, the present invention further provides a kit that includes a parenteral formulation comprising an inhibitor of the PI3K/Akt pathway.

In certain embodiments, the kit can further include instructions, such as a product insert or label, directing the user to utilize the pharmaceutical formulation for treating a vascular malformation in a subject, e.g., in a subject that has a gain-of-function mutation in the PI3K/AKT pathway.

In certain non-limiting embodiments, the kit can comprise means of detecting one or more gain-of-function mutation in the PI3K/AKT pathway, as set forth above. Said means may comprise, for example but not by way of limitation, one or more primer or primer pair for amplification of nucleic acid and subsequent detection of a mutation described above, as embodied in nucleic acid of a subject; one or more nucleic acid probe for detection of a mutation described above, as embodied in nucleic acid of a subject; and/or an antibody, antibody fragment, or single-chain antibody for detection of a protein form of a mutation described above. Said kit may optionally further comprise a product insert or label disclosing that a vascular malformation in a subject having a gain-of-function mutation in the PI3K/AKT pathway may be treated with a PI3K inhibitor.

6. EXAMPLE 1: MOUSE MODEL BEARING PIK3CA MUTATION DEVELOPS VASCULAR MALFORMATIONS 6.1 Materials and Methods Mice.

The following mouse strains were obtained from The Jackson Laboratories: R26-LSL-PIK3CA$^{H1047R}$ (016977), CAG-CreER (017595), Tie2-Cre (004128), and UBC-CreER (008085). The Sprr2f-Cre strain (01XNA) was acquired from the National Cancer Institute (NCI) Mouse Repository and was previously described. The R26-LSL-LacZ reporter strain was available at the Mouse Transgenic Core of MSKCC. Mice were housed and maintained in a controlled environment at the Research Animal Resource Center (RARC) of MSKCC and all procedures were performed in accordance with Institutional Guidelines under the protocol number 12-10-019. Tamoxifen (Harlan; TD.130856) was administered through the food chow at approximately 40 mg×kg-1.

Histology.

For LacZ staining, mouse tissue was fixed using a solution containing 0.2% glutaraldehyde, 1% formaldehyde and 0.02% NP-40 in PBS for 1 h at 4° C. After washing, tissue was incubated in X-gal staining solution (5 mM $K_3Fe(CN)_6$, 5 mM $K_4Fe(CN)_6$ and 2 mM $MgCl_2$, 1 mg/ml X-gal in PBS) overnight at room temperature. For histology, LacZ stained tissues were fixed in 3.7% formaldehyde-PBS and embedded in paraffin, sectioned and counterstained with Nuclear FastRed.

Targeted Exome Sequencing (MSK-IMPACT).

MSK-IMPACT was performed as previously described. Briefly, DNA derived from venous malformation patients was further subjected to deep-coverage targeted sequencing of key cancer-associated genes. MSK-IMPACT (Integrated Mutation Profiling of Actionable Cancer Targets), involves hybridization of barcoded libraries to custom oligonucleotides (Nimblegen SeqCap) designed to capture all protein-coding exons and select introns of 379 commonly implicated oncogenes, tumour suppressor genes, and members of pathways deemed actionable by targeted therapies. The captured pool was subsequently sequenced on an Illumina HiSeq 2500 as paired-end 75-base pair reads, producing 513-fold coverage per tumor. Sequence data were analyzed to identify three classes of somatic alterations: single-nucleotide variants, small insertions/deletions (indels), and copy number alterations. Barcoded sequence libraries were prepared using 250 ng genomic DNA (Kapa Biosystems) and combined in a single equimolar pool. Sequence data were demultiplexed using CASAVA, and reads were aligned to the reference human genome (hg19) using BWA and postprocessed using the Genome Analysis Toolkit (GATK) according to GATK best practices.

MuTect and GATK were used to call single-nucleotide variants and small indels, respectively. Exon-level copy number gains and losses were inferred from the ratio in Tumour:Normal sequence coverage for each target region, following a loss-normalization to adjust for the dependency of coverage on GC content.

6.2 Results

PIK3CA is mutated in approximately half of uterine cancers. To investigate the role of PIK3CA oncogenicity in this organ, we took advantage of the previously reported Rosa26-LSL-PIK3CAH1047R transgenic strain that allows the expression of the PIK3CA H1047R mutation in a tissue-specific manner using the Cre-loxP technology. These animals were crossed with the Sprr2f-Cre strain, which has been shown to drive the expression of the Cre recombinase in both luminal and glandular epithelial cells of the uterus. Unexpectedly, while PIK3CASprr2f-WT mice were viable and normal, PIK3CASprr2f-Cre littermates showed hind limb paresis at early ages (4-10 weeks) affecting both males and females. Histological examination of these tissues revealed lesions in the spinal cord that resembled vascular malformations (VM) found in humans. Specifically, the abnormalities found presented multifocal hemorrhage infiltrated by moderate amounts of fibrin and plump fibroblasts. These hemorrhages, present in both white and grey matter, were the result of extensive dilated meningeal blood vessels that shattered, presumably, due to the mechanical stress of the area, and leaked blood on the parenchyma. Through intravenous injection on both control PIK3CASprr2f-WT and PIK3CASprr2f-Cre littermates with a gold nanoparticle contrast and X-ray computed tomography imaging, we confirmed the presence of hyperdense lesions at the thoracic level of the spine, which were present not only in animals with advanced paresis but also in animals with a milder phenotype indicating blood extravasation and poor blood flow. These lesions arising in our model highly resembled human spinal VM, as confirmed by pathological examination.

Alterations in blood vessels were present in other organs including lung, adrenal gland, epididymis, and skin. Vascular ectasia was histologically consistent with venous hemangiomas according to the WHO classification in Soft Tissue Tumors. According to the ISSVA, these lesions are now considered simple VM, with the absence of associated outgrowth such as CLOVES syndrome or Fibroadipose hyperplasia, in which PIK3CA mutations have been reported. Among the vascular abnormalities, dermal VM were frequent, with high penetrance in the PIK3CASprr2f-Cre mice. Microscopically, the skin lesions resembled human VM, with differentiated spindle cells positive for the CD31 endothelial-specific staining; hemosiderin deposition on the dilated lumens due to erythrocyte rupture; and positivity for Prussian blue staining.

From a clinical perspective, a particularly critical issue is to distinguish the VM from the vascular tumors, especially in the case of Infantile Hemangioma (IH). This categorization is of important significance in the treatment and prognosis of the patients and, therefore, several biomarkers have been optimized on immunohistochemical assays to differentiate each vascular anomaly. Among them, GLUT-1 and WT-1 are the most widely accepted, showing high positivity in IH cases but resulting negative on VM. In order to identify the precise abnormality that our mouse model represents, we assessed GLUT-1 and WT-1 staining in the lesions and found that both markers were negative as compared to the immunoreactivity detected in IH patients. Moreover, the VM found on mice do not exhibit positivity for LYVE-1 staining, a robust marker of lymphatic vessels, which supports the notion that these lesions are mainly VVM. Through LacZ staining using the Rosa26-LSL-LacZ crossed with our Sprr2f mouse model, we confirmed that Sprr2f promoter drives the expression of Cre recombinase in endothelial cells likewise in endometrial luminal and glandular epithelial cells.

Figure 1C:
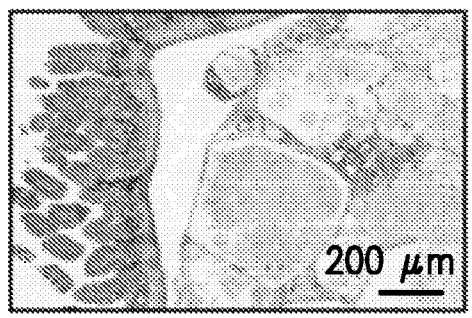
Figure 1D:
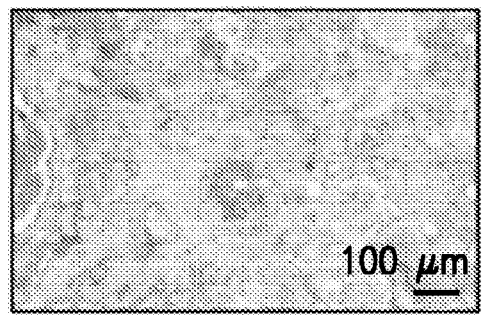
Figure 1E:
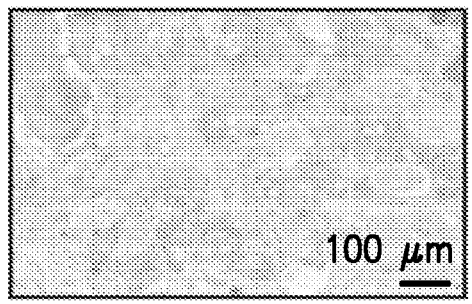
Figure 1F:
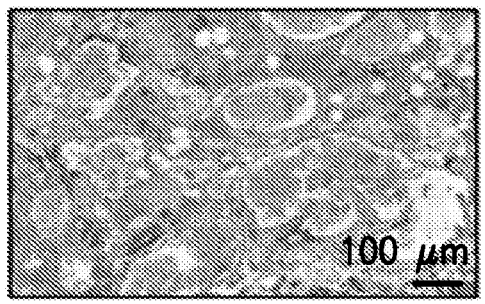
Figure 2A:
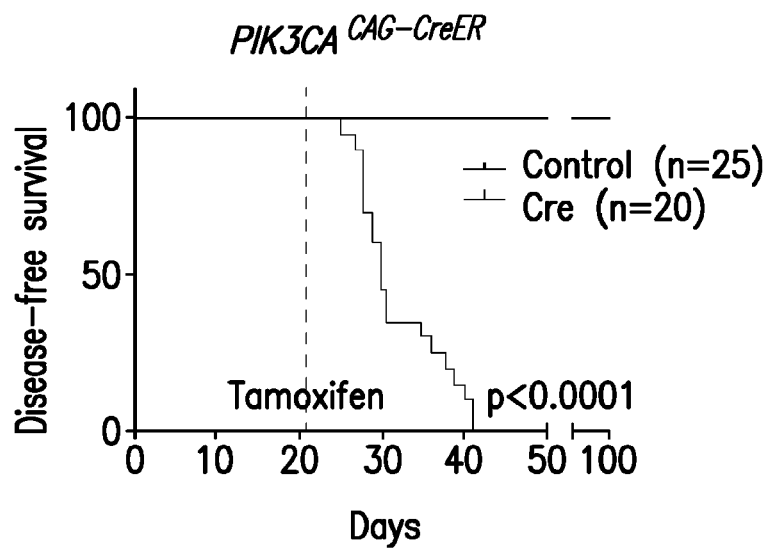
Figure 2B:
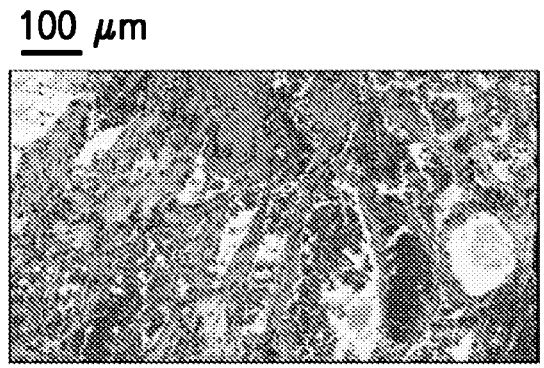
Figure 2C:
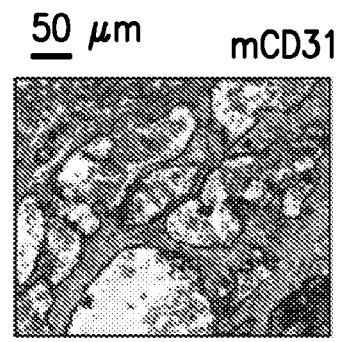
Figure 2D:
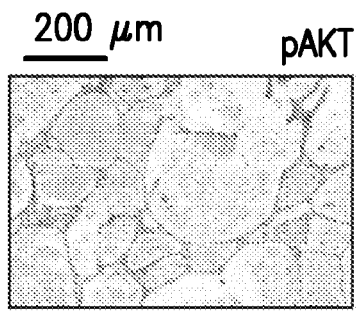
Figure 2E:
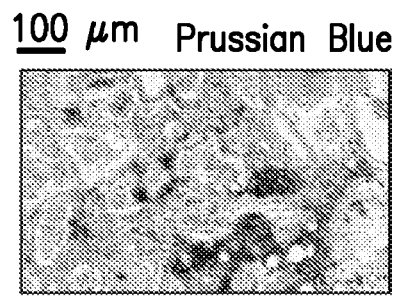
Figure 2F:
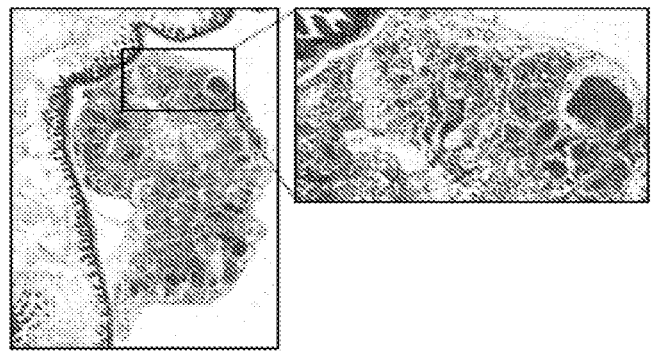
Figure 2G:
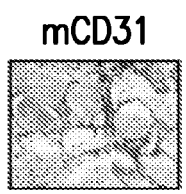
Figure 2H:
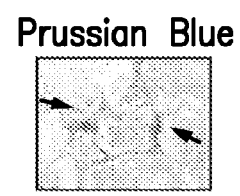
Figure 2I:
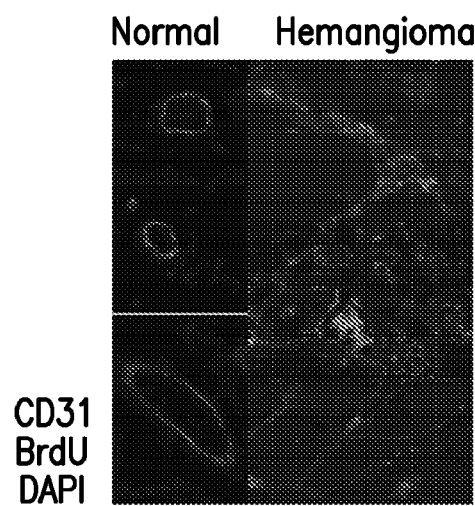
Figure 3A:
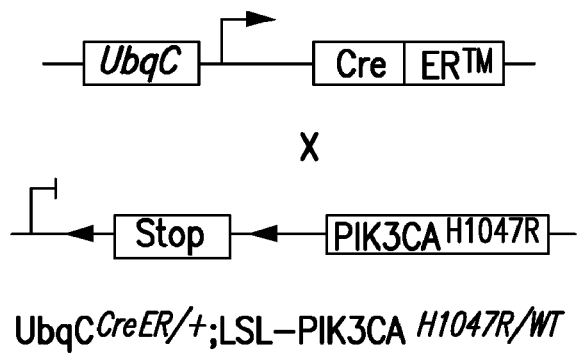
Figure 3B:
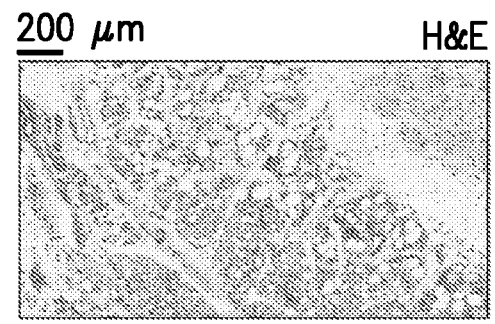
Figure 3C:
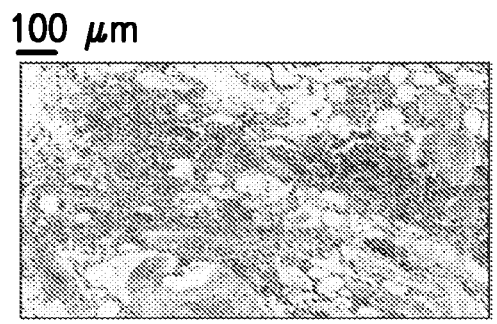
Figure 3D:
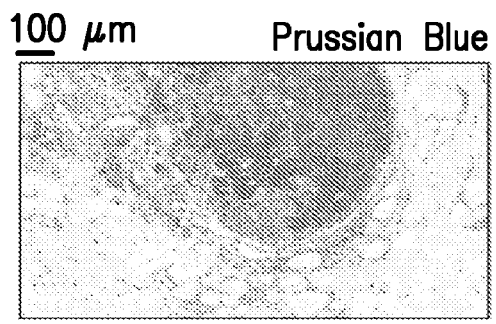
Figure 3E:
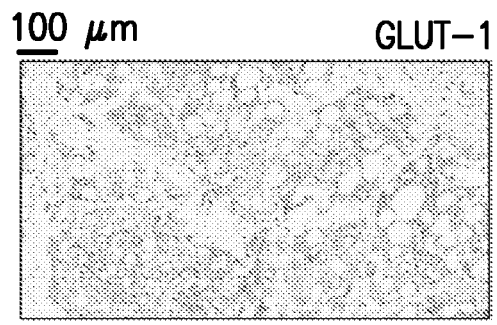
Figure 3F:
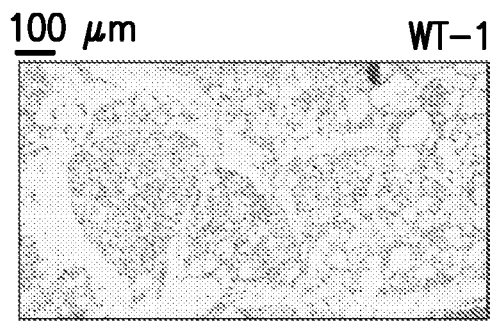

Next, we hypothesized that endothelial cells might be particularly sensitive to oncogenic PIK3CA transformation as we had noticed in the PIK3CASprr2f-Cre model, and in agreement with previous observations. To test this, we generated PIK3CA$^{CAG-CreER}$ mice (FIG. 1A), in which the PIK3CA H1047R mutation is ubiquitously expressed upon tamoxifen administration. Six to eight week old mice fed with tamoxifen rapidly developed cutaneous VM as compared to the PIK3CAWT littermates (FIG. 2A). Histology of the skin lesions revealed VM that combined capillary and venous phenotypes (FIG. 2B). Consistently, the VM were immunoreactive to CD31 staining (FIG. 2C) and phosphorylated AKT (S473), a surrogate marker of PI3K activation (FIG. 2D). Similar to human patients, VM were not reactive to the IH markers GLUT-1 and WT-1 (FIG. 1 D,E), contained high levels of hemosiderin (FIG. 2E), and were negative for LYVE-1 (FIG. 1F). Although the skin phenotype was drastic and more visible, necropsy of these animals also revealed the presence of internal VM, which affected but were not restricted to mesenteries, genitourinary tract, kidneys, and retinas. Histology of these lesions revealed large cavities containing blood and multilayered endothelial cells that were consistently positive for CD31 and Prussian blue staining (FIGS. 2F-H), and negative for GLUT-1, WT-1, and LYVE-1. The vascular ectasia and LYVE-1 negativity, together with their gross appearance, indicate that these lesions are venous malformations.

These findings were further confirmed using the UBC-CreER strain, in which the Ubiquitin C promoter drives the expression of the tamoxifen-inducible Cre-recombinase (FIG. 3A-F). Consistently, our results indicated that upon ubiquitous expression of the oncogenic PIK3CA transgene, endothelial cells were more sensitive than other cell types to be transformed and give rise to VM.

PI3K signaling has been extensively shown to enhance proliferation. However, it is not clear whether VM are a result of increased proliferation, cell size, or alterations in cell fate. In order to test this in our mouse model, we analyzed BrdU incorporation in both PIK3CAWT and PIK3CACAG-CreER littermates. While normal blood vessels are negative for BrdU incorporation as a result of quiescence, VM have an increased number of BrdU+ cells (FIG. 2I), along with increased Ki67 staining (FIG. 1C). Moreover, since PIK3CA mutations are oncogenic in vivo in epithelial cells, we asked if endothelial cells could exhibit a similar behavior. PIK3CA$^{CAG-CreER}$ VVM cells injected into recipient immune-compromised nude mice exhibited highly vascularized proliferative tumors few weeks after injection, with a histology highly resembling that of the original VVM. This finding confirmed the tumorogenicity of this so far considered hamartomas. In order to emphasize the clinical relevance of these findings, we treated the VVM with BYL719 (50 mg×kg-1; daily p.o.), a PI3Kα inhibitor currently in clinical trials. Tumors exhibited a decrease in volume upon treatment (FIG. 1B) that was consistent with a decrease in phospho-AKT (S473) and phospho-S6RP (S240/4) levels, along with a decrease in proliferation and increased apoptosis. Altogether, our results indicate that VVM from this mouse model have tumorigenic potential and that treatment with PI3K inhibitors is a suitable pharmacological approach to control the disease.

Figure 4A:
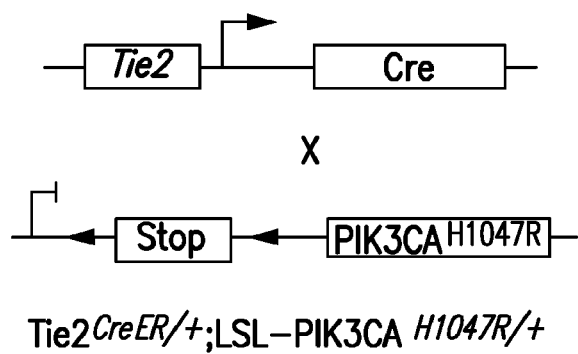
Figure 4B:
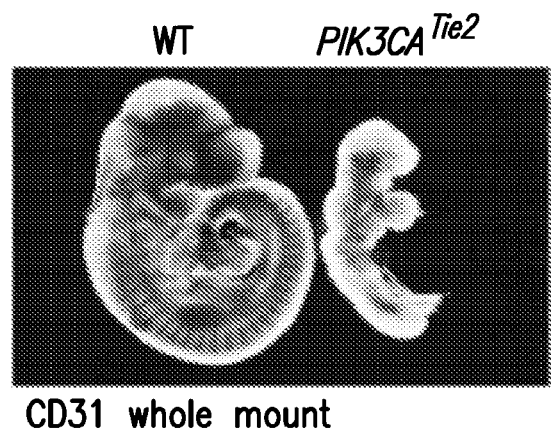
Figure 4C:
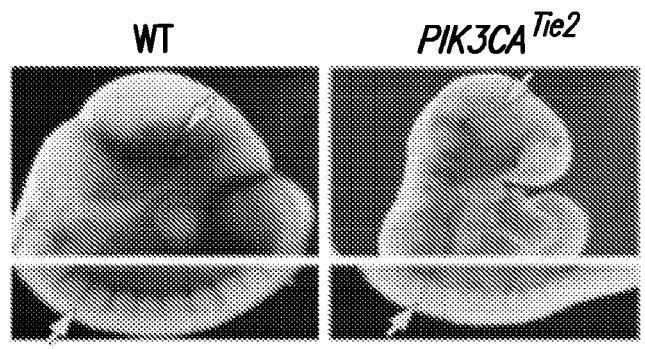
Figure 4D:
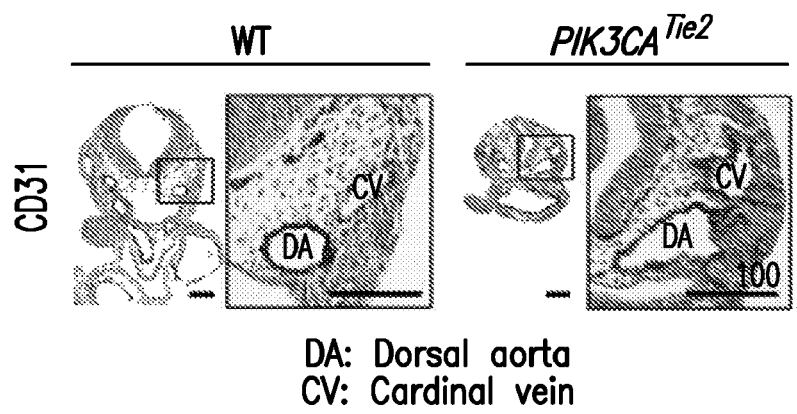

Vascular malformations may occur as a result of defects during the process of angiogenesis, a process in which PI3Kα is actively involved. To explore the biological significance of PI3K hyperactivation specifically in blood vessels we expressed the PIK3CA H1047R transgene under the control of the Tie2 promoter using the Tie2-Cre strain (FIG. 4A). PIK3CATie2-Cre mice were not viable due to early embryonic lethality (E-10) as a result of cardiovascular defects (FIG. 4B). CD31 staining of coronal sections revealed enlarged blood vessels and morphological anomalies in vascular formation (FIG. 4C, upper panel). As a matter of fact, the lesions were present in meningeal vessels, cardinal vein, and dorsal aorta. Moreover, small intersomitic vessels also failed to form (FIG. 4C, lower panel), suggesting that normal levels of PI3K activity are required for small vessel formation and homeostasis. These malformations were also evident in whole-mount embryo CD31 staining, where we observed aberrant formation of the cephalic veins and the intersomitic vessels (FIG. 4B). Vascular precursors of PIK3CA$^{Tie2-Cre}$ mice were englarged and disorganized (FIG. 4D). Apoptosis and proliferation was not altered in the heart of PIK3CATie2-Cre embryos suggesting that the observed phenotype is indeed due to a defect in the process of blood vessels formation.

Figure 4E:
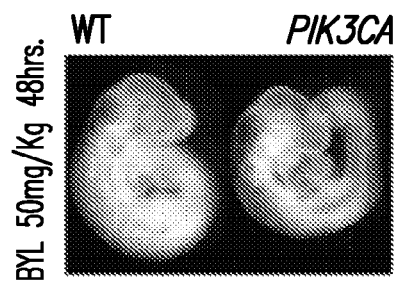
Figure 4F:
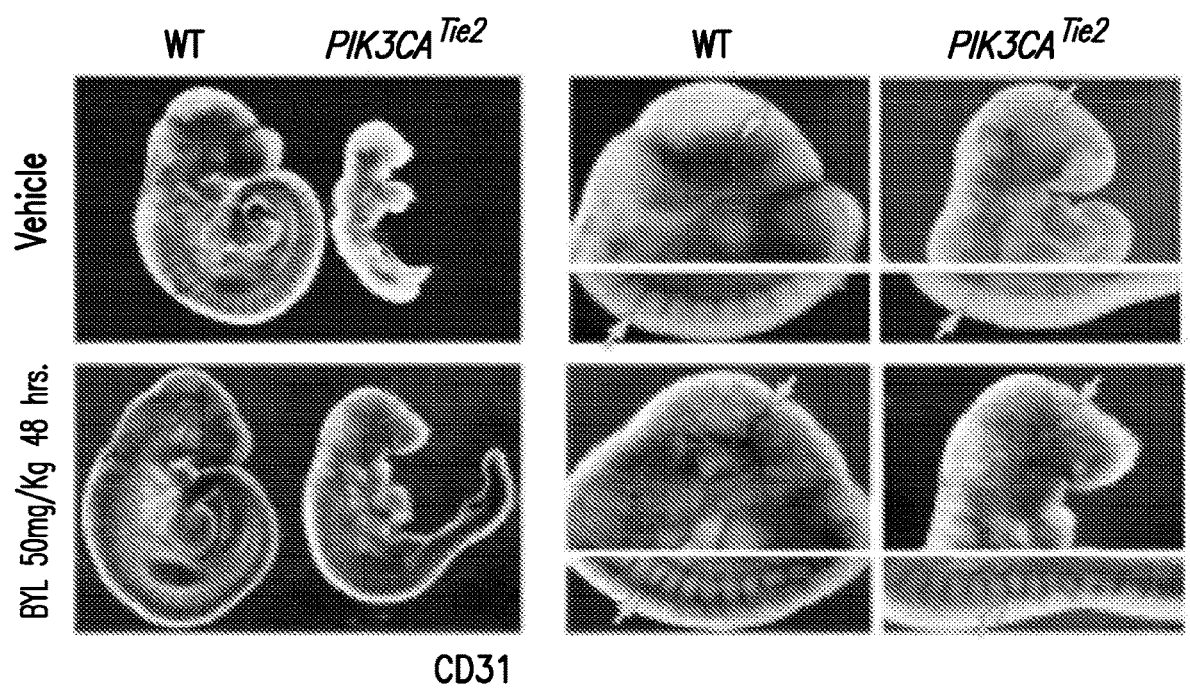

Aiming to validate the implication of excessive PIK3CA signaling in aberrant blood vessel formation, as well as to evaluate the potential for pharmacological inhibition to overcome this effect, we attempted to revert the phenotype by treating pregnant mice with a PI3Kα inhibitor. Treated PIK3CATie2-Cre E9.5 embryos showed an overall body-size comparable to PIK3CAWT littermates, suggesting an improved cardiovascular function (FIG. 4E). Consistently, CD31 whole-mount staining revealed restored cephalic small blood vessel formation, as well as intersomitic vessels (FIG. 4F). Phospho-AKT staining showed a strong reduction in both PIK3CATie2-Cre and PIK3CAWT embryos after PI3Kα inhibitor treatment, in contrast with untreated control embryos. At the histological level, we found that treatment reestablished enlarged meningeal, cardinal vein, and dorsal aorta blood vessels, indicating that aberrant PI3K hyperactivation directly impairs normal embryonic angiogenesis in mice.

To further study the cellular mechanism by which PIK3CA mutations alter the normal biology of endothelial cells, primary human skin endothelial cells were transduced with PIK3CA WT or H1047R mutant expressing vectors. Mutant cells exhibited an increase in downstream PI3K signaling and failed to generate normal tubes in vitro. PI3K mutant cells also proliferated at a higher rate than WT cells and had increased cell size.

Finally, in order to address if the phenotype observed in our mouse and cell models is also involved in the human pathogenesis, we collected samples from VVM patients (n=30). All samples where confirmed clinically and histologically to be pure VVM and negative for the markers GLUT-1 and WT-1. One such lesion is shown as a radiographic image (FIG. 5A) and corresponding histological study (FIG. 5B). Due to the low cellularity of these lesions, we took advantage of a previously described high-throughput targeted-exome sequencing platform (IMPACT) yielding a median coverage of 570X. Deep sequencing allowed the detection of PIK3CA mutations in 30% of the cases in previously described hot spots (H1047R, E542K, E545K). In addition, we found mutations in other genes related with the PI3K pathway (FIG. 5D) such as AKT2, AKT3, and IRS2, resulting on 50% of the examined patients being affected by gain-of-function mutations on the PI3K/AKT pathway (FIG. 5C). Amplifications of PIK3CA and PTEN deletions are also frequent events in cancer, however we did not find any of these alterations by means of FISH in a cohort of 40 VVM patients.

In summary, our study provides the first animal model recapitulating human VVM caused by abnormal hyperactivation of the PI3K/AKT pathway; demonstrates the tumorigenic nature of the disease; and reveals the impact of PIK3CA mutations in the pathogenesis of pure VVM that are not associated with overgrowth or germline mutations, providing a therapeutic opportunity to treat these patients.

7. EXAMPLE 2: SOMATIC PIK3CA MUTATIONS AS A DRIVER OF SPORADIC VENOUS MALFORMATIONS 7.1 Materials and Methods
Study Design.

This study was designed to confirm the effect of PIK3CA H1047R expression in the genesis of vascular malformations (VM). The prevalence of PIK3CA mutations in human specimens of VM were characterized using targeted next-generation sequencing. The cohort of patients was obtained from Memorial Sloan-Kettering Cancer Center (US) and from the Hospital de la Santa Creu i Sant Pau (Spain) and were reviewed by a board-certified pathologist (C.R.A). All patients provided informed consent. The findings were further confirmed using different mouse models that drive the expression of the PIK3CA transgene in a ubiquitous-dependent manner. For these experiments, cohorts of n=45 mice were used. Littermates were used as a control. Disease-free survival plots were analyzed using the Mantel-Cox Log-rank test. For efficacy studies with different inhibitors, animals were randomized with at least n=8-10 tumors/arm. Student's t test was used to assess the statistical differences between the treatments and control arms.

Mice.

The following mouse strains were obtained from The Jackson Laboratories: R26-LSL-PIK3CA$^{H1047R}$ (016977), CAG-CreER (017595), Tie2-Cre (004128), and UBC-CreER (008085). The Sprr2f-Cre strain (01XNA) was acquired from the National Cancer Institute (NCI) Mouse Repository and was previously described (19). The R26-LSL-LacZ reporter strain was available at the Mouse Transgenic Core of MSKCC.

Mice were housed and maintained in a controlled environment at the Research Animal Resource Center (RARC) of MSKCC and all procedures were performed in accordance with Institutional Guidelines under the protocol number 12-10-019. Tamoxifen (Harlan; TD.130856) was administered through the food chow at approximately 40 mg×kg$^{-1}$. In all the experiments using mice, WT littermates were used as a control.

For allograft studies, vascular lesions isolated from PIK3CA$^{CAG-CreER}$ mice were rinsed with ice cold PBS, minced, resuspended with cold 1:1 DMEM/Matrigel, and injected subcutaneously in six-week-old female athymic Foxn1$^{nu}$ nude mice. Once VM reached a volume of 250-350 mm$^3$, mice were treated using the PI3Kα inhibitor BYL719 (Chem Express; 25 mg×kg$^{-1}$ in 0.5% carboxymethylcellulose (Sigma), daily p.o.), everolimus (SU2C; 10 mg×kg$^{-1}$ in PBS, daily p.o.), or propranolol (Sigma; 40 mg×kg$^{-1}$ in PBS, daily p.o.), over 7 days. Propranolol dose was chosen based on the FDA guidelines for the conversion of animal doses to Human Equivalent Doses (HED) using the dose previously described for Infantile Hemangioma (23) (6 mg×kg$^{-1}$) as a reference. The following formula was applied:

$$HED(\text{mg} \times \text{kg}^{-1}) = \text{mouse dose}(\text{mg} \times \text{kg}^{-1}) \times \left(\frac{\text{mouse weight (kg)}}{\text{human weight (kg)}}\right)^{0.33}$$

After one week of treatment, VM were measured and harvested for further analysis. VM volume was calculated using the following formula:

$$VM \text{ volume (mm}^3) = \frac{\text{width (mm)}^2 \times \text{length (mm)}}{2}$$

For the treatment of pregnant PIK3CA$^{Tie2-Cre}$ mice, BYL719 was administered orally three times at E7.5, E8.5, and E9.5. Two hours after the last treatment, embryos were harvested and characterized.

For the formulation of topical preparations, the cream base Versatile™ (Fargon) was used, which allows the incorporation of active principles and has the ability to vanish rapidly into the skin of the mice. Two different formulations using BYL719 at 1% (w/w) were prepared as follows. Free BYL719: This formulation was generated by mixing BYL719 in powder with the base cream and homogenized using an Ultra-Turrax to achieve a similar distribution of the active principle. Soluble BYL719: For this formula, BYL719 powder was dissolved in a small volume of DMSO (400 mg×mL$^{-1}$). This concentrated solution was then incorporated into the base cream with gentle agitation, achieving a homogeneous distribution of the active principle. The topical formulations were applied into the mice lesions at daily-basis and VM growth was assessed as described above.

Histology and IHC.

Mice and human tissue was fixed, dehydrated, paraffin-embedded, sectioned at 5 microns and H&E-stained using standard histology protocols.

Prussian blue staining was performed incubating deparaffinized tissue sections in a mixture of 20% hydrochloric acid aqueous solution and 10% aqueous solution of potassium ferrocyanide over 20 minutes. Slides were washed three times using distilled water and counterstained using Nuclear Fast Red staining.

For LacZ staining, mouse tissue was fixed using a solution containing 0.2% glutaraldehyde, 1% formaldehyde and 0.02% NP-40 in PBS for 1 h at 4° C. After washing, tissue was incubated in X-gal staining solution (5 mM K$_3$Fe(CN)$_6$, 5 mM K$_4$Fe(CN)$_6$ and 2 mM MgCl$_2$, 1 mg/ml X-gal in PBS) overnight at room temperature. For histology, LacZ stained tissues were fixed in 3.7% formaldehyde-PBS and embedded in paraffin, sectioned and counterstained with Nuclear Fast Red staining.

IHC and IF stainings were performed using Discovery XT processor (Ventana Medical Systems) at the Molecular Cytology Core (MSKCC). Tissue sections were deparaffinized with EZPrep buffer (Ventana Medical Systems), antigen retrieval was performed with CC1 buffer (Ventana Medical Systems). Sections were blocked for 30 minutes with Background Buster solution (Innovex) or 10% normal rabbit serum (for LYVE-1 antibody) followed by avidin/biotin blocking for 8 minutes. Sections were stained with the following antibodies: CD31: (Dianova, DIA-310, 1 μg×mL$^{-1}$) for 5 hours, followed by 60 minutes incubation with biotinylated goat anti-rat IgG (Vector labs, PK-4004) at 1:200 dilution. The detection was performed with Streptavidin-HRP D (Ventana Medical Systems), followed by incubation with Alexa Fluor 488 (Invitrogen, T20922); BrdU: sections were pretreated with Protease K (5 μg×mL$^{-1}$) and incubated with anti-BrdU (Roche, 1170376, 1 μg×mL$^{-1}$) for 5 hours, followed by 60 minutes incubation with biotinylated horse anti-mouse IgG (Vector Labs, MKB-22258). The detection was performed with Streptavidin-HRP D (Ventana Medical Systems), followed by incubation with Alexa Fluor 594 (Invitrogen, T20935). When two markers were used, stainings were performed consecutively according to the procedure described above. After staining, slides were counterstained with DAPI (Sigma, D9542, 5 μg×mL$^{-1}$) for 10 min and coverslipped with Mowiol. Antibodies were used as follows: GLUT-1: Sections were incubated with anti-GLUT-1 antibody (Chemicon, AB1340, 0.5 μg×mL$^{-1}$) for 4 hours, followed by 60 minutes incubation with biotinylated goat anti-rabbit IgG (Vector labs, PK6101) at 1:200 dilution; LYVE-1: Sections were incubated with anti-LYVE-1 antibody (R&D Systems, AF2125, 1 μg×mL$^{-1}$) for 3 hours, followed by 60 minutes incubation with biotinylated rabbit anti-goat IgG (Vector, BA-5000) at 1:200 dilution.; and WT-1: Sections were incubated with anti-WT-1 antibody (Abcam, Ab89901, 1:50 dilution) for 1 hour, followed by 60 minutes incubation with biotinylated rabbit anti-goat IgG (Vector, BA-5000) at 1:200 dilution. For GLUT-1, LYVE-1, and WT-1 IHC, detection was performed with DAB detection kit (Ventana Medical Systems) according to manufacturer instructions, followed by counterstaining with hematoxylin (Ventana Medical Systems) and coverslipped with Permount (Fisher Scientific).

All slides were scanned using Mirax Midi Slide Scanner (Zeiss). An expert sarcoma pathologist (C.R.A.) reviewed the histology for mice and humans.

microCT Scan.

For microCT scan, mice were injected in the tail vein using gold nanoparticles (1115, AuroVist™). Two hours post-injection mice were anesthetized using isoflurane. The cone beam microCT scans were acquired on a Nano SPECT/CT Plus™ system (Mediso). Each scan averaged approximately 5 minutes using 240 projections with an exposure time of 1,000 ms and angular increment of 1 degree. The X-ray tube voltage and current were 55 kVp and 145 mA, respectively. The reconstructed voxel dimensions were 73×73×73 mm. Images were reconstructed and analyzed using the InVivoScope™ software provided on the Nano SPECT/CT Plus.

Cell-Based Assays.

Human dermal EC (endothelial cells) were derived from healthy face skin tissue and were a gift from Dr. Joyce E. Bischoff (Boston Children's Hospital). EC were maintained in supplemented EBM-2 media (CC-3162) following the manufacturer protocol. EC were transduced with the retrovirus pBabe-EV, pBabe-PIK3CA (WT), and pBabe-PIK3CA (H1047R), obtained from Addgene (ID: 1764, 12523, and 12524 respectively). Briefly, GP2-293 (Clontech) cells were transiently co-transfected with retroviral pBabe and CMV-VSV-G plasmids. 48 h post transfection supernatants were harvested, supplemented with 8 μg×mL$^{-1}$ of polybrene, and used to infect EC. 48 h post infection EC were selected using 0.5 μg×mL$^{-1}$ of puromycin.

Proteins were extracted using RIPA buffer and Western blot was performed usim standard methods. Antibodies for Western blot were: pAKT (S473) (Cell Signaling; 4060), pAKT (T308) (Cell Signaling; 2965), AKT (Cell Signaling; 9272), pS6K (T389) (Cell Signaling; 9205), S6K (Cell Signaling;

2708), pS6 (S240/4) (Cell Signaling; 5364), pS6 (S235/6) (Cell Signaling; 4858), S6 (Cell Signaling; 2217), actin (Cell Signaling; 4970). Tube formation assay was performed using Matrigel-coated 48 multiwells as a substrate. $10^5$ EC were seeded in EBM-2 media without FBS and analyzed after 6 hours for tube formation.

For EdU incorporation, cells were serum-starved overnight and labeled for 4 h using the Click-iT® EdU Alexa Fluor® 488 Flow Cytometry Assay Kit (C-10425) following manufacturer instructions. Flow cytometry was performed using FACSCalibur (BD Bioscience).

Patients.

Thirty-two archival samples from sporadic VM patients were collected for the sequencing study. Age, gender, and localization of the lesions are detailed in FIG. 16. All patients provided informed consent and were sequenced under the MSKCC IRB protocol number 02-060. When required, samples were microdissected to increase the cellular content. All samples were GLUT1 and WT1 negative by IHC. DNA was isolated using the QIAamp DNA FFPE Tissue Kit (Qiagen).

Targeted Exome Sequencing (MSK-IMPACT).

MSK-IMPACT was performed as previously described (26). Briefly, DNA derived from 36 venous malformation patients was further subjected to deep-coverage targeted sequencing of 341 key cancer-associated genes. MSK-IMPACT (Integrated Mutation Profiling of Actionable Cancer Targets), involves hybridization of barcoded libraries to custom oligonucleotides (Nimblegen SeqCap) designed to capture all protein-coding exons and select introns of 341 commonly implicated oncogenes, tumour suppressor genes, and members of pathways deemed actionable by targeted therapies. Barcoded sequence libraries were prepared using 100-250 ng genomic DNA (Kapa Biosystems) and combined into equimolar pools of 13-21 samples. The captured pools were subsequently sequenced on an Illumina HiSeq 2000 as paired-end 100-base pair reads, producing a median of 588-fold coverage per tumor.

Sequence data were demultiplexed using CASAVA, and reads were aligned to the reference human genome (hg19) using BWA and postprocessed using the Genome Analysis Toolkit (GATK) according to GATK best practices.

MuTect and GATK were used to call single-nucleotide variants and small indels, respectively. Candidate mutations were manually reviewed using the Integrative Genomics Viewer (IGV) to eliminate likely false positive calls. Because matched normal DNA was not available, tumors were compared to a pool of 10 unmatched normal samples to eliminate common polymorphisms and systematic sequencing artifacts. Additional sequence variants detected in the 1000 Genomes Project in >1% of individuals were flagged as likely germline. It was observed that all variants detected at known somatic mutation hotspots (e.g., PIK3CA H1047R) had mutant allele fractions between 3 and 20%, supporting that observation that the tumor purities were relatively low. Consequently, it was speculated that novel sequence variants observed in >40% of reads were possibly germline mutations.

Because TEK is not included in the MSK-IMPACT assay, the libraries from IMPACT were recaptured using specific probes targeted against TEK (Integrated DNA Technologies). Bait sequences used are available upon request. Captured pools were sequenced and analyzed as described above.

FISH.

FISH analysis was performed on whole paraffin sections and Tissue Microarray (TMA) using a three-color probe mix as described: PIK3CA (3q26.32) (Red; clone RP11-682A21, RP11-737O18,RP11-959N23); PTEN (10q23) (Orange; clone RP11-380G5, RP11-165M8); Control (3p11-12) (Green; clone RP11-312H1, RP11-81P15).

Clone DNA was labeled by nick translation using fluorochrome-conjugated dUTPs (Enzo Life), supplied by Abbott Molecular Inc. Hybridization, post-hybridization washing, and fluorescence detection were performed according to standard procedures. Slides were scanned using a Zeiss Axioplan 2i epifluorescence microscope equipped with a megapixel CCD camera (CV-M4+CL, JAI) controlled by Isis 5.2 imaging software (Metasystems). The entire section was scanned under 63× objective to assess the quality of signal hybridization and representative regions imaged through the depth of the tissue (compressed/merged stack of 12 z-section images taken at 0.5 µm intervals under the Red, Green, and Orange filter respectively). For each case/core, a minimum of 2-6 captured image fields (>50 cells) were selected and signals enumerated. To obtain copy number (mean signal) per cell, the total number of signals for each gene/locus was divided by the total number of cells within the field(s). Only intact cells and cells with at least one signal each for $\frac{2}{3}$ loci were selected. Cut-off values for copy number gain and loss were established from the control samples (normal hepatic tissue and placental tissue). Amplification of PIK3CA was defined as, PIK3CA: Control ratio of ≥2.0 or >10 PIK3CA copies independent of control locus. Cells with 3~5 copies and 6~10 copies were considered to be polysomic and high-polysomic, respectively. A mean signal of ≤1.0 copies/cell was considered as true loss of PTEN or PIK3CA.

7.2 Results

Figure 6A:
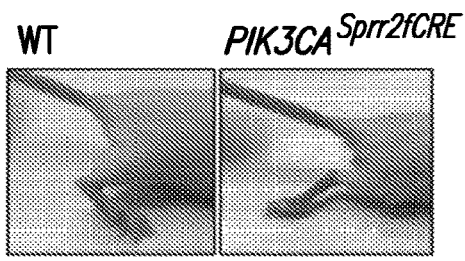
Figure 6B:
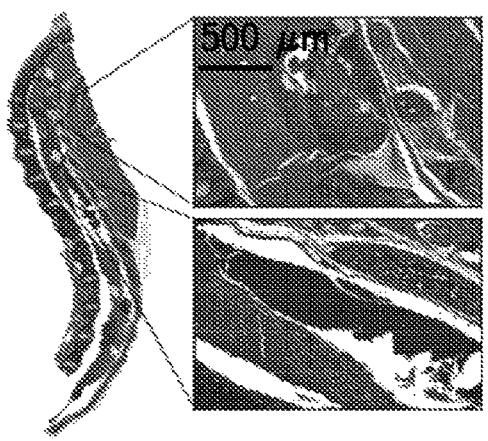
Figure 6C:
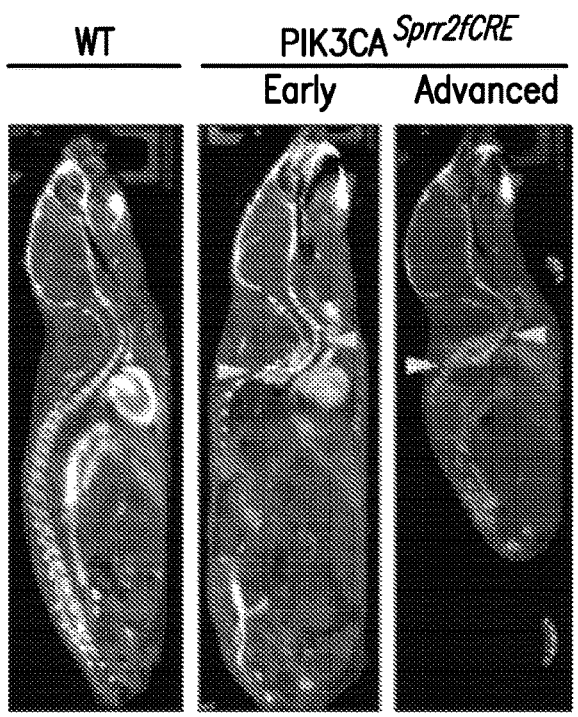

PIK3CA$^{Sprr2f\text{-}Cre}$ mice develop spinal and cutaneous VM. An unexpected suggested a critical role of phosphoinositide 3-kinase (PI3K) in the pathogenesis of VM. Initially, this study was focused on the role of PIK3CA, the gene encoding the catalytic p110α subunit of PI3K (PI3Kα), in uterine cancer, which is characterized by the presence of these mutations in approximately half of the cases (17). To investigate the role of PIK3CA oncogenicity in this disease, the previously reported transgenic mouse strain LoxP-STOP-LoxP (LSL)-PIK3CA$^{H1047R}$, which allows the expression of the activating PIK3CA mutation H1047R in a tissue-specific manner using the Cre-loxP technology upon removal of the floxed synthetic transcriptional/translational STOP cassette was used (18). These animals were crossed with the Sprr2f-Cre strain, shown to drive Cre recombinase expression in both luminal and glandular uterine epithelial cells (19) (FIG. 11A). Unexpectedly, while PIK3CA$^{Sprr2f\text{-}WT}$ mice were viable and normal, PIK3CA$^{Sprr2f\text{-}Cre}$ littermates exhibited hind limb paralysis at an early age (4-10 weeks) (FIG. 6A). Because this phenotype was observed in both males and females, the pathologic events underlying this phenotype were further explored. Histologic examination revealed lesions in the spinal cord resembling human vascular malformations. Specifically, these abnormalities showed dilated 'cavernous' vascular spaces with extensive blood pools (FIG. 6B) and hemorrhage involving both white and grey matter.

The spinal lesion of these mice were examined using intravenous injection of gold nanoparticles in PIK3CA$^{Sprr2f\text{-}Cre}$ mice and confirmed the presence of hyperdense lesions in the spine by contrast and X-ray computed tomography imaging. These lesions were present in animals with both advanced and milder phenotype (FIG. 6C), showing rheological slow blood flow and extravasation.

Figure 6D:
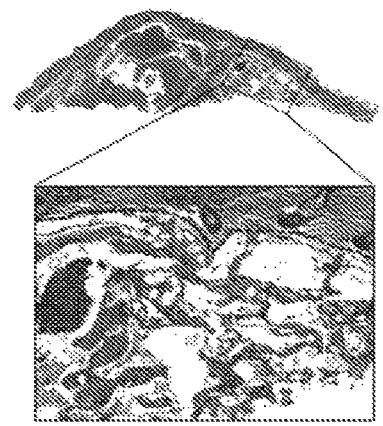
Figure 6E:
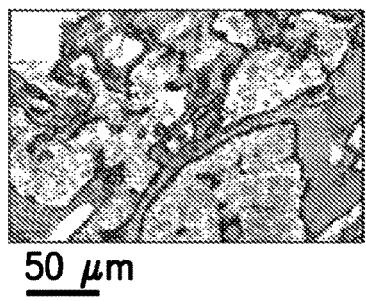
Figure 6F:

Blood vessel alterations were also detected microscopically in other organs including lung, adrenal gland, epididymis, and skin. These abnormal vascular channels, represented by cavernous spaces and capillary proliferations, were consistent with a diagnosis of VM according to the current classification of the International Society for the Study of Vascular Anomalies (20). Among these, skin VM were frequent, with high penetrance in the PIK3CA$^{Sprr2f-Cre}$ mice (FIG. 6D). Microscopically, the skin lesions resembled human VM with positivity for CD31 (FIG. 6E) and Prussian blue (FIG. 6F) stainings indicative of endothelial lining and hemosiderin deposition, respectively.

To further characterize the observed lesions, the mouse VM for both GLUT-1 and WT-1, which are markers of Infantile Hemangioma (6H), a different vascular disease with a unique natural history that responds to the β-blocker propranolol were stained (21-23). Both stainings were negative as compared to positive controls (FIG. 11B-E). Lymphatic malformations have been previously shown to harbor PIK3R1 and PIK3CA mutations (24). Thus, in order to assess whether the VM model might exhibit any lymphatic component, the lesions were stained stained for the lymphatic-specific marker LYVE-1 (25), and no reactivity was detected indicating that these lesions are pure VM (FIG. 11F).

It was hypothesized that the Sprr2f-Cre strain drives the expression of the Cre recombinase in EC, in addition to the endometrial epithelial cells. The LSL-LacZ reporter strain crossed with the Sprr2f-Cre mouse were used and β-galactosidase staining was performed in spinal sections. The presence of discrete positive cells sparsely distributed within the white and grey matter of the spinal cord resembling EC was detected (FIG. 11G). Unfortunately, due to technical constrains double stainings for LacZ and CD31 were not obtained. Therefore, the VM from the Sprr2f-Cre mice were stained for double immunofluorescence against Cre and CD31. This confirmed the presence of Cre recombinase in the CD31-positive lesions, explaining the vascular phenotype observed in these mice (FIG. 11H).

PIK3CA activating mutation affects normal endothelial cells. Analogous to recent studies (11), and in order to study the cellular mechanisms by which PIK3CA mutations might alter EC function, primary human skin EC (HF SEC cells) were transduced with retrovirus encoding for the PIK3CA WT or H1047R variants.

Figure 7A:
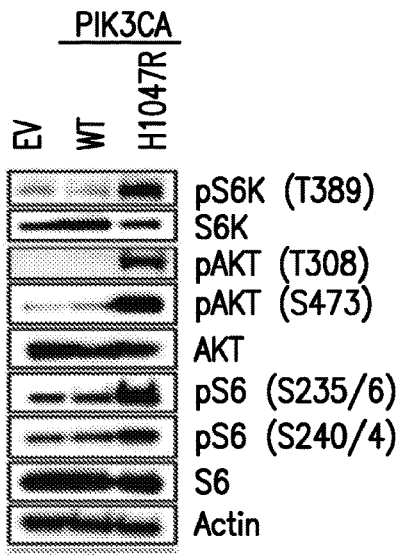
Figure 7B:
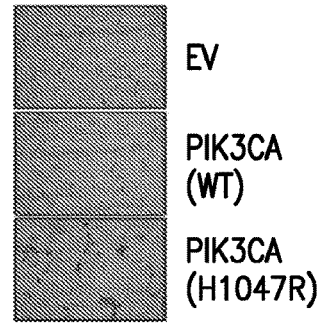
Figure 7C:
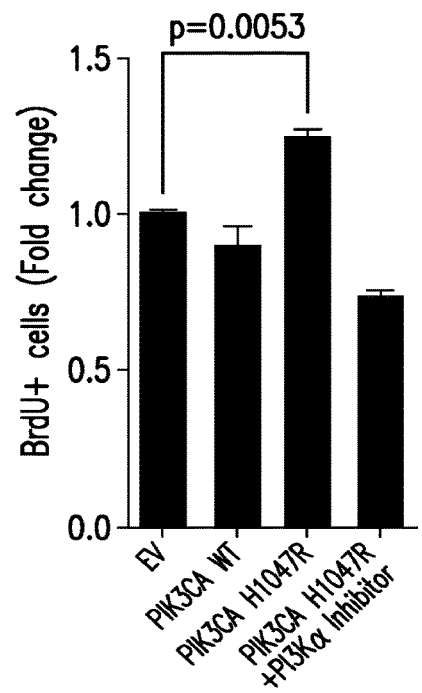

PIK3CA H1047R mutant cells exhibited amplified downstream PI3K/AKT/mTOR signaling with increased phosphorylation of AKT at S473 and T308, and the mTOR downstream targets S6-kinase at T389 and ribosomal S6 protein at S235/6 and S240/4 (FIG. 7A). Moreover, we undertook tube formation assays to assess the ability of these cells to form a normal capillary network in a 3D matrix. PIK3CA H1047R mutant cells formed aberrant EC clusters as opposed to the WT counterparts that generated normal vascular tubes in vitro (FIG. 7B). The proliferation ratio of these cells in vitro using EdU incorporation assays were also tested and it was found that the mutant cells exhibited a slightly higher proliferation rate as compared with WT and empty-vector cells, which was reversed upon treatment with a PI3Kα inhibitor (FIG. 7C).

Figures 7D, 7E:
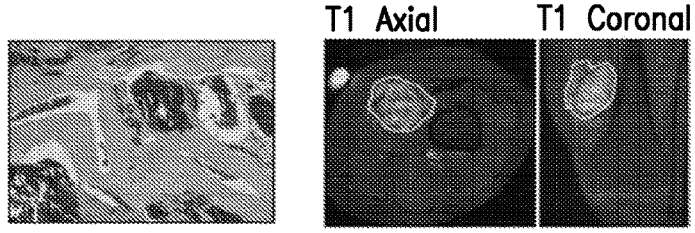
Figure 7F:
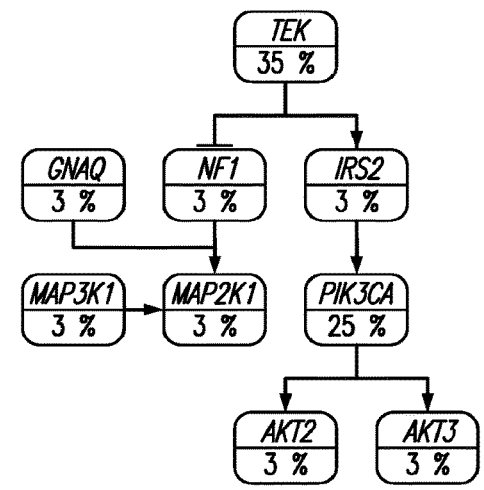

Human VM harbor PIK3CA mutations. Next, aiming to ascertain whether the same genetic alterations triggering the phenotype in our mouse and cell models were also present in the human condition, clinical specimens from adult patients (n=32) diagnosed with VM at our Institution were examined (FIG. 16). Due to the monographic nature of our cancer center, most of these vascular lesions had originally presented as deep-seated and infiltrative masses in the skeletal muscle and displayed a mixed pattern of vascular proliferation, including thick-wall malformed vessels, cavernous spaces filled with erythrocytes, and capillary areas (FIG. 7D-E, FIG. 16). These VM were analyzed by targeted-exome sequencing of 341 cancer-related genes using the MSK-IMPACT assay (26) developed at our institution, yielding a median coverage of 588X, as well as targeted sequencing for the TEK locus. Deep sequencing detected PIK3CA mutations in 25% of cases in previously described hot spots (H1047R, E542K) (FIG. 12A). In addition, gain-of-function mutations were found in other genes related to the PI3K pathway such as AKT2, AKT3, and IRS2, resulting in an overall of approximately 30% of mutations in the PI3K/AKT pathway (FIG. 7F; FIG. 16). Due to the impossibility to assess copy number variations (CNV) in the cohort as a result of the low allele frequency obtained (see Methods) and considering that amplifications in PIK3CA and loss in PTEN are two common alteration of the PI3K pathway in human cancer, fluorescence in situ hybridization (FISH) analysis in all the VM patient samples sequenced was performed. No amplification of PIK3CA or deletion of PTEN was detected in these samples (FIG. 12B). Furthermore, mutations in genes involved in the MAPK pathway (GNAQ, NF1, MAP2K1, MAP3K1) were found in 13% of the cases.

Figure 7G:
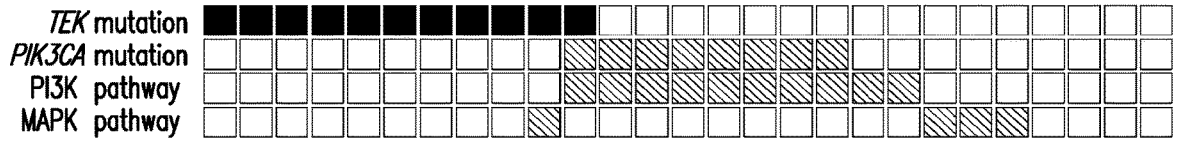

Previously described mutations in the tyrosine kinase receptor TEK (3, 7) were found in 35% of the patients of the cohort. These mutations were mutually exclusive with the mutations in the PI3K pathway, with the exception of one case (FIG. 7G). Taking in consideration that the TEK receptor is immediately upstream from PI3K and that signals via PI3K itself, VM may be defined as a disease state characterized by the presence of somatic activating mutations in the TIE2-PI3K-AKT axis.

Figure 8A:
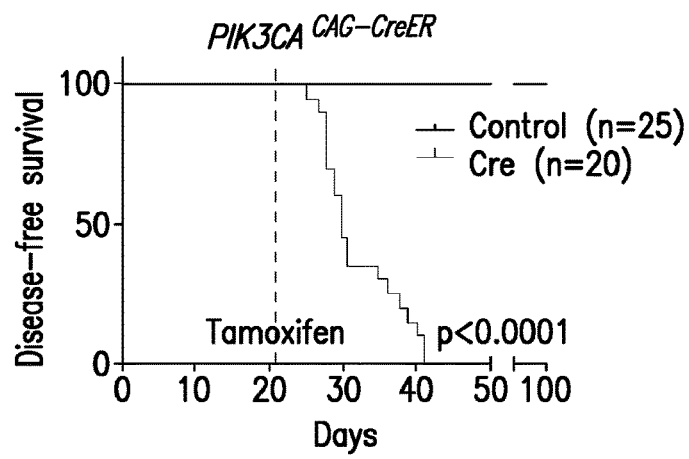
Figure 8B:
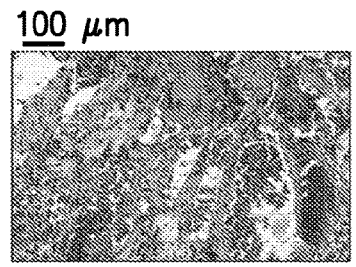
Figure 8C:
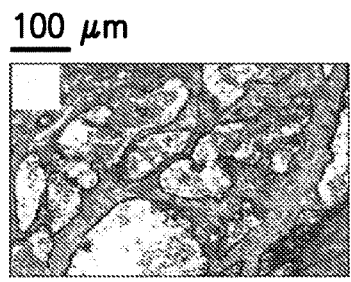
Figure 8D:
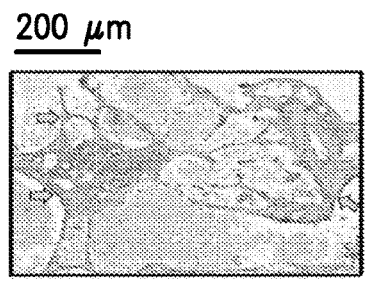
Figure 8E:
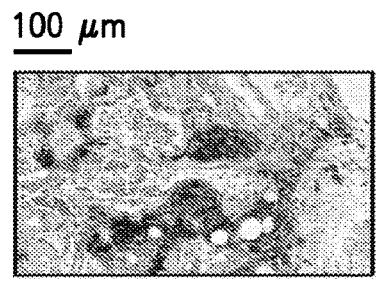
Figure 8F:
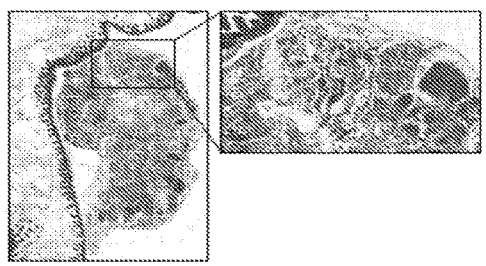
Figure 8I:
Figure 8G:
Figure 8H:
Figure 13A:
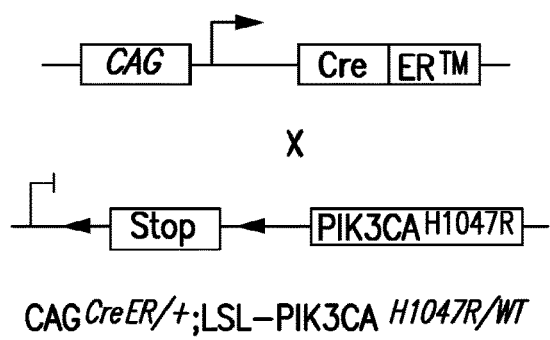
Figure 13B:
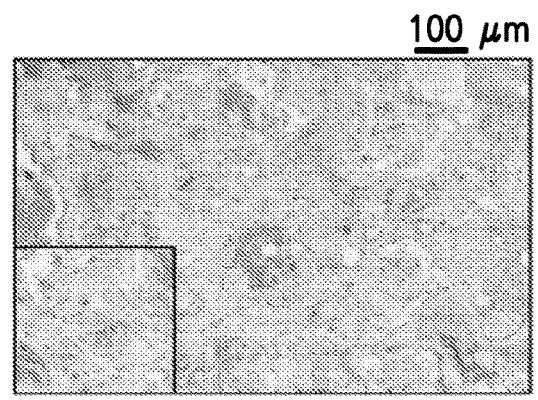
Figure 13C:
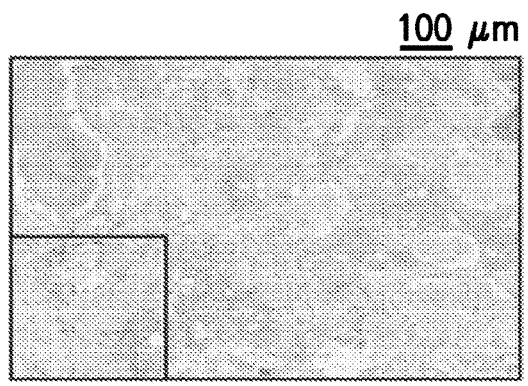
Figure 13D:
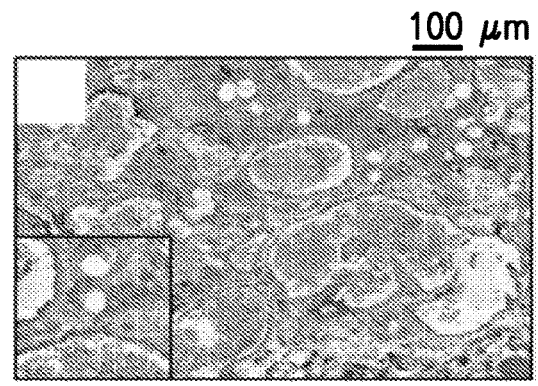
Figure 14A:
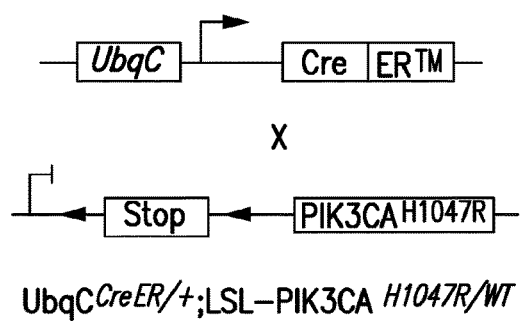
Figure 14B:
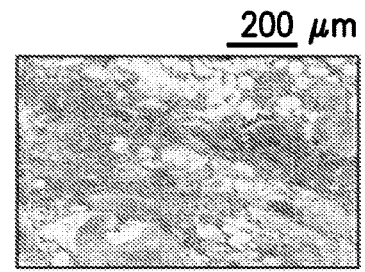
Figure 14C:
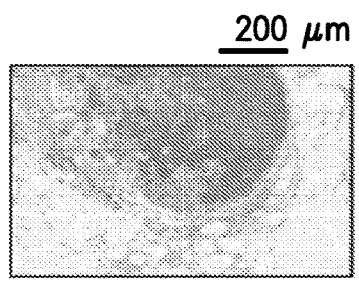
Figure 14D:
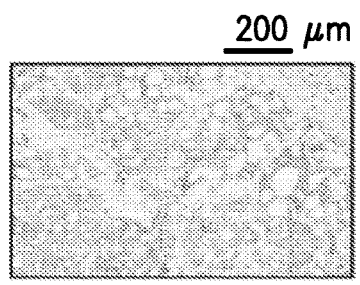
Figure 14E:
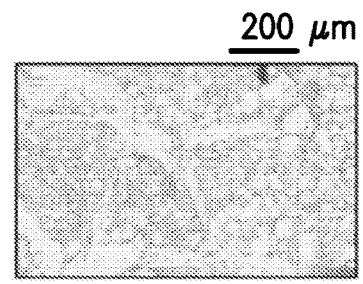

Ubiquitous expression of PIK3CA$^{H1047R}$ spontaneously induces VM in mice. It was hypothesized that the cell of origin giving rise to VM might be particularly sensitive to oncogenic PIK3CA transformation. Thus, PIK3CA$^{CAG-CreER}$ mice were generated in which the PIK3CA$^{H1047R}$ allele is ubiquitously expressed upon tamoxifen administration (27) (FIG. 13A). Six to eight week-old mice fed with tamoxifen rapidly developed cutaneous VM compared to the PIK3CA$^{WT}$ littermates (FIG. 8A). Histologic assessment confirmed a combined capillary and cavernous phenotype exhibiting dilated blood channels filled with erythrocytes (FIG. 8B) and immunoreactivity for CD31 (FIG. 8C) and phosphorylated AKT (S473), a surrogate marker of PI3K activation (FIG. 8D). Similar to the human pathology, murine VM were negative for GLUT-1, WT-1, and LYVE-1 (FIGS. 13B-D) and contained high levels of hemosiderin (FIG. 8E). Although the skin phenotype was readily evident, additional lesions were observed at necropsy at multiple sites including mesentery, genitourinary tract, kidney, and retina (FIG. 8F) with no apparent difference in incidence. Histological analyses of these lesions revealed large spaces filled with blood and lined by flattened EC, with similar immunophenotype, positive for CD31 and Prussian blue staining (FIG. 8G, H).

These findings were further confirmed using the UBC-CreER strain in which the Ubiquitin C promoter drives the expression of a tamoxifen-inducible Cre-recombinase in all the cells of the organism (28) (FIG. 14). Consistently, these results indicated that upon ubiquitous expression of the oncogenic PIK3CA transgene, the cell-of-origin for VM is more sensitive than other cell types to transformation, which results in the genesis of VM.

Figure 8J:
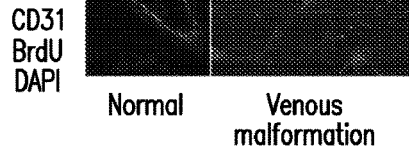

PI3K signaling has been shown to promote proliferation and cell growth (29, 30). However, it is not clear whether VM are a result of increased proliferation (31, 32). In order to test this in the mouse model, proliferation was studied by means of BrdU incorporation and Ki67 staining in both PIK3CA$^{WT}$ and PIK3CA$^{CAG-CreER}$ littermates. While normal blood vessels were negative for BrdU incorporation as a consequence of EC quiescence (33), VM displayed a marked increase in proliferative cells in both the EC and pericyte/smooth muscle compartment (FIG. 8I, 8J). It cannot rule out whether the proliferative enhancement observed in the non-endothelial cell compartment is caused by the direct effect of the PIK3CA mutant allele, or a result of paracrine signaling from proliferating EC, which has been shown to play an important role in the complex development of human VM (34)(35).

Figure 9A:
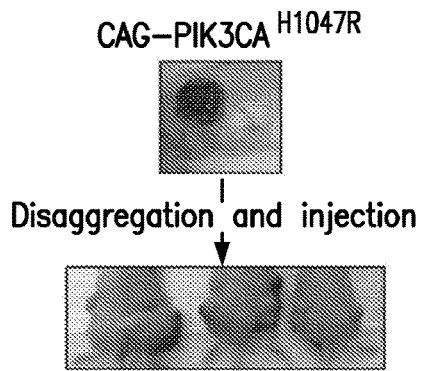
Figure 9B:
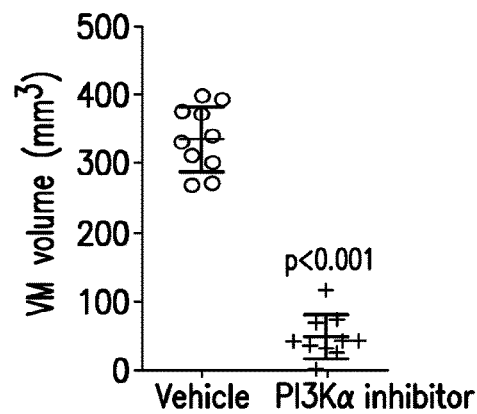
Figure 9C:
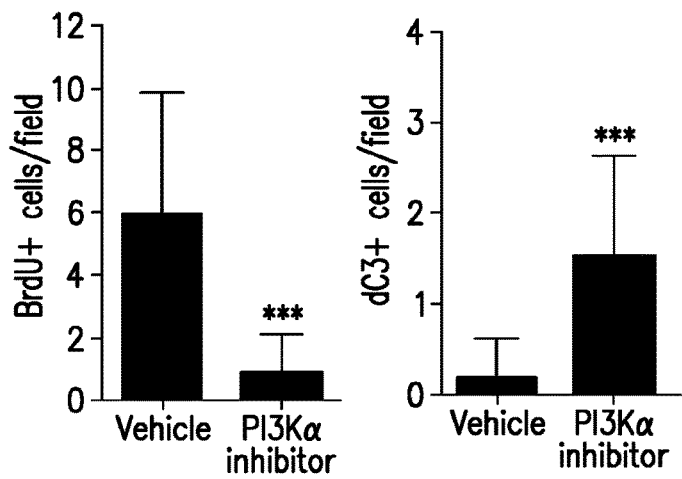
Figure 9D:
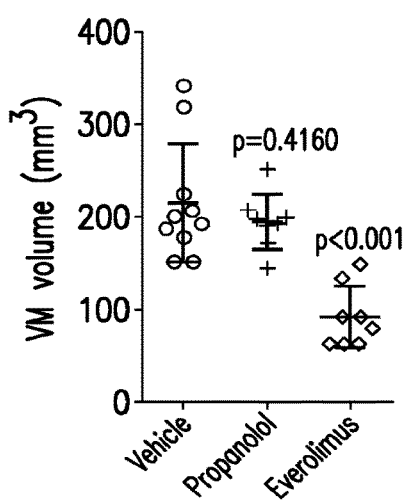
Figure 9E:
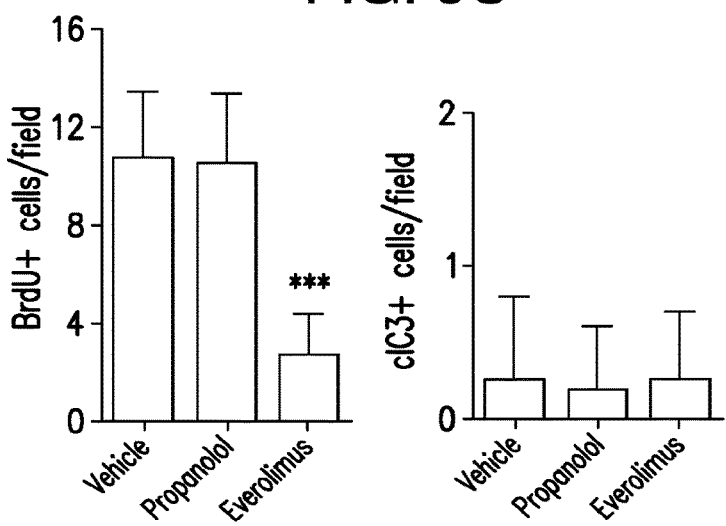

PI3K inhibitors are effective in the treatment of PIK3CA-induced VM. The presence of oncogenic PIK3CA mutations in VM, together with the observed phenotypes, prompted the evaluation of the full growth potential of these lesions, despite the fact of being considered as vascular malformations. To this end, PIK3CA$^{CAG-CreER}$ VM cells were injected into recipient immunocompromised nude mice. These cells resulted in the formation of highly vascularized and proliferative masses a few weeks after injection, with a histology and appearance highly resembling that of the original lesions (FIG. 9A). While VM do not have metastatic potential in patients, our finding that they may be successfully transplanted and grow in animals suggests that these lesions display tumorigenic behavior. Of clinical relevance, the presence of activating PIK3CA mutations in VM opens the door to treatment of this condition with PI3Kα inhibitors, currently under clinical development for several cancer indications (36). Treatment of VM with the PI3Kα selective inhibitor BYL719 resulted in a marked response as measured by a decrease in volume, reduced proliferation, and increased apoptosis (FIG. 9B-C). On the contrary, treatment with the β-adrenergic antagonist propranolol, an active agent against IH (23), did not yield any effect (FIG. 9D-E). In support of the role of the aberrant activation of the PI3K/mTOR pathway in VM, treatment with the mTOR inhibitor everolimus (37, 38) partially decreased VM size and proliferation, although it did not increase apoptosis (FIG. 9E).

Figure 9F:
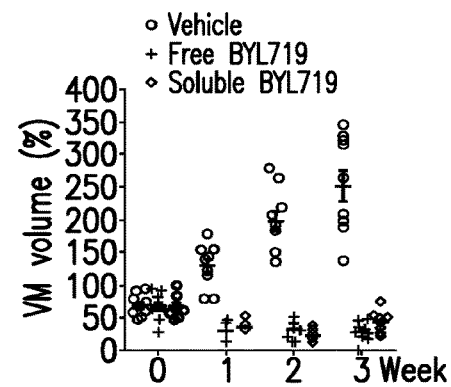

Given that a significant number of VM are detected in skin or superficial tissues, together with the substantial toxicity of systemic administration of PI3K inhibitors in patients, the topical application of PI3K inhibitors appeared to be of therapeutic interest in this context. To this end, two different cream preparations containing the PI3Kα-inhibitor BYL719 at 1% (w/w) that could be spread on the affected area were formulated (see Methods). Topical administration of the PI3Kα inhibitor achieved regression of skin lesions after one week, and these were prolonged in time using the two different cream formulas (FIG. 9F). Altogether, these results indicate that VM have tumorigenic potential, since they have the ability to grow in nude mice, and that treatment with PI3K inhibitors either systemically or locally is a suitable pharmacological approach to control the disease.

Figure 15A:
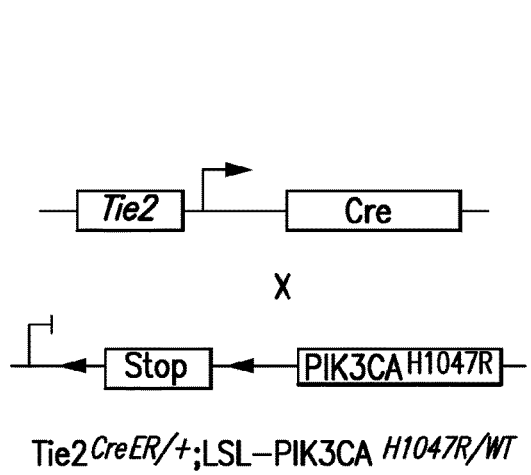
Figure 15B:
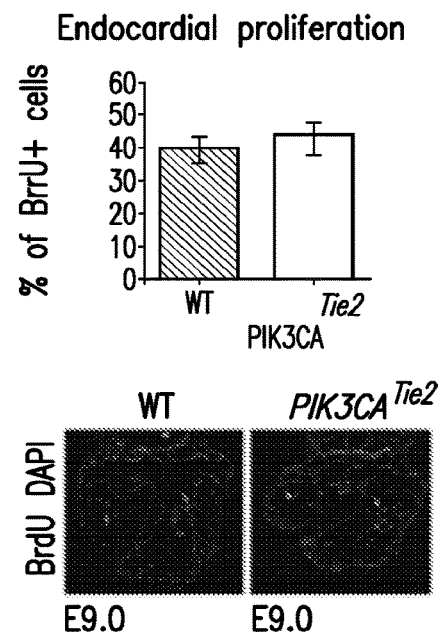
Figure 15C:
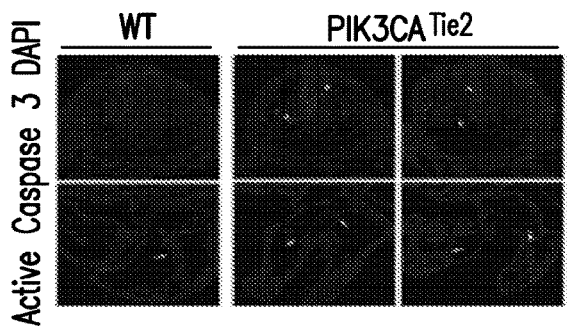
Figure 15D:
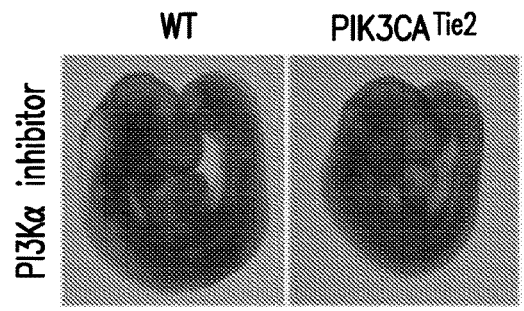
Figure 15E:
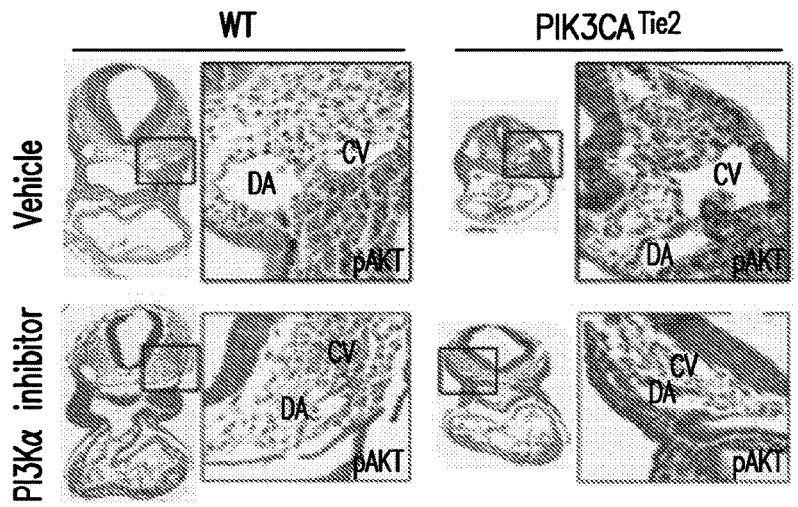

Expression of mutant PIK3CA impairs normal vasculogenesis. VM may occur as a result of defects during angiogenesis, a process in which PI3Kα is actively involved (12, 13, 39). To explore the biological significance of PI3K hyperactivation specifically in blood vessels, PIK3CA$^{H1047R}$ mice were crossed with the Tie2-Cre strain (40), which drives the expression of the transgene in EC (FIG. 15A). PIK3CA$^{Tie2-Cre}$ mice were not viable due to early embryonic lethality (E-10) as a result of vascular defects (FIG. 10A). CD31 staining of coronal sections revealed dilated blood vessels and vascular anomalies (FIG. 10B, upper panel) present in meningeal vessels, cardinal vein, and dorsal aorta. Moreover, small intersomitic vessels failed to form (FIG. 10B, lower panel), suggesting that deregulated PI3K activity results in lethal impairment of small vessel formation (12). These malformations were also evident in whole-mount embryo CD31 staining, with aberrant formation of the cephalic and intersomitic vessels (FIG. 10C-D, upper panels). Apoptosis and proliferation was not altered in PIK3CA$^{Tie2-Cre}$ embryos' hearts (FIG. 15B-C), suggesting that the observed phenotype is due to a defect specifically affecting blood vessels formation. Aiming to validate the implication of excessive PI3K signaling in aberrant vasculogenesis, as well as to evaluate whether pharmacological inhibition could overcome this effect, reversion of the phenotype was attempted by treating pregnant mice with the PI3Kα inhibitor BYL719. PIK3CA$^{Tie2-Cre}$ E9.5 embryos treated with the PI3Kα inhibitor showed an overall body-size comparable to PIK3CA$^{WT}$ littermates, suggesting improved vascular function (FIG. 15D). CD31 whole-mount staining revealed restored cephalic and intersomitic small blood vessel formation (FIG. 10C-D, lower panels). Phospho-AKT staining showed a strong reduction in both PIK3CA$^{Tie2-Cre}$ and PIK3CA$^{WT}$ embryos after PI3Kα inhibitor treatment, in contrast with untreated control embryos (FIG. 15E). At the histologic level, treatment reestablished meningeal, cardinal vein, and dorsal aorta blood vessels morphology (FIG. 10E), indicating that aberrant PI3K hyperactivation directly impairs normal embryonic angiogenesis in mice.

7.3 Discussion

Venous malformations are the most common vascular anomalies in humans (2). VM may cause pain, functional limitations of the affected area, aesthetic disfigurements and coagulopathy. In these cases sclerotherapy or surgical resection may be considered; however these procedures often involve complications such as cutaneous necrosis or extended inflammatory reactions (41) and depending on anatomic location and extension may be of limited application. Moreover VM are prone to recur (42), raising the need for developing more effective therapies.

Genetically engineered mouse models represent reliable tools for investigating the etiology, biology, and progression of human diseases, as well as for exploring novel therapeutic approaches (43, 44). The first somatic molecular alterations linked to the development of sporadic VM were the acquisition of gain-of-function mutations on the gene encoding for the EC-specific tyrosine-kinase receptor TIE2 (TEK) (3, 8, 45, 46). Ligand-independent receptor activation drives constitutive activation of the PI3K/AKT and MAPK pathways leading to increased proliferation and survival of EC that could account for increased EC accumulation in VM and abnormal recruitment of smooth muscle cells. However, only a subgroup of VM harbor defects in TEK, suggesting that other genomic or molecular alterations may be at play in this disease.

Recent studies performing xenograft experiments of HUVEC transduced with the most frequent TEK mutations have demonstrated their functional relevance in inducing VM (11). Treatment of murine xenografts with rapamycin proved the efficacy of inhibiting mTOR activity, and further showed clinical activity in VM patients. Intriguingly, three out of five patients that responded to mTOR inhibition in this study did not harbor any genetic defect in TEK (11). It is thus tempting to speculate that additional molecular alterations enhancing the activity of the PI3K/AKT/mTOR pathway could be driving the formation of VM in these patients.

In the present study, the generation of the first GEMM of VM by virtue of inducing the expression of the gain-of-function PIK3CA$^{H1047R}$ mutant allele in mice is reported. The histopathologic resemblance of the lesions arising in mice with those affecting humans prompted us to evaluate the existence of similar alterations in clinical specimens. Through targeted exome sequencing it was found that 25% of the evaluated samples bear activating mutations in PIK3CA, or additional genetic defects predicted to stimulate constitutive downstream signaling. In order to reconcile these findings with those previously reported, it was detected that 35% of the patients harbored mutations in TEK, yet these were mutually exclusive with the presence of activating PI3K mutations, consistent with a functional redundancy. These results are in agreement with the high prevalence of TEK mutations reported by others in pediatric patients (3, 7).

Somatic mutation of PIK3CA is frequently detected in several cancer types, and genetic alterations driving hyperactivation of the PI3K/AKT pathway have also been reported in nonhereditary post-zygotic tissue overgrowth syndromes that often exhibit mixed capillary, lymphatic, and venous anomalies. Due to clinical overlap in these overgrowth syndromes with PIK3CA mutations, the term PIK3CA-related overgrowth syndrome (PROS) has been proposed (15). Patients suffering CLOVES syndrome harbor somatic mosaicism for activating PIK3CA mutations resulting in hyperactive PI3K/AKT signaling (49). The presence of somatic mutations in PIK3CA were also detected in patients affected by Klippel-Trenaunay-Weber syndrome (KTS)—an overgrowth condition with features overlapping those of CLOVES syndrome—, isolated lymphatic malformations, fibro-adipose hyperplasia, and fibro-adipose vascular anomalies (50, 51). Additional genetic alterations in PTEN, GNAQ, AKT isoforms, or the regulatory subunit of PI3K, PIK3R1, that enhance PI3K/AKT/mTOR and MAPK pathway activation have also been reported in other malformative syndromes including Proteus (52), Megalencephaly capillary (53), Sturge-Weber (54), and Bannayan-Riley-Ruvalcaba (55) syndromes, underscoring the involvement of aberrant PI3K/AKT/mTOR signaling in developmental disorders. However, somatic mutations in PIK3CA have never been described in sporadic and solitary VM lesions, which is a different and much more prevalent entity not associated with overgrowth. Our observations are further supported by those made by Castillo and colleagues where mosaic somatic mutations induced in a PIK3CA$^{H1047R}$ mouse model cause VM that are neither associated with tissue overgrowth or lymphatic malformations (35), suggesting that the cell-of-origin giving rise to VM may be more susceptible to hyperactive PI3K signaling than other cell lineages, and that additional genetic or environmental cues are required to reproduce the complex phenotypes observed in overgrowth syndromes.

Given the validity of this mouse model to recapitulate the pathogenesis of human VM, we asked whether it could be used as a platform for testing pharmacological inhibition using PI3K inhibitors currently under clinical development. To put it into context, the efficacy of other agents that have been proposed to inhibit the growth of VM, including rapamycin analogues and propranolol were also evaluated (11, 56). Greatest growth inhibition was achieved when treating allograft transplants with PI3Kα-inhibitor and the rapamycin analogue everolimus, as compared with no effect observed with propranolol. In contrast to the antiproliferative effect of rapamycin analogues, it is proposed that the pro-apoptotic effect achieved upon PI3K inhibition is likely to yield improved therapeutic efficacy by diminishing the recurrence of VM. Topical administration of PI3Kα inhibitor further demonstrated the efficacy of this treatment, an approach that would be devoid of the substantial side effects associated with systemic drug administration (hyperglycemia, nausea, gastrointestinal effects, and fatigue). Importantly, the impaired vasculogenesis observed in embryos as a result of endothelial-restricted expression of the PIK3CA$^{H1047R}$ allele was also rescued when pregnant mice were treated with the PI3Kα-inhibitor, further supporting a functional requirement for controlled PI3K signaling in normal embryonic vasculogenesis as has been demonstrated by others (39).

In summary, this study provides the first GEMM recapitulating human VM caused by hyperactivation of the PI3K/AKT pathway, reveals the impact of PIK3CA somatic mutations in the pathogenesis of VM, and provide an effective therapeutic approach to treat advanced or recurrent lesions in these patients.

REFERENCES

1. H. L. Nguyen, L. M. Boon, M. Vikkula, Genetics of vascular malformations. Seminars in pediatric surgery 23, 221-226 (2014).
2. M. Uebelhoer, L. M. Boon, M. Vikkula, Vascular anomalies: from genetics toward models for therapeutic trials. Cold Spring Harbor perspectives in medicine 2, (2012).
3. N. Limaye, V. Wouters, M. Uebelhoer, M. Tuominen, R. Wirkkala, J. B. Mulliken, L. Eklund, L. M. Boon, M. Vikkula, Somatic mutations in angiopoietin receptor gene TEK cause solitary and multiple sporadic venous malformations. Nature genetics 41, 118-124 (2009).
4. P. Brouillard, M. Vikkula, Genetic causes of vascular malformations. Human molecular genetics 16 Spec No. 2, R140-149 (2007).
5. P. Brouillard, M. Vikkula, Vascular malformations: localized defects in vascular morphogenesis. Clinical genetics 63, 340-351 (2003).
6. A. Dompmartin, M. Vikkula, L. M. Boon, Venous malformation: update on aetiopathogenesis, diagnosis and management. Phlebology/Venous Forum of the Royal Society of Medicine 25, 224-235 (2010).
7. J. Soblet, N. Limaye, M. Uebelhoer, L. M. Boon, M. Vikkula, Variable Somatic TIE2 Mutations in Half of Sporadic Venous Malformations. Molecular syndromology 4, 179-183 (2013).
8. M. Vikkula, L. M. Boon, K. L. Carraway, 3rd, J. T. Calvert, A. J. Diamonti, B. Goumnerov, K. A. Pasyk, D. A. Marchuk, M. L. Warman, L. C. Cantley, J. B. Mulliken, B. R. Olsen, Vascular dysmorphogenesis caused by an activating mutation in the receptor tyrosine kinase TIE2. Cell 87, 1181-1190 (1996).
9. C. D. Kontos, T. P. Stauffer, W. P. Yang, J. D. York, L. Huang, M. A. Blanar, T. Meyer, K. G. Peters, Tyrosine 1101 of Tie2 is the major site of association of p85 and is required for activation of phosphatidylinositol 3-kinase and Akt. Molecular and cellular biology 18, 4131-4140 (1998).
10. P. N. Morris, B. J. Dunmore, A. Tadros, D. A. Marchuk, D. C. Darland, P. A. D'Amore, N. P. Brindle, Functional analysis of a mutant form of the receptor tyrosine kinase Tie2 causing venous malformations. Journal of molecular medicine 83, 58-63 (2005).

11. E. Boscolo, N. Limaye, L. Huang, K. T. Kang, J. Soblet, M. Uebelhoer, A. Mendola, M. Natynki, E. Seront, S. Dupont, J. Hammer, C. Legrand, C. Brugnara, L. Eklund, M. Vikkula, J. Bischoff, L. M. Boon, Rapamycin improves TIE2-mutated venous malformation in murine model and human subjects. *The Journal of clinical investigation* 125, 3491-3504 (2015).
12. M. Graupera, J. Guillermet-Guibert, L. C. Foukas, L. K. Phng, R. J. Cain, A. Salpekar, W. Pearce, S. Meek, J. Millan, P. R. Cutillas, A. J. Smith, A. J. Ridley, C. Ruhrberg, H. Gerhardt, B. Vanhaesebroeck, Angiogenesis selectively requires the p110alpha isoform of PI3K to control endothelial cell migration. *Nature* 453, 662-666 (2008).
13. M. Graupera, M. Potente, Regulation of angiogenesis by PI3K signaling networks. *Experimental cell research* 319, 1348-1355 (2013).
14. H. T. Yuan, E. V. Khankin, S. A. Karumanchi, S. M. Parikh, Angiopoietin 2 is a partial agonist/antagonist of Tie2 signaling in the endothelium. *Molecular and cellular biology* 29, 2011-2022 (2009).
15. H. C. Kang, S. T. Baek, S. Song, J. G. Gleeson, Clinical and Genetic Aspects of the Segmental Overgrowth Spectrum Due to Somatic Mutations in PIK3CA. *The Journal of pediatrics,* (2015).
16. A. J. Osborn, P. Dickie, D. E. Neilson, K. Glaser, K. A. Lynch, A. Gupta, B. H. Dickie, Activating PIK3CA alleles and lymphangiogenic phenotype of lymphatic endothelial cells isolated from lymphatic malformations. *Human molecular genetics* 24, 926-938 (2015).
17. N. Cancer Genome Atlas Research, C. Kandoth, N. Schultz, A. D. Cherniack, R. Akbani, Y. Liu, H. Shen, A. G. Robertson, I. Pashtan, R. Shen, C. C. Benz, C. Yau, P. W. Laird, L. Ding, W. Zhang, G. B. Mills, R. Kucherlapati, E. R. Mardis, D. A. Levine, Integrated genomic characterization of endometrial carcinoma. *Nature* 497, 67-73 (2013).
18. J. R. Adams, K. Xu, J. C. Liu, N. M. Agamez, A. J. Loch, R. G. Wong, W. Wang, K. L. Wright, T. F. Lane, E. Zacksenhaus, S. E. Egan, Cooperation between Pik3ca and p53 mutations in mouse mammary tumor formation. *Cancer research* 71, 2706-2717 (2011).
19. C. M. Contreras, E. A. Akbay, T. D. Gallardo, J. M. Haynie, S. Sharma, O. Tagao, N. Bardeesy, M. Takahashi, J. Settleman, K. K. Wong, D. H. Castrillon, Lkb1 inactivation is sufficient to drive endometrial cancers that are aggressive yet highly responsive to mTOR inhibitor monotherapy. *Disease models & mechanisms* 3, 181-193 (2010).
20. M. Wassef, F. Blei, D. Adams, A. Alomari, E. Baselga, A. Berenstein, P. Burrows, I. J. Frieden, M. C. Garzon, J. C. Lopez-Gutierrez, D. J. Lord, S. Mitchel, J. Powell, J. Prendiville, M. Vikkula, I. Board, C. Scientific, Vascular Anomalies Classification: Recommendations From the International Society for the Study of Vascular Anomalies. *Pediatrics,* (2015).
21. P. E. North, M. Waner, A. Mizeracki, M. C. Mihm, Jr., GLUT1: a newly discovered immunohistochemical marker for juvenile hemangiomas. *Human pathology* 31, 11-22 (2000).
22. L. P. Lawley, F. Cerimele, S. W. Weiss, P. North, C. Cohen, H. P. Kozakewich, J. B. Mulliken, J. L. Arbiser, Expression of Wilms tumor 1 gene distinguishes vascular malformations from proliferative endothelial lesions. *Archives of dermatology* 141, 1297-1300 (2005).
23. C. Leaute-Labreze, P. Hoeger, J. Mazereeuw-Hautier, L. Guibaud, E. Baselga, G. Posiunas, R. J. Phillips, H. Caceres, J. C. Lopez Gutierrez, R. Ballona, S. F. Friedlander, J. Powell, D. Perek, B. Metz, S. Barbarot, A. Maruani, Z. Z. Szalai, A. Krol, O. Boccara, R. Foelster-Holst, M. I. Febrer Bosch, J. Su, H. Buckova, A. Torrelo, F. Cambazard, R. Grantzow, O. Wargon, D. Wyrzykowski, J. Roessler, J. Bernabeu-Wittel, A. M. Valencia, P. Przewratil, S. Glick, E. Pope, N. Birchall, L. Benjamin, A. J. Mancini, P. Vabres, P. Souteyrand, I. J. Frieden, C. I. Berul, C. R. Mehta, S. Prey, F. Boralevi, C. C. Morgan, S. Heritier, A. Delarue, J. J. Voisard, A randomized, controlled trial of oral propranolol in infantile hemangioma. *The New England journal of medicine* 372, 735-746 (2015).
24. P. Brouillard, L. Boon, M. Vikkula, Genetics of lymphatic anomalies. *The Journal of clinical investigation* 124, 898-904 (2014).
25. S. Banerji, J. Ni, S. X. Wang, S. Clasper, J. Su, R. Tammi, M. Jones, D. G. Jackson, LYVE-1, a new homologue of the CD44 glycoprotein, is a lymph-specific receptor for hyaluronan. *The Journal of cell biology* 144, 789-801 (1999).
26. D. T. Cheng, T. N. Mitchell, A. Zehir, R. H. Shah, R. Benayed, A. Syed, R. Chandramohan, Z. Y. Liu, H. H. Won, S. N. Scott, A. R. Brannon, C. O'Reilly, J. Sadowska, J. Casanova, A. Yannes, J. F. Hechtman, J. Yao, W. Song, D. S. Ross, A. Oultache, S. Dogan, L. Borsu, M. Hameed, K. Nafa, M. E. Arcila, M. Ladanyi, M. F. Berger, Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology. *The Journal of molecular diagnostics: JMD* 17, 251-264 (2015).
27. S. Hayashi, A. P. McMahon, Efficient recombination in diverse tissues by a tamoxifen-inducible form of Cre: a tool for temporally regulated gene activation/inactivation in the mouse. *Developmental biology* 244, 305-318 (2002).
28. Y. Ruzankina, C. Pinzon-Guzman, A. Asare, T. Ong, L. Pontano, G. Cotsarelis, V. P. Zediak, M. Velez, A. Bhandoola, E. J. Brown, Deletion of the developmentally essential gene ATR in adult mice leads to age-related phenotypes and stem cell loss. *Cell stem cell* 1, 113-126 (2007).
29. J. A. Engelman, Targeting PI3K signalling in cancer: opportunities, challenges and limitations. *Nature reviews. Cancer* 9, 550-562 (2009).
30. D. A. Fruman, C. Rommel, PI3K and cancer: lessons, challenges and opportunities. *Nature reviews. Drug discovery* 13, 140-156 (2014).
31. R. H. Adams, K. Alitalo, Molecular regulation of angiogenesis and lymphangiogenesis. *Nature reviews. Molecular cell biology* 8, 464-478 (2007).
32. M. C. Smith, D. Y. Li, K. J. Whitehead, Mechanisms of vascular stability and the relationship to human disease. *Current opinion in hematology* 17, 237-244 (2010).
33. S. P. Herbert, D. Y. Stainier, Molecular control of endothelial cell behaviour during blood vessel morphogenesis. *Nature reviews. Molecular cell biology* 12, 551-564 (2011).
34. M. Uebelhoer, M. Natynki, J. Kangas, A. Mendola, H. L. Nguyen, J. Soblet, C. Godfraind, L. M. Boon, L. Eklund, N. Limaye, M. Vikkula, Venous malformation-causative TIE2 mutations mediate an AKT-dependent decrease in PDGFB. *Human molecular genetics* 22, 3438-3448 (2013).

35. Castillo S D, Tzouanacou E, Zaw-Thin M, Berenjeno I M, Parker V, Chivite I, Mild-Guasch M, Pearce W, Solomon I, Dewhurst R E, Knox R G, Scudamore C L, Badar A, Kalber T L, Foster J, Stuckey D J, David A, Phillips W A, Lythgoe M F, Wilson V, Semple R K, Sebire N J, Kinsler V A, Graupera M, Vanhaesebroeck, B. 2015 Somatic mutation in Pik3ca causes sporadic venous malformations (Unpublished)

36. C. Fritsch, A. Huang, C. Chatenay-Rivauday, C. Schnell, A. Reddy, M. Liu, A. Kauffmann, D. Guthy, D. Erdmann, A. De Pover, P. Furet, H. Gao, S. Ferretti, Y. Wang, J. Trappe, S. M. Brachmann, S. M. Maira, C. Wilson, M. Boehm, C. Garcia-Echeverria, P. Chene, M. Wiesmann, R. Cozens, J. Lehar, R. Schlegel, G. Caravatti, F. Hofmann, W. R. Sellers, Characterization of the novel and specific PI3Kalpha inhibitor NVP-BYL719 and development of the patient stratification strategy for clinical trials. *Molecular cancer therapeutics* 13, 1117-1129 (2014).

37. H. Lackner, A. Karastaneva, W. Schwinger, M. Benesch, P. Sovinz, M. Seidel, D. Sperl, S. Lanz, E. Haxhija, F. Reiterer, E. Sorantin, C. E. Urban, Sirolimus for the treatment of children with various complicated vascular anomalies. *European journal of pediatrics*, (2015).

38. A. M. Hammill, M. Wentzel, A. Gupta, S. Nelson, A. Lucky, R. Elluru, R. Dasgupta, R. G. Azizkhan, D. M. Adams, Sirolimus for the treatment of complicated vascular anomalies in children. *Pediatric blood & cancer* 57, 1018-1024 (2011).

39. L. M. Hare, Q. Schwarz, S. Wiszniak, R. Gurung, K. G. Montgomery, C. A. Mitchell, W. A. Phillips, Heterozygous expression of the oncogenic Pik3ca(H1047R) mutation during murine development results in fatal embryonic and extraembryonic defects. *Developmental biology* 404, 14-26 (2015).

40. Y. Y. Kisanuki, R. E. Hammer, J. Miyazaki, S. C. Williams, J. A. Richardson, M. Yanagisawa, Tie2-Cre transgenic mice: a new model for endothelial cell-lineage analysis in vivo. *Developmental biology* 230, 230-242 (2001).

41. J. A. Cox, E. Bartlett, E. I. Lee, Vascular Malformations: A Review. *Semin Plast Surg* 28, 58-63 (2014).

42. A. A. Delorimier, Sclerotherapy for Venous Malformations. *J Pediatr Surg* 30, 188-194 (1995).

43. J. Heyer, L. N. Kwong, S. W. Lowe, L. Chin, Non-germline genetically engineered mouse models for translational cancer research. *Nat Rev Cancer* 10, 470-480 (2010).

44. M. H. van Miltenburg, J. Jonkers, Using genetically engineered mouse models to validate candidate cancer genes and test new therapeutic approaches. *Curr Opin Genet Dev* 22, 21-27 (2012).

45. J. T. Calvert, T. J. Riney, C. D. Kontos, E. H. Cha, V. G. Prieto, C. R. Shea, J. N. Berg, N. C. Nevin, S. A. Simpson, K. A. Pasyk, M. C. Speer, K. G. Peters, D. A. Marchuk, Allelic and locus heterogeneity in inherited venous malformations. *Human molecular genetics* 8, 1279-1289 (1999).

46. V. Wouters, N. Limaye, M. Uebelhoer, A. Irrthum, L. M. Boon, J. B. Mulliken, O. Enjolras, E. Baselga, J. Berg, A. Dompmartin, S. A. Ivarsson, L. Kangesu, Y. Lacassie, J. Murphy, A. S. Teebi, A. Penington, P. Rieu, M. Vikkula, Hereditary cutaneomucosal venous malformations are caused by TIE2 mutations with widely variable hyperphosphorylating effects. *Eur J Hum Genet* 18, 414-420 (2010).

47. N. Jones, Z. Master, J. Jones, D. Bouchard, Y. Gunji, H. Sasaki, R. Daly, K. Alitalo, D. J. Dumont, Identification of Tek/Tie2 binding partners. Binding to a multifunctional docking site mediates cell survival and migration. *The Journal of biological chemistry* 274, 30896-30905 (1999).

48. I. Kim, H. G. Kim, J. N. So, J. H. Kim, H. J. Kwak, G. Y. Koh, Angiopoietin-1 regulates endothelial cell survival through the phosphatidylinositol 3'-Kinase/Akt signal transduction pathway. *Circulation research* 86, 24-29 (2000).

49. K. C. Kurek, V. L. Luks, U. M. Ayturk, A. I. Alomari, S. J. Fishman, S. A. Spencer, J. B. Mulliken, M. E. Bowen, G. L. Yamamoto, H. P. Kozakewich, M. L. Warman, Somatic mosaic activating mutations in PIK3CA cause CLOVES syndrome. *American journal of human genetics* 90, 1108-1115 (2012).

50. V. L. Luks, N. Kamitaki, M. P. Vivero, W. Uller, R. Rab, J. V. M. G. Bovee, K. L. Rialon, C. J. Guevara, A. I. Alomari, A. K. Greene, S. J. Fishman, H. P. W. Kozakewich, R. A. Maclellan, J. B. Mulliken, R. Rahbar, S. A. Spencer, C. C. Trenor, J. Upton, D. Zurakowski, J. A. Perkins, A. Kirsh, J. T. Bennett, W. B. Dobyns, K. C. Kurek, M. L. Warman, S. A. McCarroll, R. Murillo, Lymphatic and Other Vascular Malformative/Overgrowth Disorders Are Caused by Somatic Mutations in PIK3CA. *J Pediatr-Us* 166, 1048-U1376 (2015).

51. M. J. Lindhurst, V. E. Parker, F. Payne, J. C. Sapp, S. Rudge, J. Harris, A. M. Witkowski, Q. Zhang, M. P. Groeneveld, C. E. Scott, A. Daly, S. M. Huson, L. L. Tosi, M. L. Cunningham, T. N. Darling, J. Geer, Z. Gucev, V. R. Sutton, C. Tziotzios, A. K. Dixon, T. Helliwell, S. O'Rahilly, D. B. Savage, M. J. Wakelam, I. Barroso, L. G. Biesecker, R. K. Semple, Mosaic overgrowth with fibroadipose hyperplasia is caused by somatic activating mutations in PIK3CA. *Nature genetics* 44, 928-933 (2012).

52. M. J. Lindhurst, J. C. Sapp, J. K. Teer, J. J. Johnston, E. M. Finn, K. Peters, J. Turner, J. L. Cannons, D. Bick, L. Blakemore, C. Blumhorst, K. Brockmann, P. Calder, N. Cherman, M. A. Deardorff, D. B. Everman, G. Golas, R. M. Greenstein, B. M. Kato, K. M. Keppler-Noreuil, S. A. Kuznetsov, R. T. Miyamoto, K. Newman, D. Ng, K. O'Brien, S. Rothenberg, D. J. Schwartzentruber, V. Singhal, R. Tirabosco, J. Upton, S. Wientroub, E. H. Zackai, K. Hoag, T. Whitewood-Neal, P. G. Robey, P. L. Schwartzberg, T. N. Darling, L. L. Tosi, J. C. Mullikin, L. G. Biesecker, A mosaic activating mutation in AKT1 associated with the *Proteus* syndrome. *The New England journal of medicine* 365, 611-619 (2011).

53. J. B. Riviere, G. M. Mirzaa, B. J. O'Roak, M. Beddaoui, D. Alcantara, R. L. Conway, J. St-Onge, J. A. Schwartzentruber, K. W. Gripp, S. M. Nikkel, T. Worthylake, C. T. Sullivan, T. R. Ward, H. E. Butler, N. A. Kramer, B. Albrecht, C. M. Armour, L. Armstrong, O. Caluseriu, C. Cytrynbaum, B. A. Drolet, A. M. Innes, J. L. Lauzon, A. E. Lin, G. M. Mancini, W. S. Meschino, J. D. Reggin, A. K. Saggar, T. Lerman-Sagie, G. Uyanik, R. Weksberg, B. Zirn, C. L. Beaulieu, C. Finding of Rare Disease Genes Canada, J. Majewski, D. E. Bulman, M. O'Driscoll, J. Shendure, J. M. Graham, Jr., K. M. Boycott, W. B. Dobyns, De novo germline and postzygotic mutations in AKT3, PIK3R2 and PIK3CA cause a spectrum of related megalencephaly syndromes. *Nature genetics* 44, 934-940 (2012).

54. M. D. Shirley, H. Tang, C. J. Gallione, J. D. Baugher, L. P. Frelin, B. Cohen, P. E. North, D. A. Marchuk, A. M. Comi, J. Pevsner, Sturge-Weber syndrome and port-wine stains caused by somatic mutation in GNAQ. *The New England journal of medicine* 368, 1971-1979 (2013).

55. D. J. Marsh, P. L. Dahia, Z. Zheng, D. Liaw, R. Parsons, R. J. Gorlin, C. Eng, Germline mutations in PTEN are present in Bannayan-Zonana syndrome. *Nature genetics* 16, 333-334 (1997).
56. C. Pfohler, E. Janssen, A. Buecker, T. Vogt, C. S. L. Muller, Successful treatment of a congenital extra-truncal vascular malformation by orally administered propranolol. *J Dermatol Treat* 26, 59-62 (2015).

8. EXAMPLE 3: SOMATIC PIK3CA MUTATIONS AS A DRIVER OF SPORADIC VENOUS MALFORMATIONS

8.1 Summary

The present example shows that activating PIK3CA mutations give rise to sporadic VM in mice, which closely resemble the histology of the human disease. Furthermore, mutations in PIK3CA and related genes of the PI3K/AKT pathway were identified in approximately 30% of human VM that lack TEK alterations. PIK3CA mutations promote downstream signaling and proliferation in endothelial cells and impair normal vasculogenesis in embryonic development. VM in mouse models was successfully treated using pharmacological inhibitors of PI3Kα administered either systemically or topically.

8.2 Results

PIK3CA$^{Sprr2f\text{-}Cre}$ Mice Develop Spinal and Cutaneous VM

Figure 18A:
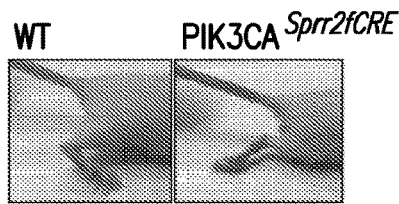
Figure 18C:
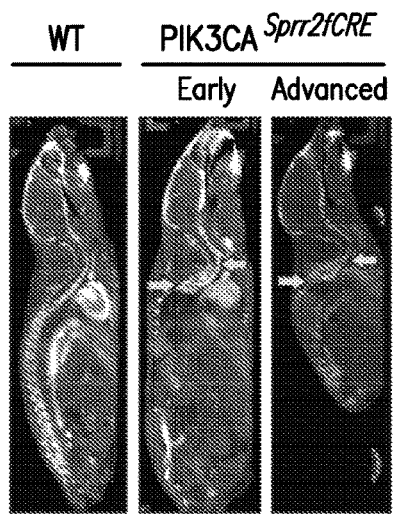
Figure 18B:
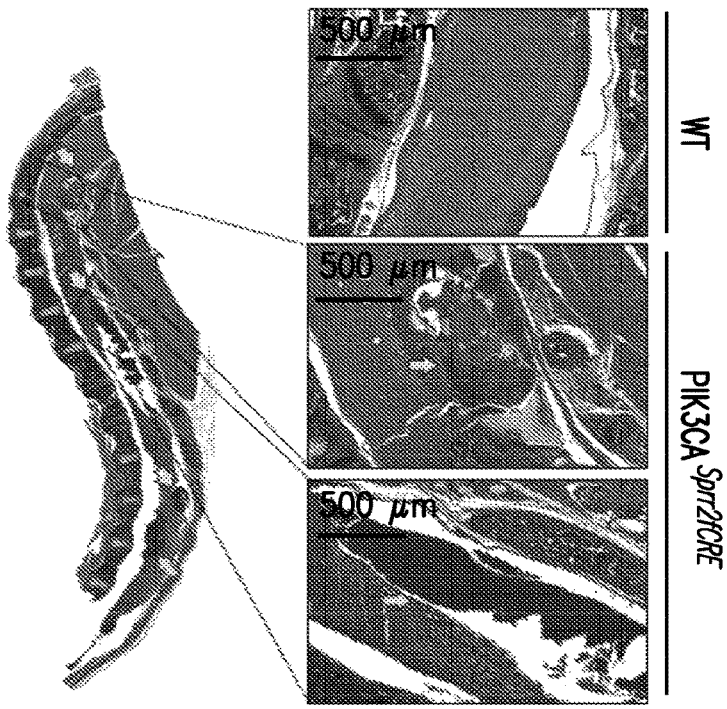

To investigate the role of PIK3CA, the gene encoding the catalytic p110α subunit of PI3K (PI3Kα), oncogenicity in uterine cancer, the mouse strain LoxP-STOP-LoxP (LSL)-PIK3CA$^{H1047R}$ was used, which allows the expression of the activating PIK3CA mutation H1047R in a tissue-specific manner using the Cre-loxP technology upon removal of the foxed synthetic transcriptional/translational STOP cassette (22). These animals were crossed with the Sprr2f-Cre strain, shown to drive Cre recombinase expression in both luminal and glandular uterine epithelial cells (23) (FIG. 17A). Unexpectedly, although PIK3CA$^{Sprr2f\text{-}WT}$ mice were viable and normal, PIK3CA$^{Sprr2f\text{-}Cre}$ littermates exhibited hind limb paralysis at an early age (4-10 weeks) (FIG. 18A). Because this phenotype was observed in both males and females, the pathologic events underlying this phenotype were further explored. Histologic examination revealed lesions in the spinal cord resembling human vascular malformations that were not present in WT animals (FIG. 18B). Specifically, these abnormalities showed dilated 'cavernous' vascular spaces with extensive blood pools and hemorrhage involving both white and gray matter.

Figure 18D:
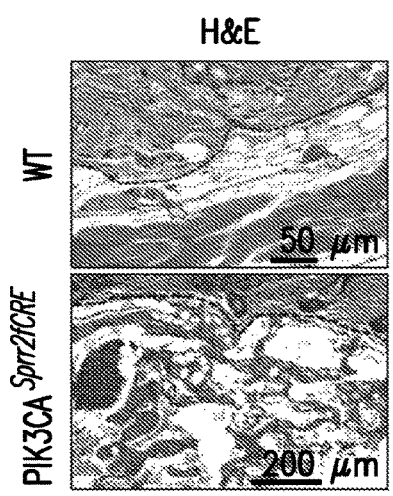
Figure 18E:
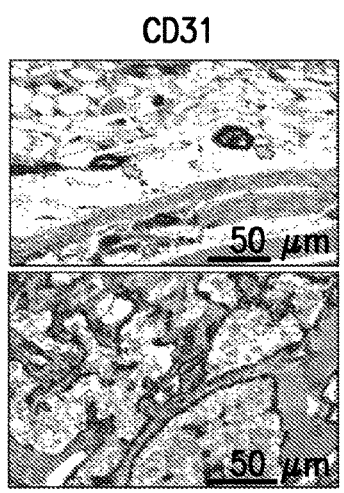
Figure 18F:
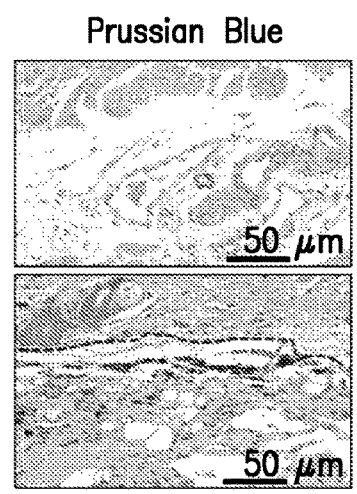

The spinal lesions in PIK3CA$^{Sprr2f\text{-}Cre}$ mice were further examined by intravenously injecting gold nanoparticles, using in vivo X-ray computed tomography imaging to confirm the presence of hyperdense lesions in the spine. These vascular lesions were present in animals with both advanced and milder phenotypes but not in WT littermates (FIG. 18C) and showed slow blood flow and extravasation, radiological features of vascular malformations of the spine (24). The abnormal vascular channels, represented by cavernous spaces and capillary proliferation, were consistent with a diagnosis of VM according to the current classification of the International Society for the Study of Vascular Anomalies (25). Among the observed alterations, cutaneous VM were the most frequent, exhibiting high penetrance in the PIK3CA$^{Sprr2f\text{-}Cre}$ mice (approximately 90%) (FIG. 18D). Microscopically, the skin lesions resembled human VM with positivity for CD31 (FIG. 18E; 17B) and Perl's Prussian blue staining (FIG. 18F) indicative of endothelial cell lining and hemosiderin deposition, respectively.

To further characterize the observed lesions, the mouse VM were examined for expression of both GLUT-1 and WT-1, which are immunophenotyping markers of infantile hemangioma (IH), a different vascular disease with a distinct natural history that responds to the β-blocker propranolol (26-28). Both types of staining were negative in mouse VM samples as compared to positive controls from human IH specimens and mouse tissue (FIG. 17C-D). Lymphatic malformations, which can histologically resemble VM, can also harbor PIK3R1 and PIK3CA mutations (29). In fact, mice with a knockout of Pik3r1, encoding the PI3K regulatory subunits p85α, p55α, and p50α, have defects in normal lymphangiogenesis and develop lymphatic malformations in the intestines and skin (30). Thus, to assess whether the VM model might exhibit a substantial lymphatic component, expression of the lymphatic-specific markers lymphatic vessel endothelial hyaluronan receptor 1 (LYVE-1) (31) and Prospero homeobox 1 (PROX-1) (32) was examined. IHC staining with these lymphatic markers did not detect any relevant reactivity in the areas comprising the malformation, indicating that these lesions are entirely VM (FIG. 17E-F).

To examine whether the Sprr2f-Cre strain drives the expression of the Cre recombinase in mature or precursor ECs, in addition to the reported endometrial epithelial cells, the LSL-LacZ reporter strain was crossed with the Sprr2f-Cre mouse and β-galactosidase expression was determined in spinal sections. In LacZ$^{Sprr2f\text{-}Cre}$ sections, discrete positive cells were detected resembling ECs that were sparsely distributed within the white and gray matter of the spinal cord (FIG. 17G). Double immunofluorescence staining against Cre and CD31 on VM from the Sprr2f-Cre mice confirmed the presence of Cre recombinase in the CD31-positive lesions that explain the vascular phenotype observed in these mice (FIG. 17H).

PIK3CA Activating Mutation Affects Normal Endothelial Cells

Primary human skin ECs were transduced with retrovirus encoding the PIK3CA WT or H1047R variants to study the cellular mechanisms by which PIK3CA mutations might alter EC function. PIK3CA$^{H1047R}$ mutant cells exhibited amplified downstream PI3K/AKT/mTOR signaling with increased phosphorylation of AKT at S473 and T308, and the mTOR downstream targets S6-kinase at T389 and ribosomal S6 protein at S235/6 and S240/4 (FIG. 19A). Tube formation assays were conducted to assess the ability of these cells to form a normal capillary network in a 3D matrix, an approach widely used to assess the normal function of EC (33). PIK3CA$^{H1047R}$ mutant cells formed aberrant EC clusters, as opposed to their WT counterparts, which generated normal vascular tubes in vitro (FIG. 19B). These results were further confirmed using human umbilical vein endothelial cells (HUVECs) infected with PIK3CA WT and the H1047R mutant, which recapitulated the increased PI3K/AKT signaling (FIG. 20A) and aberrant tube formation in vitro (FIG. 20B).

Because PI3K regulates cell proliferation (18), the proliferation ratio of the primary cells was tested in vitro using EdU incorporation assays which showed that the mutant cells exhibited a slightly higher, but reproducible, proliferation rate as compared with WT cells and empty vector controls, which was reversed upon treatment with a PI3Kα inhibitor (FIG. 19C) in a dose-dependent manner (FIG. 20C, D).

ECs, which are key players in the development of vascular malformations, create a pathological niche that involves the mural cell compartment, probably in part as a result of aberrant cytokine secretion (12, 34). To test the impact of the PIK3CA activating mutation H1047R on the secretion of angiogenic factors, antibody arrays were performed in the primary ECs carrying WT PIK3CA or the H1047R mutation. Angiopoietin-2 (ANG2) protein expression was decreased in PIK3CA$^{H1047R}$ but not in the PIK3CA$^{WT}$ or control cells (FIG. 20E).

Because ANG2 is a cytokine that is regulated by Forkhead O (FOXO) transcription factors downstream of the PI3K/AKT pathway, inhibits blood vessel leakage (35), and plays a role in the pathogenesis of lymphatic malformations and VM (12, 20, 36), it was confirmed that the primary ECs displayed decreased expression of ANG2. Consistently, PIK3CA$^{H1047R}$ mutant ECs had lower expression of ANG2 mRNA and secreted ANG2 protein compared to the PIK3CA$^{WT}$ cells and empty vector controls (FIG. 20F). Next, PIK3CA$^{H1047R}$ ECs were treated with different inhibitors of the PI3K/AKT/mTOR pathway, namely BYL719 (PI3Kα), MK2206 (AKT), and everolimus (mTOR). It was observed that both PI3Kα and AKT inhibitors were able to rescue the mRNA and protein expression of ANG2, but the mTOR inhibitor everolimus was not (FIG. 20F).

These results are in agreement with previous evidence describing this secretory phenotype in VM, where PDGFB and ANG2 are downregulated in TEK-mutant endothelial cells (12).

Human VM Harbor PIK3CA Mutations

Next, to ascertain whether the same genetic alterations triggering the phenotype in the mouse and cellular models were also present in the human condition, clinical specimens from 32 patients were examined, mainly adults (median age=36 years), diagnosed with VM (FIG. 21). The patients diagnosed with VM mainly presented with deep-seated and infiltrative masses in the skeletal muscle (53% of the cases were intramuscular, 34% involved skin, and 13% were in other locations) (FIG. 21). Histologically these lesions displayed a mixed pattern of vascular proliferation, including thick-walled malformed vessels, cavernous spaces filled with erythrocytes, and capillary areas (FIG. 19D), and these were radiologically detected by routine MM scans (FIG. 19E). These VMs were analyzed by targeted exome sequencing of 341 cancer-related genes using the MSK-IMPACT assay (37), yielding a median coverage of 588X. This assay was complemented with next generation deep sequencing targeted to the TEK locus. Deep sequencing detected PIK3CA mutations in 25% (8/32) of cases in previously described (38) hot spots encoding for the gain-of-function mutations H1047R (3/32) and E542K (3/32) with an allele frequency ranging from 3 to 15% (FIG. 19F; 20G). Two other mutations in PIK3CA were also identified, coding for C420R and I143V. In addition, gain-of-function mutations were found in other genes related to the PI3K pathway such as AKT2, AKT3, and IRS2, resulting in an overall frequency of approximately 30% of mutations in the PI3K/AKT pathway (FIG. 19G; FIG. 21).

Fluorescence in situ hybridization (FISH) analysis for PIK3CA and PTEN was conducted in all the VM patient samples sequenced. No amplification of PIK3CA or deletion of PTEN was found in any of the samples analyzed (FIG. 20H). Furthermore, isolated mutations were identified in genes involved in the MAPK pathway (GNAQ, NF1, MAP2K1, MAP3K1) in 13% of the cases (FIG. 19G).

Previously described mutations in the tyrosine kinase receptor TEK (3, 7) were found in 35% of the patients of the cohort, with allele frequencies ranging from 4 to 15%. These mutations were mutually exclusive with the mutations in the PI3K pathway, with the exception of one case (FIG. 19H). No mutation were detected in 5 of the 32 samples analyzed (FIG. 21).

Ubiquitous Expression of PIK3CA$^{H1047R}$ Spontaneously Induces VM in Mice

Figure 23A:
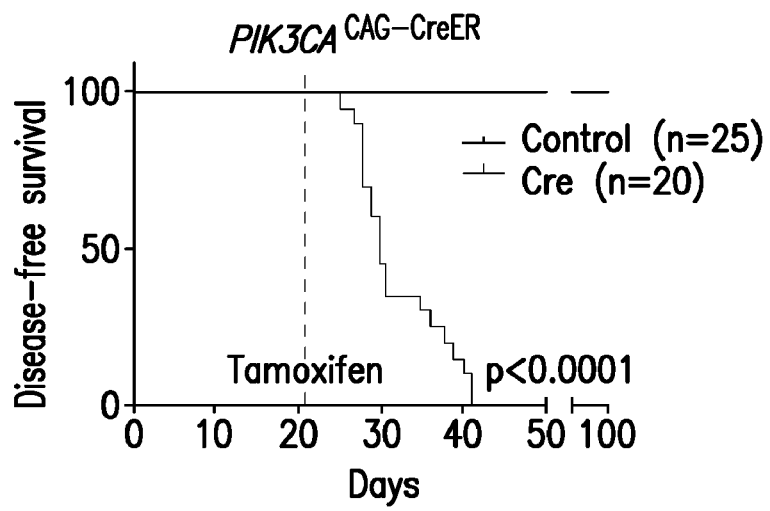
Figures 23B, 23C, 23D:
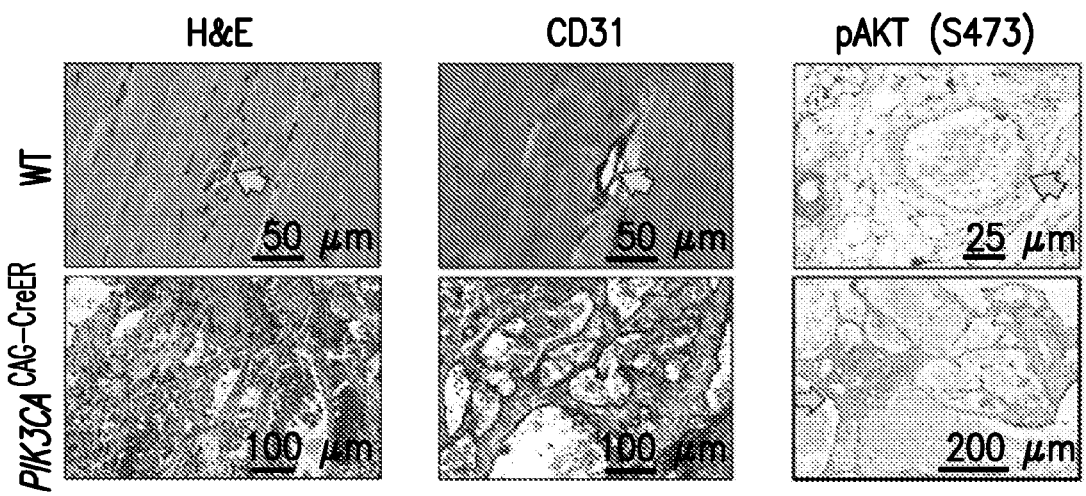

PIK3CA$^{CAG-CreER}$ mice were generated, in which the PIK3CA$^{H1047R}$ allele is ubiquitously expressed upon tamoxifen administration (40) (FIG. 22A). Six to eight week-old mice fed with tamoxifen rapidly developed cutaneous VM with 100% penetrance compared to their PIK3CA$^{WT}$ littermates (FIG. 23A). Histologic assessment confirmed a combined capillary and cavernous phenotype exhibiting dilated blood channels filled with erythrocytes (FIG. 23B) and immunoreactivity for CD31 (FIG. 23C) and phosphorylated AKT (S473), a surrogate marker of PI3K activation (FIG. 23D).

Figure 23E:
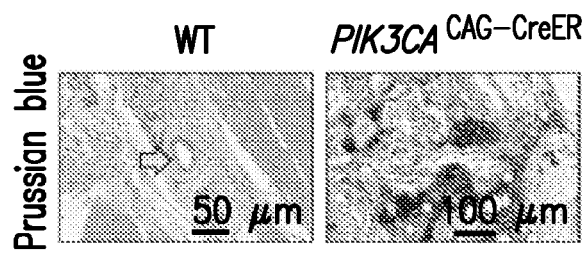
Figure 23F:
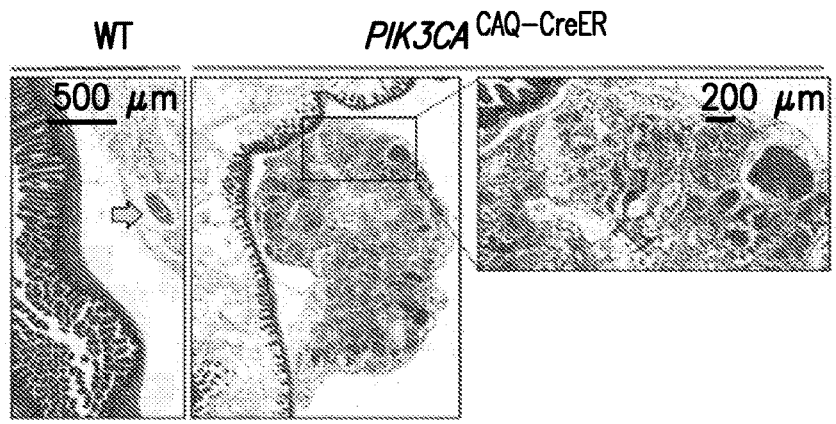
Figure 23G:
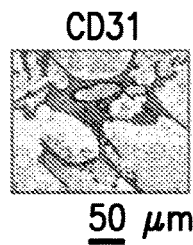
Figure 23H:
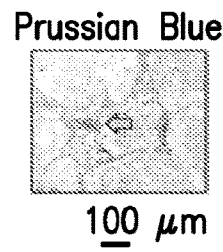

Similar to the human VM, murine vascular lesions from the PIK3CA$^{CAG-CreER}$ mice were negative for GLUT-1, WT-1, LYVE-1, and PROX-1 (FIGS. 22B-E) and contained high amounts of hemosiderin deposition (FIG. 23E). Although the skin phenotype was readily evident, additional lesions were observed at necropsy at multiple sites including mesentery, genitourinary tract, kidney, and retina (FIG. 23F), with no apparent difference in the incidence by anatomic site. Histological analyses of these lesions revealed large spaces filled with blood and lined by flattened ECs, with a similar immunophenotype, positive for CD31 and Prussian blue staining (FIG. 23G-H).

Figure 23J:
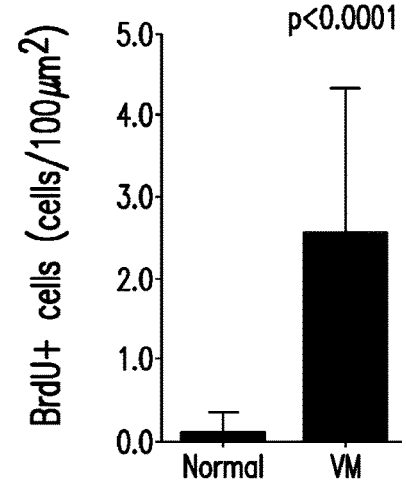
Figure 23I:
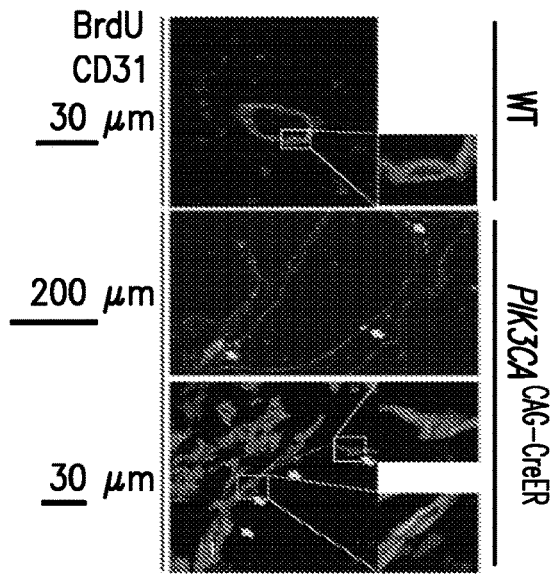
Figure 23K:
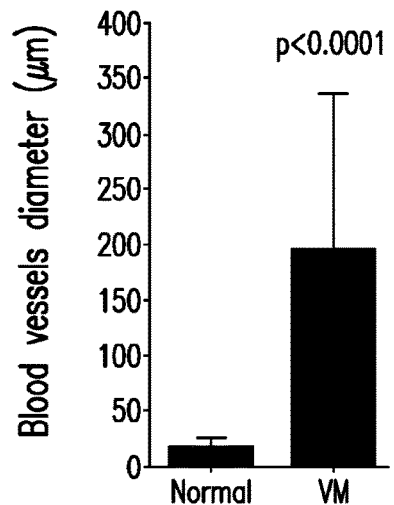
Figure 24C:
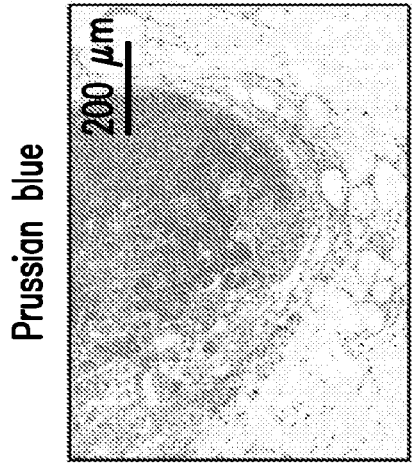
Figure 24F:
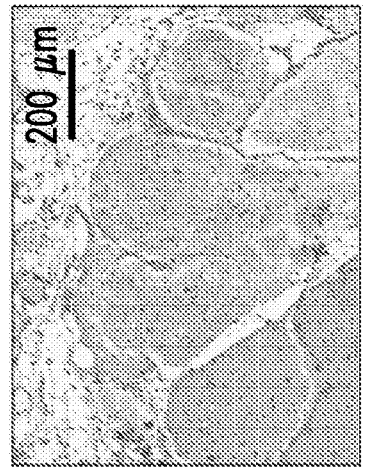
Figure 24B:
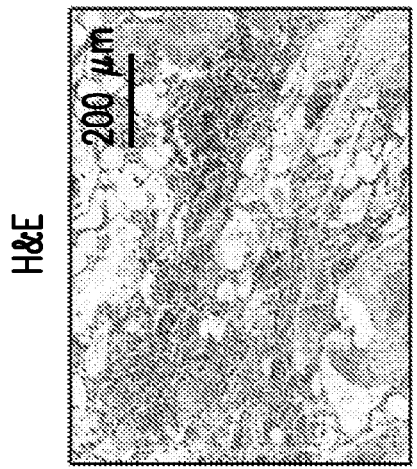
Figure 24E:
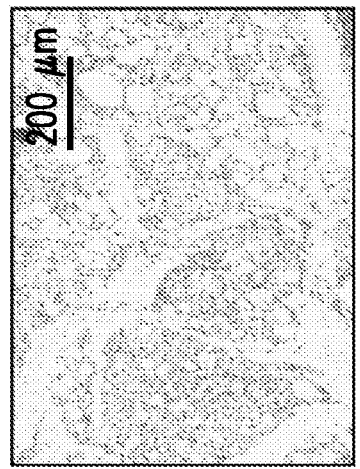
Figure 24A:
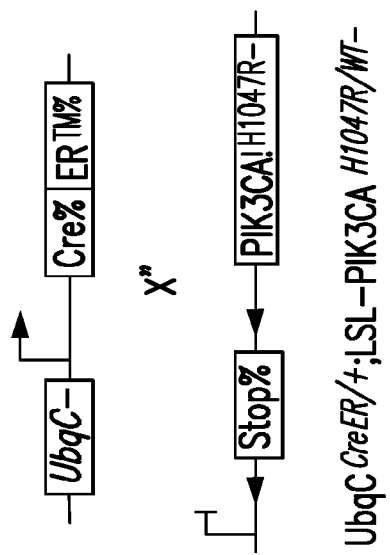
Figure 24D:
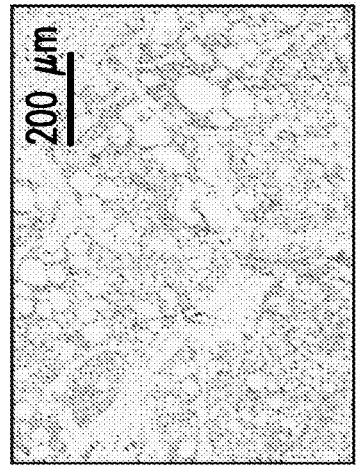

These findings were confirmed using the UBC-CreER strain, another transgenic strain in which the Ubiquitin C promoter drives the expression of a tamoxifen-inducible Cre-recombinase in all the cells of the organism (41) (FIG. 24). Consistently, the results indicated that upon ubiquitous expression of the oncogenic PIK3CA transgene, the cell of origin for VM might be more sensitive to transformation than other cell types, resulting in the genesis of VM. To test whether the formation of VM in the mouse model results, at least in part, from increased proliferation caused by hyperactive PI3K signaling (42, 43), BrdU incorporation and Ki67 staining was measured in both PIK3CA$^{WT}$ and PIK3CA$^{CAG-CreER}$ littermates. Whereas normal blood vessels were negative for BrdU incorporation as a consequence of EC quiescence (44), VM displayed a marked increase in proliferative cells (FIG. 23I-J). In agreement with the BrdU data, Ki-67 positivity was found in the VM (FIG. 25A, B). At the morphological level, quantification of the lumen diameter from normal blood vessels and VM revealed a 10-fold increase in the size of these structures in VM samples (FIG. 23K).

PI3K Inhibitors are Effective in the Treatment of PIK3CA-Induced VM

Figure 26A:
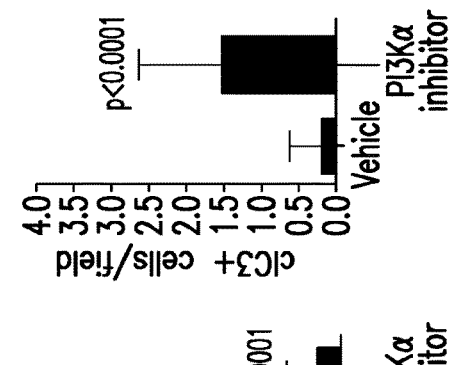
Figure 26B:
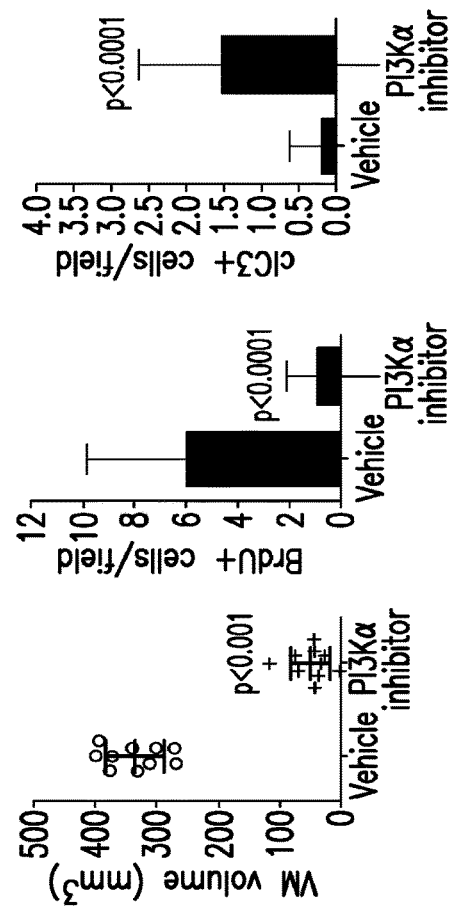
Figure 26C:
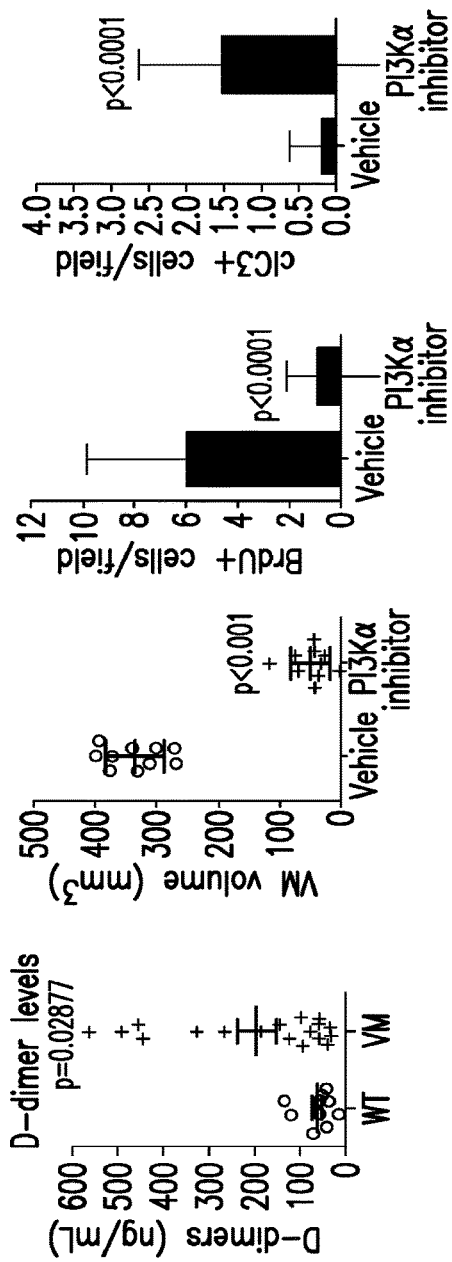

The presence of oncogenic PIK3CA mutations in human specimens of VM, together with the observed phenotypes in mice, prompted evaluation of the full growth potential of these lesions, despite the fact that they are considered to be vascular malformations. To this end, PIK3CA$^{CAG-CreER}$ VM cells were injected into recipient immunocompromised nude mice. These cells formed highly vascularized and proliferative masses a few weeks after injection, with a histology and appearance highly resembling that of the original lesions (FIG. 26A). Allotransplanted VM formed new cystic structures that contained blood and exhibited intravascular coagulopathy, as measured by the increased concentration of D-dimers in plasma (FIG. 26B), a useful tool for the differential diagnosis of venous malformations in human patients (46).

Figure 26D:
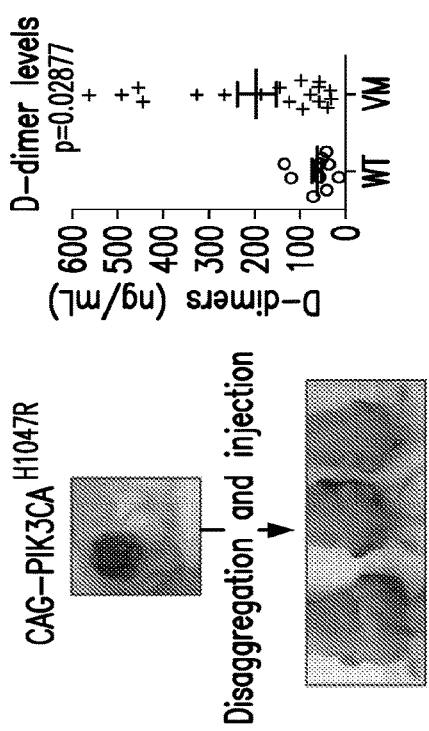
Figure 26E:
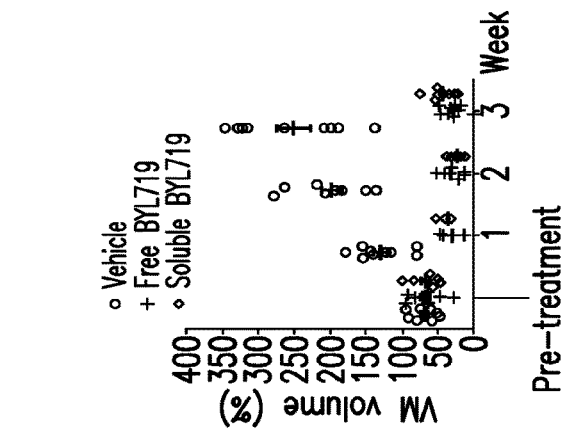
Figure 26F:
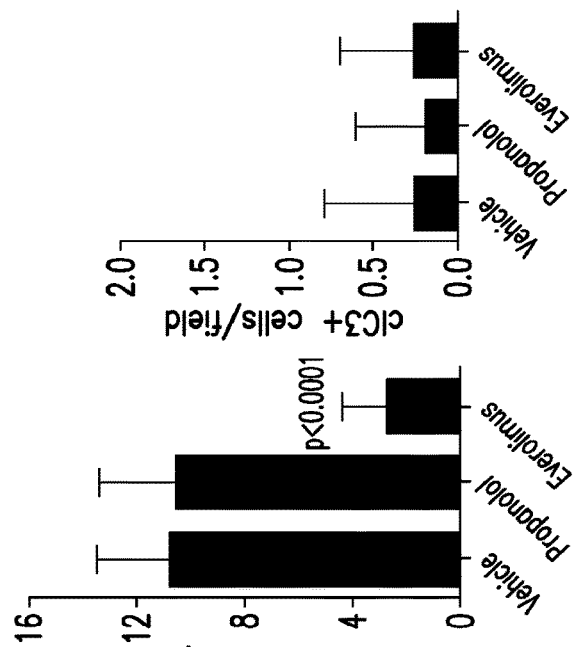

Treatment of VM with the PI3Kα selective inhibitor BYL719 resulted in a marked response as measured by a decrease in VM volume (FIG. 26C), reduced proliferation, and increased apoptosis (FIG. 26D, 25C). On the contrary, treatment with the β-adrenergic antagonist propranolol, an active agent against IH (28), did not yield any effect (FIG. 26E, F, 25D). In support of the role of the aberrant activation of the PI3K/mTOR pathway in VM, treatment with the mTOR inhibitor everolimus (48, 49) partially decreased VM size and proliferation in a similar fashion as PI3K inhibition, although it did not increase apoptosis (FIG. 4E, F, S5D).

VM may be defined as a disease characterized by the presence of somatic activating mutations in the TIE2-PI3K-AKT axis (FIGS. 19G and H). Because the TIE2 receptor, encoded by TEK, is immediately upstream from PI3K and signals via PI3K itself, treatment with PI3K inhibitors might also be efficacious in VM harboring TEK mutations. Treatment of HUVEC cells stably expressing the TEK mutation L914F with the PI3Kα inhibitor BYL719 decreased the amount of phosphorylated AKT (T308 and S473) (FIG. 27A), suggesting that PI3K inhibitors may be efficacious for VM with either PIK3CA or TEK mutations.

Figure 26G:
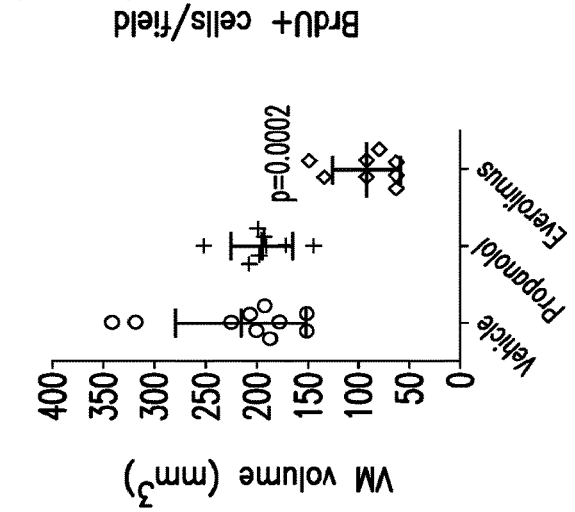

Given that a large number of VM are detected in skin or superficial tissues, together with the substantial toxicity of systemic administration of PI3K inhibitors in patients (50), two different topical cream preparations containing the PI3Kα-inhibitor BYL719 at 1% (w/w): one preparation with the inhibitor dispersed directly into the cream base and another one with the inhibitor pre-solubilized in DMSO. Topical administration of the PI3Kα inhibitor using these two different cream formulas achieved a rapid and sustained regression of skin lesions (FIG. 26G, 27B). Altogether, the results indicate that VM have tumorigenic growth potential as evidenced by their ability to engraft in nude mice, and that treatment with PI3K inhibitors either systemically or locally is a suitable pharmacological approach to control the disease.

Expression of Mutant PIK3CA Impairs Normal Vasculogenesis

Figure 29A:
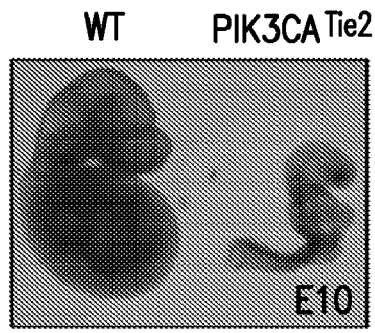
Figure 29B:
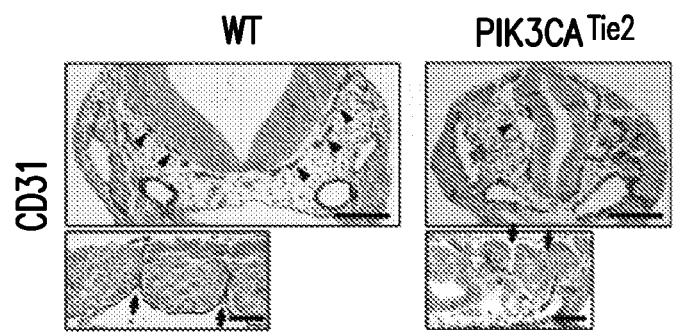
Figure 29C:
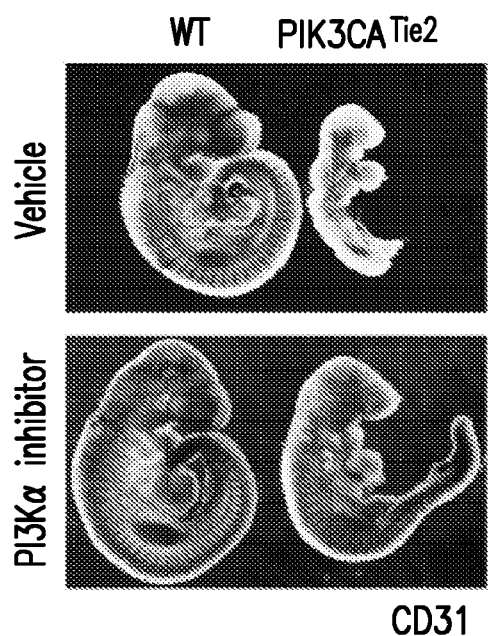
Figure 29D:
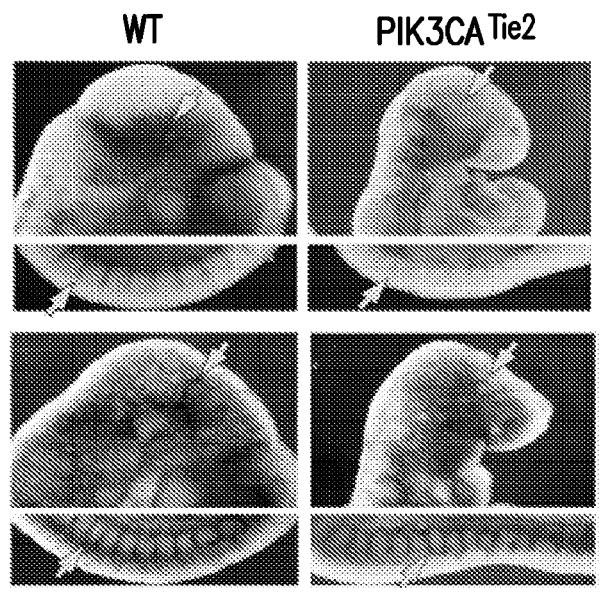
Figure 29E:
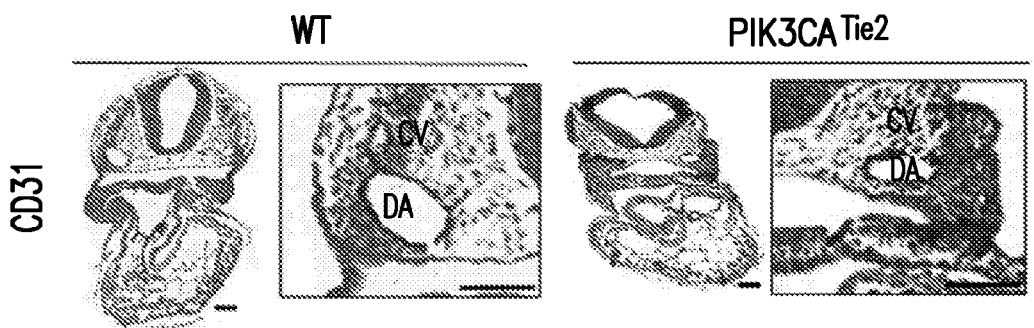

VM may occur as a result of defects during angiogenesis, a process in which PI3Kα is actively involved (17, 18, 51). To explore the biological relevance of PI3K hyperactivation specifically in blood vessels, PIK3CA$^{H1047R}$ mice were crossed with the Tie2-Cre strain (52), which drives the expression of the transgene in ECs (FIG. 28A). PIK3CA$^{Tie2-Cre}$ mice were not viable because of early embryonic lethality (E-10) resulting from vascular defects (FIG. 29A) CD31 staining of coronal sections revealed dilated blood vessels and vascular anomalies (FIG. 5B, upper panel) present in meningeal vessels, cardinal vein, and dorsal aorta. Moreover, small intersomitic vessels failed to form (FIG. 29B, lower panel), suggesting that deregulated PI3K activity results in lethal impairment of small vessel formation (17). These malformations were also evident in whole-mount embryo CD31 staining, with aberrant formation of the cephalic and intersomitic vessels (FIG. 29C-D, upper panels). Morphology, proliferation, and apoptosis were not altered in PIK3CA$^{Tie2-Cre}$ embryos' hearts (FIG. 28B-D), suggesting that the observed phenotype is caused by a defect specifically affecting blood vessel formation.

To validate the implication of excessive PI3K signaling in aberrant vasculogenesis, and to evaluate whether pharmacological inhibition could overcome this effect, it was attempted to revert the phenotype by treating pregnant mice with the PI3Kα inhibitor BYL719. PIK3CA$^{Tie2-Cre}$ E9.5 embryos treated with the PI3Kα inhibitor showed an overall body size comparable to PIK3CA$^{WT}$ littermates, suggesting improved vascular function (FIG. 28E). CD31 whole-mount staining revealed restored cephalic and intersomitic small blood vessel formation (FIG. 29C-D, lower panels). Phospho-AKT staining showed a strong reduction in both PIK3CA$^{Tie2-Cre}$ and PIK3CA$^{WT}$ embryos after PI3Kα inhibitor treatment, in contrast with untreated control embryos (FIG. 28F).

At the histologic level, treatment reestablished meningeal, cardinal vein, and dorsal aorta blood vessel morphology (FIG. 29E), indicating that aberrant PI3K pathway hyperactivation impairs normal embryonic angiogenesis in mice.

8.3 Discussion

Venous malformations are the most common vascular anomalies in humans (2) and are a cause of pain, functional limitations of the affected areas, aesthetic disfigurements, and coagulopathies. In severe cases, sclerotherapy or surgical resection may be considered; however, these procedures often involve complications such as cutaneous necrosis, or extended inflammatory reactions (53), and depending on the anatomic location and extension may have limited applicability. Moreover VM are prone to recur and recanalize (54), raising the need for developing more effective therapies.

Genetically engineered mouse models represent reliable tools for investigating the etiology, biology, and progression of human diseases, as well as for exploring new therapeutic approaches (55, 56). The first somatic molecular alterations linked to the development of sporadic VM were the acquisition of gain-of-function mutations in the gene encoding the EC specific tyrosine-kinase receptor TIE2 (TEK) (3, 8, 57, 58). Ligand-independent receptor activation drives constitutive activation of the PI3K/AKT and MAPK pathways, resulting in increased proliferation and survival of EC that could account for increased EC accumulation in VM and abnormal recruitment of smooth muscle cells. However, only a subgroup of VM harbor defects in TEK, suggesting that other genomic or molecular alterations may be at play in this disease.

Recent studies performing xenograft experiments with HUVECs transduced with the most frequent TEK mutation, L914F, have demonstrated its functional relevance in inducing VM (11). Treatment of murine xenografts with rapamycin proved the efficacy of inhibiting mTOR activity, which also showed clinical activity in VM patients in a pilot trial. Intriguingly, three out of five patients that responded to mTOR inhibition in this study did not harbor any genetic defect in TEK (11).

In the present study, the generation of a GEMM for VM is described by inducing the expression of the gain-of-function PIK3CAH1047R mutant allele in mice. The histopathologic resemblance of the lesions arising in mice to those affecting humans prompted evaluation of the existence of similar alterations in clinical specimens. Through targeted exome sequencing, it was found that 25% of the evaluated samples bear activating mutations in PIK3CA or additional genetic defects predicted to stimulate constitutive downstream signaling. To reconcile these findings with those previously reported, it was confirmed that 35% of the patients harbored mutations in TEK, yet these were mutually exclusive with the presence of activating PI3K mutations.

Patients suffering from congenital lipomatous overgrowth, vascular malformations, epidermal nevi, and skeletal/spinal abnormalities (CLOVES) syndrome harbor somatic mosaicism for activating PIK3CA mutations resulting in hyperactive PI3K/AKT signaling (60). The presence of somatic mutations in PIK3CA was also detected in patients affected by Klippel-Trenaunay Weber syndrome (KTS), an overgrowth condition with features overlapping those of CLOVES syndrome: isolated lymphatic malformations, fibro-adipose hyperplasia, and fibro-adipose vascular anomalies (61, 62). Additional genetic alterations in PTEN, GNAQ, AKT isoforms, or the regulatory subunit of PI3K, PIK3R1, which enhance PI3K/AKT/mTOR and APK pathway activation have also been reported in other malformation syndromes including *Proteus* (63), megalencephaly capillary malformation (MCAP) (64), Sturge-Weber (65), and Bannayan-Riley-Ruvalcaba (66) syndromes, underscoring the involvement of aberrant PI3K/AKT/mTOR signaling in developmental disorders. Interestingly, the MCAP syndrome exhibits a predominant brain overgrowth phenotype in which PIK3CA mutations are also involved. A recent report has described the first mouse model for brain overgrowth using GEMM of PIK3CA mutants E545K and H1047R, validating the importance of these mouse models in the study of PIK3CA-driven syndromes (67). Nevertheless, sporadic and solitary VM lesions are a different and much more prevalent entity that is not necessarily associated with overgrowth.

Despite the fact that most lymphatic malformations carry PIK3CA mutations, the mouse model described by the present example does not present detectable lymphatic anomalies. Our observations are further supported by those made by Castillo and colleagues, who found that mosaic somatic mutations induced in a PIK3CA$^{H1047R}$ mouse model cause VM that are neither associated with tissue overgrowth nor lymphatic malformations (35), suggesting that the cell of origin giving rise to VM may be more susceptible to hyperactive PI3K signaling than other cell lineages and that additional genetic or environmental cues are required to reproduce the complex phenotypes observed in overgrowth syndromes.

However, the present example shows that not only is overactivation of PI3K/AKT signaling involved in VM formation, but inhibition of this pathway can rescue VM phenotypes. Given the ability of the mouse model described herein to recapitulate the pathogenesis of human VM, whether it could be used as a platform for testing pharmacological inhibition using PI3K inhibitors currently under clinical development was confirmed. The efficacy of other agents that have been proposed to inhibit the growth of VM were also evaluated, including rapamycin analogues and propranolol (11, 68). The greatest growth inhibition was achieved when treating allograft transplants with a PI3Kα inhibitor or the rapamycin analogue everolimus, but no effect was observed with propranolol.

Topical administration of a PI3Kα inhibitor further demonstrated the efficacy of this treatment with an approach that would be devoid of the substantial side effects associated with systemic drug administration (hyperglycemia, nausea, gastrointestinal effects, and fatigue) (50). The impaired vasculogenesis observed in mouse embryos as a consequence of endothelial-restricted expression of the PIK3CA$^{H1047R}$ allele was also rescued when pregnant mice were treated with the PI3Kα inhibitor.

In summary, the present example provides a GEMM recapitulating human VM caused by hyperactivation of the PI3K/AKT pathway, reveals the impact of PIK3CA somatic mutations in the pathogenesis of VM, and provides a therapeutic approach to treat advanced or recurrent lesions in these patients.

REFERENCES

1. H. L. Nguyen, L. M. Boon, M. Vikkula, Genetics of vascular malformations. Seminars in pediatric surgery 23, 221-226 (2014).
2. M. Uebelhoer, L. M. Boon, M. Vikkula, Vascular anomalies: from genetics toward models for therapeutic trials. Cold Spring Harbor perspectives in medicine 2, (2012).
3. N. Limaye, V. Wouters, M. Uebelhoer, M. Tuominen, R. Wirkkala, J. B. Mulliken, L. Eklund, L. M. Boon, M. Vikkula, Somatic mutations in angiopoietin receptor gene TEK cause solitary and multiple sporadic venous malformations. Nature genetics 41, 118-124 (2009).
4. P. Brouillard, M. Vikkula, Genetic causes of vascular malformations. Human molecular genetics 16 Spec No. 2, R140-149 (2007).
5. P. Brouillard, M. Vikkula, Vascular malformations: localized defects in vascular morphogenesis. Clinical genetics 63, 340-351 (2003).
6. A. Dompmartin, M. Vikkula, L. M. Boon, Venous malformation: update on aetiopathogenesis, diagnosis and management. Phlebology/Venous Forum of the Royal Society of Medicine 25, 224-235 (2010).
7. J. Soblet, N. Limaye, M. Uebelhoer, L. M. Boon, M. Vikkula, Variable Somatic TIE2 Mutations in Half of Sporadic Venous Malformations. Molecular syndromology 4, 179-183 (2013).
8. M. Vikkula, L. M. Boon, K. L. Carraway, 3rd, J. T. Calvert, A. J. Diamonti, B. Goumnerov, K. A. Pasyk, D. A. Marchuk, M. L. Warman, L. C. Cantley, J. B. Mulliken, B. R. Olsen, Vascular dysmorphogenesis caused by an activating mutation in the receptor tyrosine kinase TIE2. Cell 87, 1181-1190 (1996).
9. C. D. Kontos, T. P. Stauffer, W. P. Yang, J. D. York, L. Huang, M. A. Blanar, T. Meyer, K. G. Peters, Tyrosine 1101 of Tie2 is the major site of association of p85 and is required for activation of phosphatidylinositol 3-kinase and Akt. Molecular and cellular biology 18, 4131-4140 (1998).
10. P. N. Morris, B. J. Dunmore, A. Tadros, D. A. Marchuk, D. C. Darland, P. A. D'Amore, N. P. Brindle, Functional analysis of a mutant form of the receptor tyrosine kinase Tie2 causing venous malformations. Journal of molecular medicine 83, 58-63 (2005).
11. E. Boscolo, N. Limaye, L. Huang, K. T. Kang, J. Soblet, M. Uebelhoer, A. Mendola, M. Natynki, E. Seront, S. Dupont, J. Hammer, C. Legrand, C. Brugnara, L. Eklund, M. Vikkula, J. Bischoff, L. M. Boon, Rapamycin improves TIE2-mutated venous malformation in murine model and human subjects. The Journal of clinical investigation 125, 3491-3504 (2015).
12. M. Uebelhoer, M. Natynki, J. Kangas, A. Mendola, H. L. Nguyen, J. Soblet, C. Godfraind, L. M. Boon, L. Eklund, N. Limaye, M. Vikkula, Venous malformation-causative TIE2 mutations mediate an AKTdependent decrease in PDGFB. Human molecular genetics 22, 3438-3448 (2013).
13. M. Natynki, J. Kangas, I. Miinalainen, R. Sormunen, R. Pietila, J. Soblet, L. M. Boon, M. Vikkula, N. Limaye, L. Eklund, Common and specific effects of TIE2 mutations causing venous malformations. Human molecular genetics 24, 6374-6389 (2015).
14. D. A. Fruman, C. Rommel, PI3K and cancer: lessons, challenges and opportunities. Nature reviews. Drug discovery 13, 140-156 (2014).
15. J. A. Engelman, Targeting PI3K signalling in cancer: opportunities, challenges and limitations. Nature reviews. Cancer 9, 550-562 (2009).
16. K. M. Keppler-Noreuil, J. J. Rios, V. E. Parker, R. K. Semple, M. J. Lindhurst, J. C. Sapp, A. Alomari, M. Ezaki, W. Dobyns, L. G. Biesecker, PIK3CA-related overgrowth spectrum (PROS): diagnostic and testing eligibility criteria, differential diagnosis, and evaluation. American journal of medical genetics. Part A 167A, 287-295 (2015).
17. M. Graupera, J. Guillermet-Guibert, L. C. Foukas, L. K. Phng, R. J. Cain, A. Salpekar, W. Pearce, S. Meek, J. A Millan, P. R. Cutillas, A. J. Smith, A. J. Ridley, C. Ruhrberg, H. Gerhardt, B. Vanhaesebroeck, Angiogenesis selectively requires the p110alpha isoform of PI3K to control endothelial cell migration. Nature 453, 662-666 (2008).
18. M. Graupera, M. Potente, Regulation of angiogenesis by PI3K signaling networks. Experimental cell research 319, 1348-1355 (2013).
19. H. C. Kang, S. T. Baek, S. Song, J. G. Gleeson, Clinical and Genetic Aspects of the Segmental Overgrowth Spectrum Due to Somatic Mutations in PIK3CA. The Journal of pediatrics, (2015).
20. A. J. Osborn, P. Dickie, D. E. Neilson, K. Glaser, K. A. Lynch, A. Gupta, B. H. Dickie, Activating PIK3CA alleles and lymphangiogenic phenotype of lymphatic endothelial cells isolated from lymphatic malformations. Human molecular genetics 24, 926-938 (2015).
21. N. Cancer Genome Atlas Research, C. Kandoth, N. Schultz, A. D. Cherniack, R. Akbani, Y. Liu, H. Shen, A. G. Robertson, I. Pashtan, R. Shen, C. C. Benz, C. Yau, P. W. Laird, L. Ding, W. Zhang, G. B. Mills, R. Kucherlapati, E. R. Mardis, D. A. Levine, Integrated genomic characterization of endometrial carcinoma. Nature 497, 67-73 (2013).
22. J. R. Adams, K. Xu, J. C. Liu, N. M. Agamez, A. J. Loch, R. G. Wong, W. Wang, K. L. Wright, T. F. Lane, E. Zacksenhaus, S. E. Egan, Cooperation between Pik3ca and p53 mutations in mouse mammary tumor formation. Cancer research 71, 2706-2717 (2011).
23. C. M. Contreras, E. A. Akbay, T. D. Gallardo, J. M. Haynie, S. Sharma, O. Tagao, N. Bardeesy, M. Takahashi, J. Settleman, K. K. Wong, D. H. Castrillon, Lkb1 inactivation is sufficient to drive endometrial cancers that are aggressive yet highly responsive to mTOR inhibitor monotherapy. Disease models & mechanisms 3, 181-193 (2010).
24. T. Krings, Vascular malformations of the spine and spinal cord*: anatomy, classification, treatment. Clinical neuroradiology 20, 5-24 (2010).
25. M. Wassef, F. Blei, D. Adams, A. Alomari, E. Baselga, A. Berenstein, P. Burrows, I. J. Frieden, M. C. Garzon, J. C. Lopez-Gutierrez, D. J. Lord, S. Mitchel, J. Powell, J. Prendiville, M. Vikkula, I. Board, C. Scientific, Vascular Anomalies Classification: Recommendations From the International Society for the Study of Vascular Anomalies. Pediatrics, (2015).
26. P. E. North, M. Waner, A. Mizeracki, M. C. Mihm, Jr., GLUT1: a newly discovered immunohistochemical marker for juvenile hemangiomas. Human pathology 31, 11-22 (2000).
27. L. P. Lawley, F. Cerimele, S. W. Weiss, P. North, C. Cohen, H. P. Kozakewich, J. B. Mulliken, J. L. Arbiser, Expression of Wilms tumor 1 gene distinguishes vascular malformations from proliferative endothelial lesions. Archives of dermatology 141, 1297-1300 (2005).
28. C. Leaute-Labreze, P. Hoeger, J. Mazereeuw-Hautier, L. Guibaud, E. Baselga, G. Posiunas, R. J. Phillips, H. Caceres, J. C. Lopez Gutierrez, R. Ballona, S. F. Friedlander, J. Powell, D. Perek, B. Metz, S. Barbarot, A. Maruani, Z. Z. Szalai, A. Krol, O. Boccara, R. Foelster-Holst, M. I. Febrer Bosch, J. Su, H. Buckova, A. Torrelo, F. Cambazard, R. Grantzow, O. Wargon, D. Wyrzykowski, J. Roessler, J. Bernabeu-Wittel, A. M. Valencia, P. Przewratil, S. Glick, E. Pope, N. Birchall, L. Benjamin, A. J. Mancini, P. Vabres, P. Souteyrand, I. J. Frieden, C. I. Berul, C. R. Mehta, S. Prey, F. Boralevi, C. C. Morgan, S. Heritier, A. Delarue, J. J. Voisard, A randomized, controlled trial of oral propranolol in infantile hemangioma. The New England journal of medicine 372, 735-746 (2015).
29. P. Brouillard, L. Boon, M. Vikkula, Genetics of lymphatic anomalies. The Journal of clinical investigation 124, 898-904 (2014).
30. C. Mouta-Bellum, A. Kirov, L. Miceli-Libby, M. L. Mancini, T. V. Petrova, L. Liaw, I. Prudovsky, P. E. Thorpe, N. Miura, L. C. Cantley, K. Alitalo, D. A. Fruman, C. P. Vary, Organ-specific lymphangiectasia, arrested lymphatic sprouting, and maturation defects resulting from gene-targeting of the PI3K regulatory isoforms p85alpha, p55alpha, and p50alpha. Developmental dynamics: an official publication of the American Association of Anatomists 238, 2670-2679 (2009).
31. S. Banerji, J. Ni, S. X. Wang, S. Clasper, J. Su, R. Tammi, M. Jones, D. G. Jackson, LYVE-1, a new homologue of the CD44 glycoprotein, is a lymph-specific receptor for hyaluronan. The Journal of cell biology 144, 789-801 (1999).
32. E. C. Castro, C. Galambos, Prox-1 and VEGFR3 antibodies are superior to D2-40 in identifying endothelial cells of lymphatic malformations—a proposal of a new immunohistochemical panel to differentiate lymphatic from other vascular malformations. Pediatric and developmental pathology: the official journal of the Society for Pediatric Pathology and the Paediatric Pathology Society 12, 187-194 (2009).
33. I. Arnaoutova, J. George, H. K. Kleinman, G. Benton, The endothelial cell tube formation assay on basement membrane turns 20: state of the science and the art. Angiogenesis 12, 267-274 (2009).
34. X. L. Tian, R. Kadaba, S. A. You, M. Liu, A. A. Timur, L. Yang, Q. Chen, P. Szafranski, S. Rao, L. Wu, D. E. Housman, P. E. DiCorleto, D. J. Driscoll, J. Borrow, Q. Wang, Identification of an angiogenic factor that when mutated causes susceptibility to Klippel-Trenaunay syndrome. Nature 427, 640-645 (2004).
35. C. Daly, E. Pasnikowski, E. Burova, V. Wong, T. H. Aldrich, J. Griffiths, E. Ioffe, T. J. Daly, J. P. Fandl, N. Papadopoulos, D. M. McDonald, G. Thurston, G. D. Yancopoulos, J. S. Rudge, Angiopoietin-2 functions as an autocrine protective factor in stressed endothelial cells. Proc Natl Acad Sci USA 103, 15491-15496 (2006).
36. G. Thurston, C. Daly, The complex role of angiopoietin-2 in the angiopoietin-tie signaling pathway. Cold Spring Harbor perspectives in medicine 2, a006550 (2012).
37. D. T. Cheng, T. N. Mitchell, A. Zehir, R. H. Shah, R. Benayed, A. Syed, R. Chandramohan, Z. Y. Liu, H. H. Won, S. N. Scott, A. R. Brannon, C. O'Reilly, J. Sadowska, J. Casanova, A. Yannes, J. F. Hechtman, J. Yao, W. Song, D. S. Ross, A. Oultache, S. Dogan, L. Borsu, M. Hameed, K. Nafa, M. E. Arcila, M. Ladanyi, M. F. Berger, Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology. The Journal of molecular diagnostics: JMD 17, 251-264 (2015).
38. Y. Samuels, L. A. Diaz, Jr., O. Schmidt-Kittler, J. M. Cummins, L. Delong, I. Cheong, C. Rago, D. L. Huso, C.

Lengauer, K. W. Kinzler, B. Vogelstein, V. E. Velculescu, Mutant PIK3CA promotes cell growth and invasion of human cancer cells. Cancer cell 7, 561-573 (2005).

39. N. Jones, Z. Master, J. Jones, D. Bouchard, Y. Gunji, H. Sasaki, R. Daly, K. Alitalo, D. J. Dumont, Identification of Tek/Tie2 binding partners. Binding to a multifunctional docking site mediates cell survival and migration. The Journal of biological chemistry 274, 30896-30905 (1999).

40. S. Hayashi, A. P. McMahon, Efficient recombination in diverse tissues by a tamoxifen-inducible form of Cre: a tool for temporally regulated gene activation/inactivation in the mouse. Developmental biology 244, 305-318 (2002).

41. Y. Ruzankina, C. Pinzon-Guzman, A. Asare, T. Ong, L. Pontano, G. Cotsarelis, V. P. Zediak, M. Velez, A. Bhandoola, E. J. Brown, Deletion of the developmentally essential gene ATR in adult mice leads to agerelated phenotypes and stem cell loss. Cell stem cell 1, 113-126 (2007).

42. R. H. Adams, K. Alitalo, Molecular regulation of angiogenesis and lymphangiogenesis. Nature reviews. Molecular cell biology 8, 464-478 (2007).

43. M. C. Smith, D. Y. Li, K. J. Whitehead, Mechanisms of vascular stability and the relationship to human disease. Current opinion in hematology 17, 237-244 (2010).

44. S. P. Herbert, D. Y. Stainier, Molecular control of endothelial cell behaviour during blood vessel morphogenesis. Nature reviews. Molecular cell biology 12, 551-564 (2011).

45. Castillo S D, Tzouanacou E, Zaw-Thin M, Berenjeno I M, Parker V, Chivite I, Mild-Guasch M, Pearce W, Solomon I, Dewhurst R E, Knox R G, Scudamore C L, Badar A, Kalber T L,
Foster J, Stuckey D J, David A, Phillips W A, Lythgoe M F, Wilson V, Semple R K, Sebire N J, Kinsler V A, Graupera M, Vanhaesebroeck, B. 2015 Somatic mutation in Pik3ca causes sporadic venous malformations (Unpublished)

46. A. Dompmartin, F. Ballieux, P. Thibon, A. Lequerrec, C. Hermans, P. Clapuyt, M. T. Barrellier, F. Hammer, D. Labbe, M. Vikkula, L. M. Boon, Elevated D-dimer level in the differential diagnosis of venous malformations. Archives of dermatology 145, 1239-1244 (2009).

47. C. Fritsch, A. Huang, C. Chatenay-Rivauday, C. Schnell, A. Reddy, M. Liu, A. Kauffmann, D. Guthy, D. Erdmann, A. De Pover, P. Furet, H. Gao, S. Ferretti, Y. Wang, J. Trappe, S. M. Brachmann, S. M. Maira, C. Wilson, M. Boehm, C. Garcia-Echeverria, P. Chene, M. Wiesmann, R. Cozens, J. Lehar, R. Schlegel, G. Caravatti, F. Hofmann, W. R. Sellers, Characterization of the novel and specific PI3Kalpha inhibitor NVPBYL719 and development of the patient stratification strategy for clinical trials. Molecular cancer therapeutics 13, 1117-1129 (2014).

48. H. Lackner, A. Karastaneva, W. Schwinger, M. Benesch, P. Sovinz, M. Seidel, D. Sperl, S. Lanz, E. Haxhija, F. Reiterer, E. Sorantin, C. E. Urban, Sirolimus for the treatment of children with various complicated vascular anomalies. European journal of pediatrics, (2015).

49. A. M. Hammill, M. Wentzel, A. Gupta, S. Nelson, A. Lucky, R. Elluru, R. Dasgupta, R. G. Azizkhan, D. M. Adams, Sirolimus for the treatment of complicated vascular anomalies in children. Pediatric blood & cancer 57, 1018-1024 (2011).

50. J. Rodon, R. Dienstmann, V. Serra, J. Tabernero, Development of PI3K inhibitors: lessons learned from early clinical trials. Nature reviews. Clinical oncology 10, 143-153 (2013).

51. L. M. Hare, Q. Schwarz, S. Wiszniak, R. Gurung, K. G. Montgomery, C. A. Mitchell, W. A. Phillips, Heterozygous expression of the oncogenic Pik3ca(H1047R) mutation during murine development results in fatal embryonic and extraembryonic defects. Developmental biology 404, 14-26 (2015).

52. Y. Y. Kisanuki, R. E. Hammer, J. Miyazaki, S. C. Williams, J. A. Richardson, M. Yanagisawa, Tie2-Cre transgenic mice: a new model for endothelial cell-lineage analysis in vivo. Developmental biology 230, 230-242 (2001).

53. J. A. Cox, E. Bartlett, E. I. Lee, Vascular Malformations: A Review. Semin Plast Surg 28, 58-63 (2014).

54. A. A. Delorimier, Sclerotherapy for Venous Malformations. J Pediatr Surg 30, 188-194 (1995).

55. J. Heyer, L. N. Kwong, S. W. Lowe, L. Chin, Non-germline genetically engineered mouse models for translational cancer research. Nat Rev Cancer 10, 470-480 (2010).

56. M. H. van Miltenburg, J. Jonkers, Using genetically engineered mouse models to validate candidate cancer genes and test new therapeutic approaches. Curr Opin Genet Dev 22, 21-27 (2012).

57. J. T. Calvert, T. J. Riney, C. D. Kontos, E. H. Cha, V. G. Prieto, C. R. Shea, J. N. Berg, N. C. Nevin, S. A. Simpson, K. A. Pasyk, M. C. Speer, K. G. Peters, D. A. Marchuk, Allelic and locus heterogeneity in inherited venous malformations. Human molecular genetics 8, 1279-1289 (1999).

58. V. Wouters, N. Limaye, M. Uebelhoer, A. Irrthum, L. M. Boon, J. B. Mulliken, O. Enjolras, E. Baselga, J. Berg, A. Dompmartin, S. A. Ivarsson, L. Kangesu, Y. Lacassie, J. Murphy, A. S. Teebi, A. Penington, P. Rieu, M. Vikkula, Hereditary cutaneomucosal venous malformations are caused by TIE2 mutations with widely variable hyperphosphorylating effects. Eur J Hum Genet 18, 414-420 (2010).

59. I. Kim, H. G. Kim, J. N. So, J. H. Kim, H. J. Kwak, G. Y. Koh, Angiopoietin-1 regulates endothelial cell survival through the phosphatidylinositol 3'-Kinase/Akt signal transduction pathway. Circulation research 86, 24-29 (2000).

60. K. C. Kurek, V. L. Luks, U. M. Ayturk, A. I. Alomari, S. J. Fishman, S. A. Spencer, J. B. Mulliken, M. E. Bowen, G. L. Yamamoto, H. P. Kozakewich, M. L. Warman, Somatic mosaic activating mutations in PIK3CA cause CLOVES syndrome. American journal of human genetics 90, 1108-1115 (2012).

61. V. L. Luks, N. Kamitaki, M. P. Vivero, W. Uller, R. Rab, J. V. M. G. Bovee, K. L. Rialon, C. J. Guevara, A. I. Alomari, A. K. Greene, S. J. Fishman, H. P. W. Kozakewich, R. A. Maclellan, J. B. Mulliken, R. Rahbar, S. A. Spencer, C. C. Trenor, J. Upton, D. Zurakowski, J. A. Perkins, A. Kirsh, J. T. Bennett, W. B. Dobyns, K. C. Kurek, M. L. Warman, S. A. McCarroll, R. Murillo, Lymphatic and Other Vascular Malformative/Overgrowth Disorders Are Caused by Somatic Mutations in PIK3CA. J Pediatr-Us 166, 1048-U1376 (2015).

62. M. J. Lindhurst, V. E. Parker, F. Payne, J. C. Sapp, S. Rudge, J. Harris, A. M. Witkowski, Q. Zhang, M. P. Groeneveld, C. E. Scott, A. Daly, S. M. Huson, L. L. Tosi, M. L. Cunningham, T. N. Darling, J. Geer, Z. Gucev, V. R. Sutton, C. Tziotzios, A. K. Dixon, T. Helliwell, S. O'Rahilly, D. B. Savage, M. J. Wakelam, I. Barroso, L. G. Biesecker, R. K. Semple, Mosaic overgrowth with fibroadipose hyperplasia is caused by somatic activating mutations in PIK3CA. Nature genetics 44, 928-933 (2012).

63. M. J. Lindhurst, J. C. Sapp, J. K. Teer, J. J. Johnston, E. M. Finn, K. Peters, J. Turner, J. L. Cannons, D. Bick, L. Blakemore, C. Blumhorst, K. Brockmann, P. Calder, N. Cherman, M. A. Deardorff, D. B. Everman, G. Golas, R. M. Greenstein, B. M. Kato, K. M. Keppler-Noreuil, S. A. Kuznetsov, R. T. Miyamoto, K. Newman, D. Ng, K. O'Brien, S. Rothenberg, D. J. Schwartzentruber, V. Singhal, R. Tirabosco, J. Upton, S. Wientroub, E. H. Zackai, K. Hoag, T. Whitewood-Neal, P. G. Robey, P. L. Schwartzberg, T. N. Darling, L. L. Tosi, J. C. Mullikin, L. G. Biesecker, A mosaic activating mutation in AKT1 associated with the Proteus syndrome. The New England journal of medicine 365, 611-619 (2011).

64. J. B. Riviere, G. M. Mirzaa, B. J. O'Roak, M. Beddaoui, D. Alcantara, R. L. Conway, J. St-Onge, J. A. Schwartzentruber, K. W. Gripp, S. M. Nikkel, T. Worthylake, C. T. Sullivan, T. R. Ward, H. E. Butler, N. A. Kramer, B. Albrecht, C. M. Armour, L. Armstrong, O. Caluseriu, C. Cytrynbaum, B. A. Drolet, A. M. Innes, J. L. Lauzon, A. E. Lin, G. M. Mancini, W. S. Meschino, J. D. Reggin, A. K. Saggar, T. Lerman-Sagie, G. Uyanik, R. Weksberg, B. Zirn, C. L. Beaulieu, C. Finding of Rare Disease Genes Canada, J. Majewski, D. E. Bulman, M. O'Driscoll, J. Shendure, J. M. Graham, Jr., K. M. Boycott, W. B. Dobyns, De novo germline and postzygotic mutations in AKT3, PIK3R2 and PIK3CA cause a spectrum of related megalencephaly syndromes. Nature genetics 44, 934-940 (2012).

65. M. D. Shirley, H. Tang, C. J. Gallione, J. D. Baugher, L. P. Frelin, B. Cohen, P. E. North, D. A. Marchuk, A. M. Comi, J. Pevsner, Sturge-Weber syndrome and port-wine stains caused by somatic mutation in GNAQ. The New England journal of medicine 368, 1971-1979 (2013).

66. D. J. Marsh, P. L. Dahia, Z. Zheng, D. Liaw, R. Parsons, R. J. Gorlin, C. Eng, Germline mutations in PTEN are present in Bannayan-Zonana syndrome. Nature genetics 16, 333-334 (1997).

67. A. Roy, J. Ni, J. Skibo, S. Rankin, W. B. Dobyns, F. Kalume, S. J. Baker, J. Zhao, K. J. Millen, Modeling human PIK3CA-related congenital brain overgrowth and epilepsy in mice. International journal of developmental neuroscience: the official journal of the International Society for Developmental Neuroscience 47, 46 (2015).

68. C. Pfohler, E. Janssen, A. Buecker, T. Vogt, C. S. L. Muller, Successful treatment of a congenital extratruncal vascular malformation by orally administered propranolol. J Dermatol Treat 26, 59-62 (2015).

69. J. Blatt, T. W. McLean, S. M. Castellino, C. N. Burkhart, A review of contemporary options for medical management of hemangiomas, other vascular tumors, and vascular malformations. Pharmacology & therapeutics 139, 327-333 (2013).

70. D. D. Sarbassov, S. M. Ali, S. Sengupta, J. H. Sheen, P. P. Hsu, A. F. Bagley, A. L. Markhard, D. M. Sabatini, Prolonged rapamycin treatment inhibits mTORC2 assembly and Akt/PKB. Molecular cell 22, 159-168 (2006).

Various references are cited herein, the contents of which are hereby incorporated by reference in their entireties.

What is claimed is:

1. A method of treating a venous malformation in a subject in need thereof, comprising administering to the subject an effective amount of BYL719 (Alpelisib),
   wherein the venous malformation is not associated with congenital lipomatous overgrowth with vascular, epidermal, and skeletal anomalies syndrome (CLOVES), Klippel-Trenaunay syndrome (KTS), or fibro-adipose vascular anomaly (FAVA), and
   wherein the subject has a gain-of-function mutation in the PI3K/AKT pathway.

2. The method of claim 1, wherein the gain-of-function mutation is an activating mutation of PIK3CA, or a mutation in at least one of AKT1, AKT2, AKT3, and IRS2.

3. The method of claim 2, wherein the activating mutation is selected from the group consisting of R88Q, E542K, E545K, E545Q, H1047L, H1047Q, H1047R, C420R, and I143V.

4. The method of claim 1, wherein the venous malformation is located in the brain, and/or within the skin.

5. The method of claim 1, wherein:
   a) the subject suffers from multiple venous malformations, a malignancy, a multisystem genetic disorder, or a combination thereof; or
   b) the surgical treatment of the venous malformation would be high-risk.

6. The method of claim 1, wherein BYL719 (Alpelisib) is administered systemically or locally.

7. The method of claim 1, wherein BYL719 (Alpelisib) is administered topically, parenterally, or orally.

8. The method of claim 1, further comprising administering to the subject a second agent that inhibits the PI3K/AKT pathway, wherein the second agent is in an amount that, together with the agent of claim 1, effectively treats the venous malformation.

9. The method of claim 1, wherein the venous malformation is a sporadic venous malformation.

* * * * *